(12) United States Patent
Hsieh et al.

(10) Patent No.: US 10,928,977 B2
(45) Date of Patent: Feb. 23, 2021

(54) MOBILE TERMINAL AND METHOD OF CONTROLLING MEDICAL APPARATUS BY USING THE MOBILE TERMINAL

(71) Applicant: SAMSUNG ELECTRONICS CO., LTD., Suwon-si (KR)

(72) Inventors: Jongjyh Hsieh, Seoul (KR); Jong-pil Kim, Yongin-si (KR); Su-jin Kim, Yongin-si (KR); Woong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 77 days.

(21) Appl. No.: 15/015,213

(22) Filed: Feb. 4, 2016

(65) Prior Publication Data
US 2016/0232314 A1 Aug. 11, 2016

(30) Foreign Application Priority Data
Feb. 9, 2015 (KR) .................. 10-2015-0019658

(51) Int. Cl.
*G06F 3/048* (2013.01)
*G16H 40/63* (2018.01)
(Continued)

(52) U.S. Cl.
CPC ........ *G06F 3/04817* (2013.01); *G06F 3/0488* (2013.01); *G06F 3/04842* (2013.01);
(Continued)

(58) Field of Classification Search
CPC combination set(s) only.
See application file for complete search history.

(56) References Cited

U.S. PATENT DOCUMENTS

| 7,316,648 B2 | 1/2008 | Kelly et al. |
| 10,095,400 B2 | 10/2018 | Ban et al. |

(Continued)

FOREIGN PATENT DOCUMENTS

| CN | 103793607 A | 5/2014 |
| CN | 104380333 A | 2/2015 |

(Continued)

OTHER PUBLICATIONS

Communication dated Jun. 20, 2016 issued by the International Searching Authority in counterpart Application No. PCT/KR2016/001055 (PCT/ISA210 & 237).

(Continued)

*Primary Examiner* — Arpan P. Savla
*Assistant Examiner* — Haimei Jiang
(74) *Attorney, Agent, or Firm* — Sughrue Mion, PLLC

(57) ABSTRACT

A mobile terminal including a touch screen and a method of controlling a medical apparatus by using the mobile terminal are provided. The method may include displaying, in response to determining that at least one medical apparatus is within a certain range from the mobile terminal based on location information of the at least one medical apparatus, at least one piece of identification information that corresponds to the at least one medical apparatus, detecting a user input for selecting first identification information from the at least one piece of identification information, and displaying, in response to a user input, a user interface for controlling a first medical apparatus that corresponds to the first identification information, on the touch screen.

19 Claims, 49 Drawing Sheets

(51) Int. Cl.
*G16H 40/40* (2018.01)
*A61B 5/00* (2006.01)
*H04L 12/12* (2006.01)
*G06F 3/0481* (2013.01)
*G06F 3/0484* (2013.01)
*G06F 3/0488* (2013.01)

(52) U.S. Cl.
CPC ......... *G06F 3/04847* (2013.01); *G16H 40/63* (2018.01); *G06F 2203/04806* (2013.01)

(56) References Cited

U.S. PATENT DOCUMENTS

| | | | |
|---|---|---|---|
| 2008/0034081 A1 | 2/2008 | Marshall et al. | |
| 2008/0243107 A1* | 10/2008 | Muhlhoff | A61B 90/03 606/4 |
| 2008/0289108 A1* | 11/2008 | Menkedick | A61G 7/018 5/610 |
| 2010/0078472 A1* | 4/2010 | Lin | G06Q 40/02 235/379 |
| 2011/0082395 A1 | 4/2011 | Burkhardt et al. | |
| 2011/0152882 A1* | 6/2011 | Wenderow | A61B 34/25 606/130 |
| 2011/0302414 A1 | 12/2011 | Logan et al. | |
| 2013/0099128 A1 | 4/2013 | Shikino et al. | |
| 2013/0139089 A1* | 5/2013 | Cho | G06F 3/0484 715/771 |
| 2013/0158344 A1* | 6/2013 | Taniguchi | A61B 1/00006 600/103 |
| 2013/0321284 A1 | 12/2013 | Bello et al. | |
| 2014/0013503 A1* | 1/2014 | Dixon | G16H 40/63 5/85.1 |
| 2014/0229852 A1 | 8/2014 | Lee | |
| 2014/0237064 A1* | 8/2014 | Lin | H04L 12/2809 709/208 |
| 2014/0258918 A1* | 9/2014 | Morishima | G06F 3/0481 715/783 |
| 2014/0323869 A1* | 10/2014 | Jin | A61B 8/465 600/459 |
| 2015/0015379 A1* | 1/2015 | Yoon | A61B 8/4427 340/12.5 |
| 2015/0033295 A1* | 1/2015 | Huster | G06Q 10/063 726/4 |
| 2015/0048942 A1* | 2/2015 | Bertagna | A43B 17/00 340/539.13 |
| 2015/0253974 A1* | 9/2015 | Young | H04N 21/4126 715/717 |
| 2015/0317068 A1 | 11/2015 | Marka et al. | |
| 2015/0367136 A1* | 12/2015 | Rondoni | G16H 40/67 607/42 |
| 2016/0021116 A1* | 1/2016 | Maguire | H04L 65/403 726/4 |
| 2016/0058641 A1* | 3/2016 | Moutafis | A47C 27/083 5/672 |
| 2016/0132046 A1* | 5/2016 | Beoughter | G06F 16/248 700/17 |
| 2018/0225432 A1 | 8/2018 | Suarez et al. | |

FOREIGN PATENT DOCUMENTS

| | | |
|---|---|---|
| EP | 1872736 A2 | 1/2008 |
| EP | 2039069 B1 | 4/2017 |
| JP | 4358861 B2 | 11/2009 |
| JP | 2013-106919 A | 6/2013 |
| JP | 2014-139722 A | 7/2014 |
| KR | 10-1095412 B1 | 12/2011 |
| KR | 10-2013-0096525 A | 8/2013 |
| KR | 10-2014-0059697 A | 5/2014 |
| KR | 10-2014-0102084 A | 8/2014 |
| KR | 10-2014-0129776 A | 11/2014 |
| KR | 10-2015-0003560 A | 1/2015 |
| WO | 2014/076141 A2 | 5/2014 |

OTHER PUBLICATIONS

Communication dated Apr. 14, 2017 issued by the Korean Intellectual Property Office in counterpart Korean Patent Application No. 10-2015-0019658.
Communication dated May 30, 2017 issued by the Korean Intellectual Property Office in counterpart Korean Patent Application No. 10-2015-0019658.
Communication dated Oct. 19, 2016 issued by the Korean Intellectual Property Office in counterpart Korean Patent Application No. 10-2015-0019658.
Communication dated Aug. 30, 2017 by the Korean Intellectual Property Office in counterpart Korean Patent Application No. 10-2017-0091023.
Communication dated Dec. 6, 2017, from the European Patent Office in counterpart European Application No. 16749379.0.
Communication dated Feb. 28, 2018, issued by the Korean Intellectual Property Office in counterpart Korean Patent Application No. 10-2017-0091023.
Communication dated Apr. 19, 2018, issued by the Korean Intellectual Property Office in counterpart Korean Patent Application No. 10-2017-0091023.
Communication dated Sep. 27, 2018 issued by the European Patent Office in Counterpart European Application No. 16 749 379.0.
Communication dated May 27, 2019, issued by the European Patent Office in counterpart European Application No. 16749379.0.
Communication dated Oct. 21, 2019, issued by the State Intellectual Property Office of P.R. China in counterpart Chinese Application No. 201680004078.8.
Communication dated Apr. 16, 2020, issued by the Korean Intellectual Property Office in counterpart Korean Application No. 10-2018-0057466.

* cited by examiner

FIG. 1
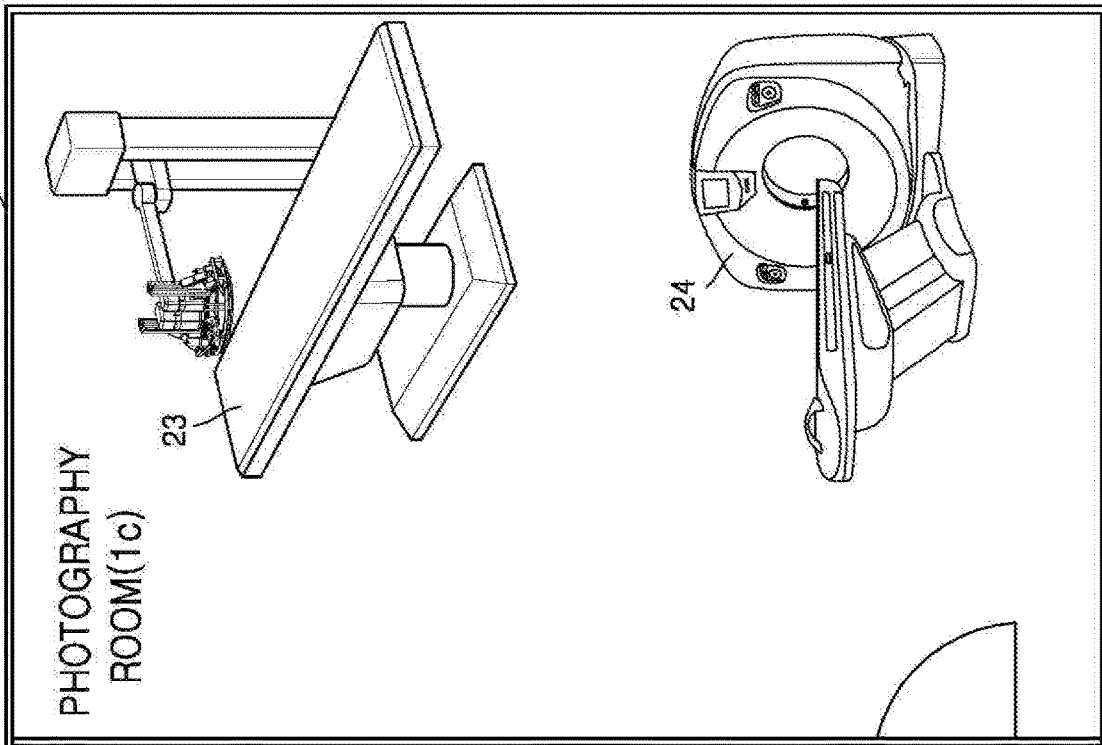
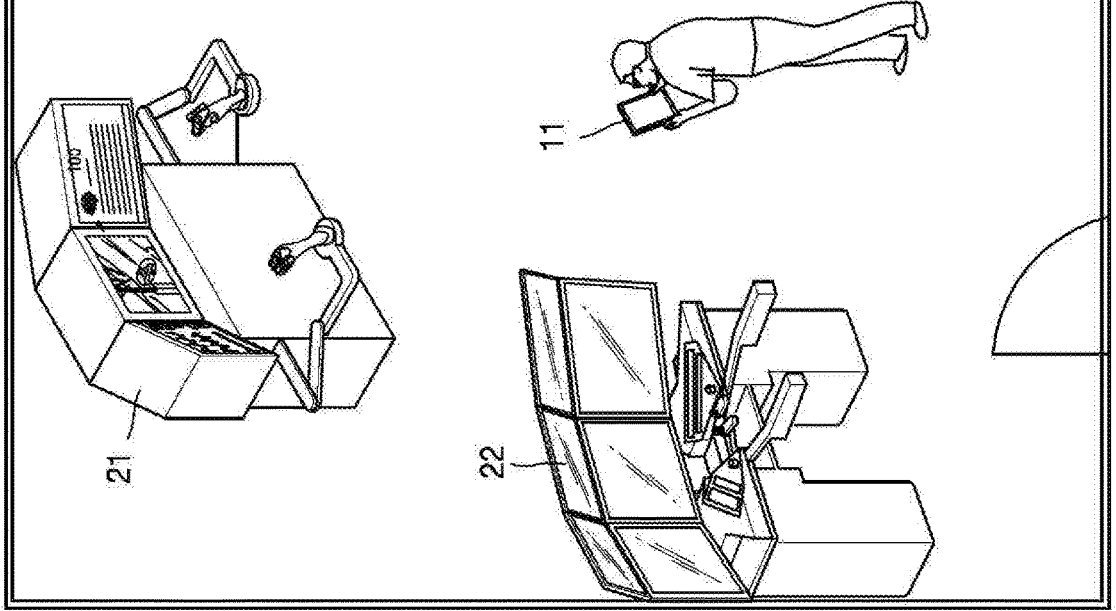

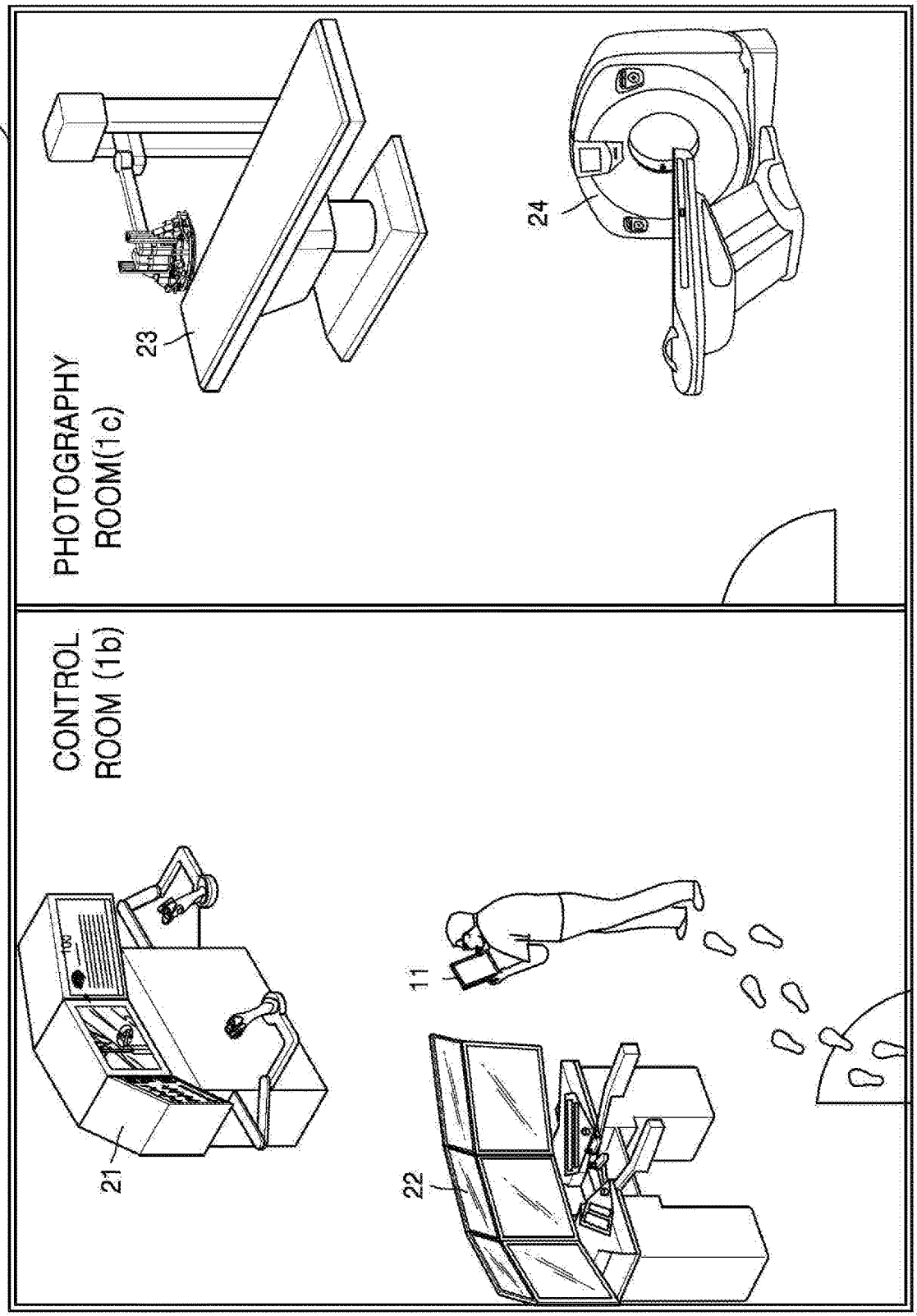

FIG. 5A
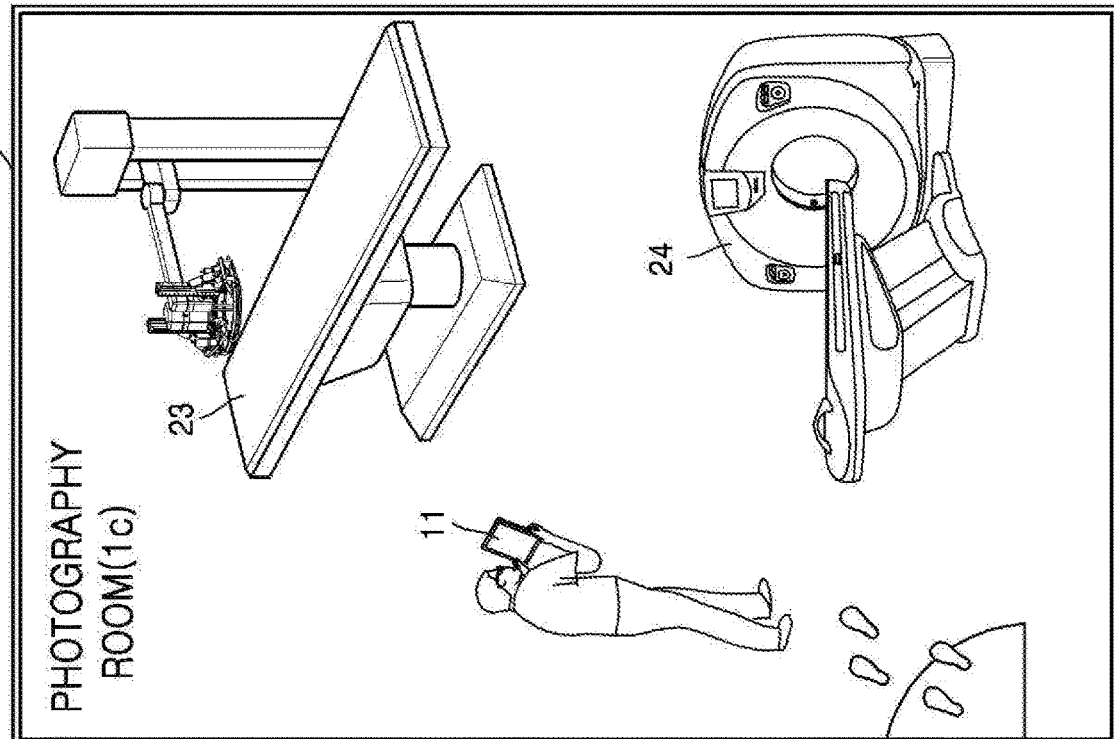
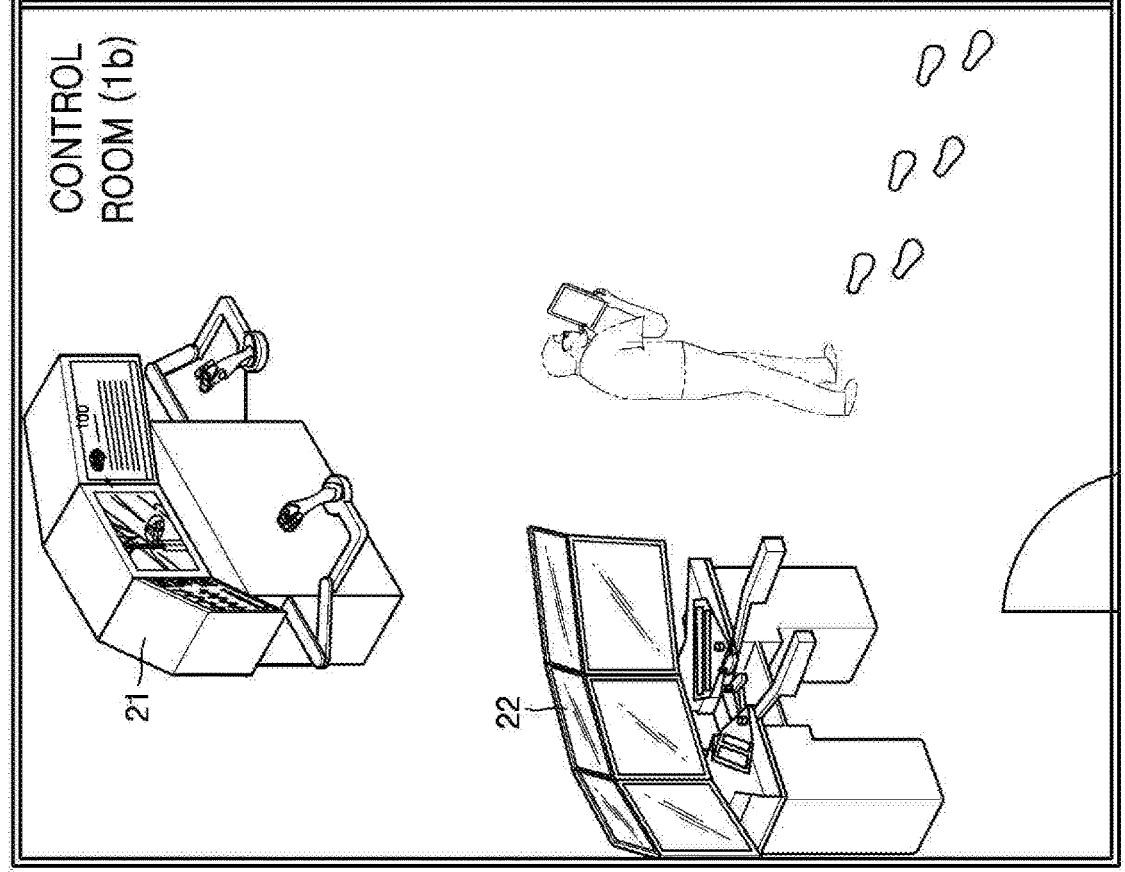

FIG. 6A
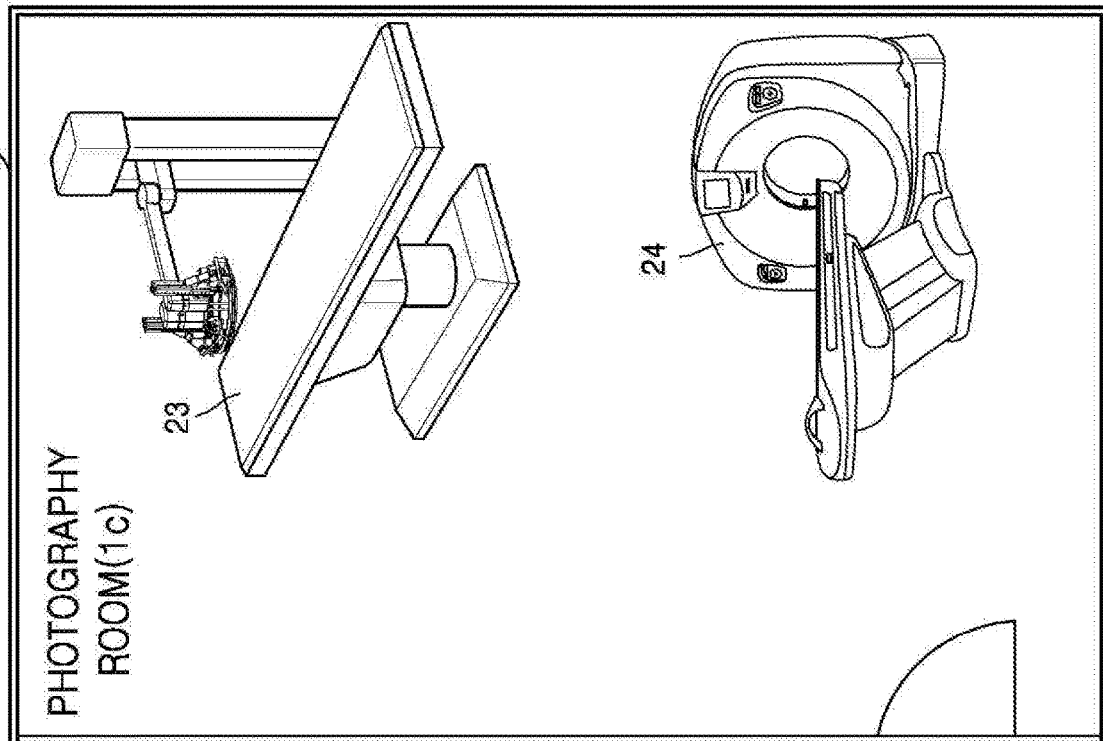
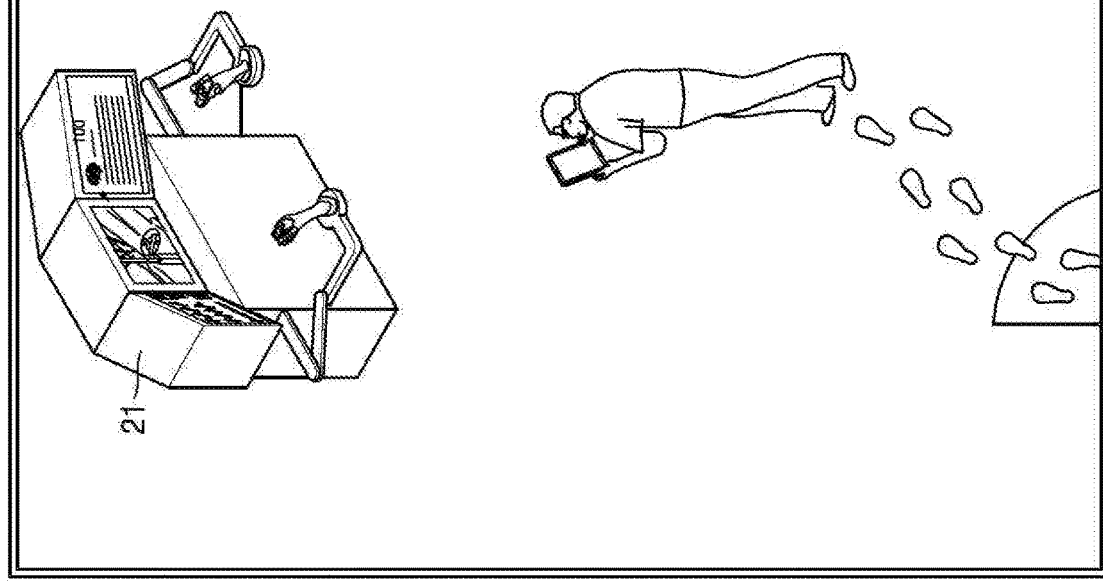

FIG. 7A
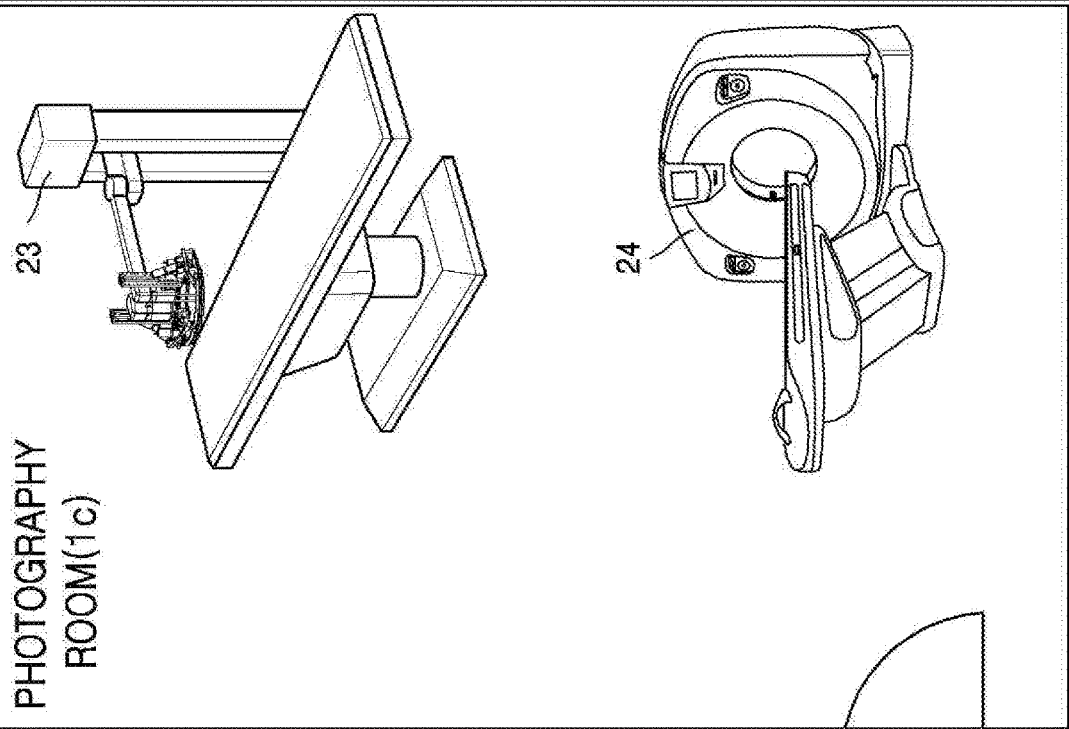
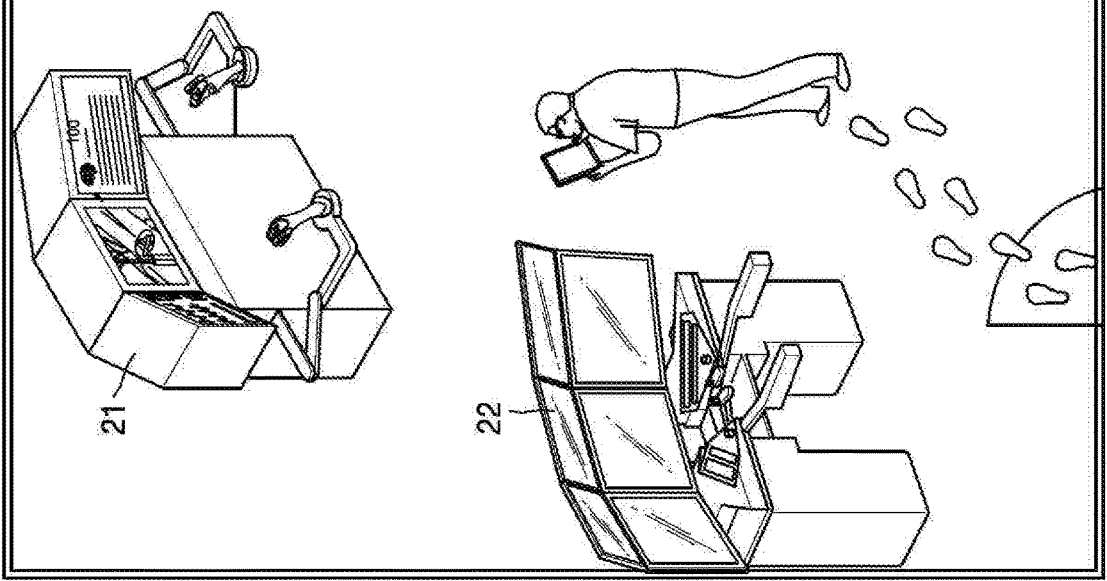

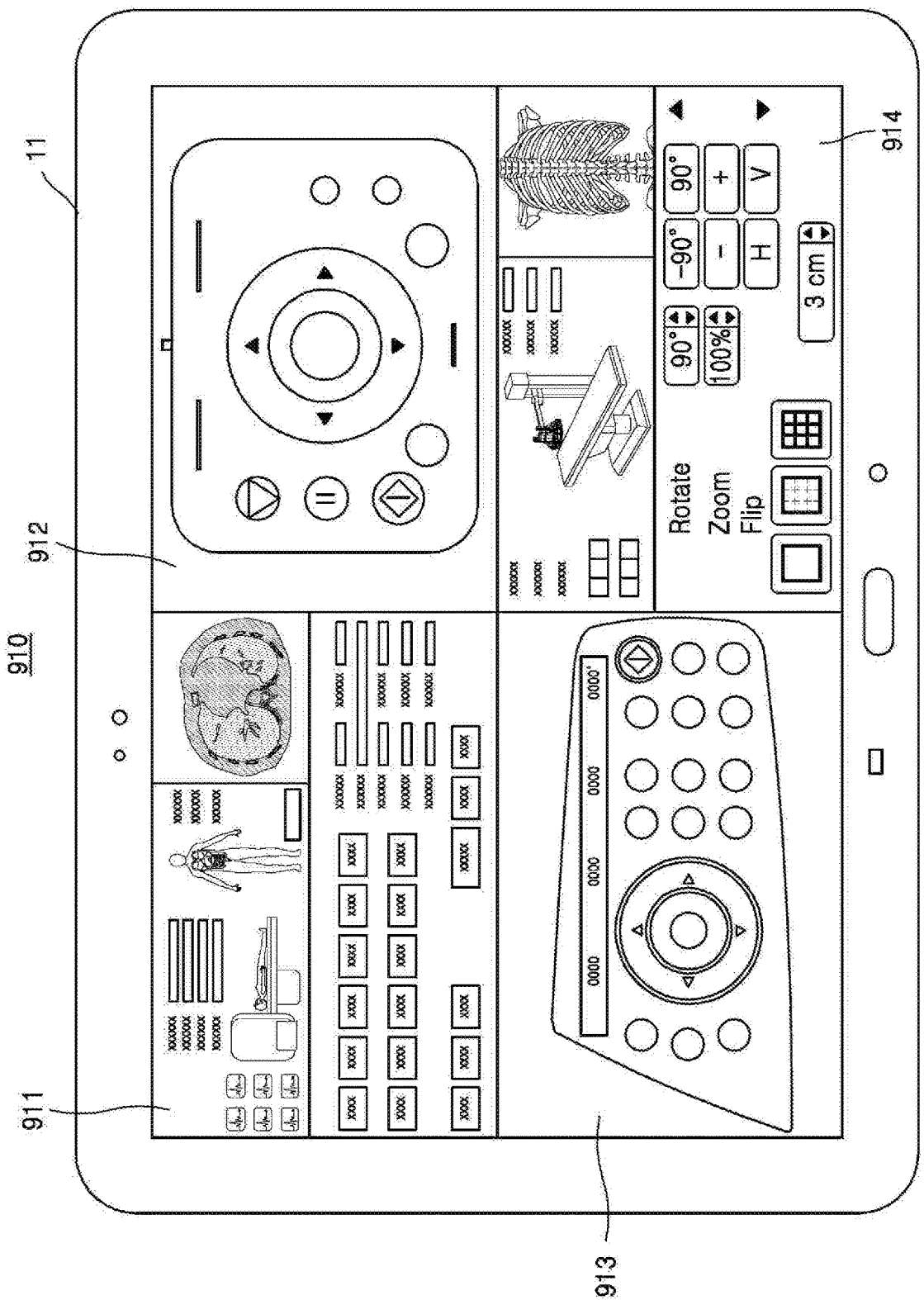

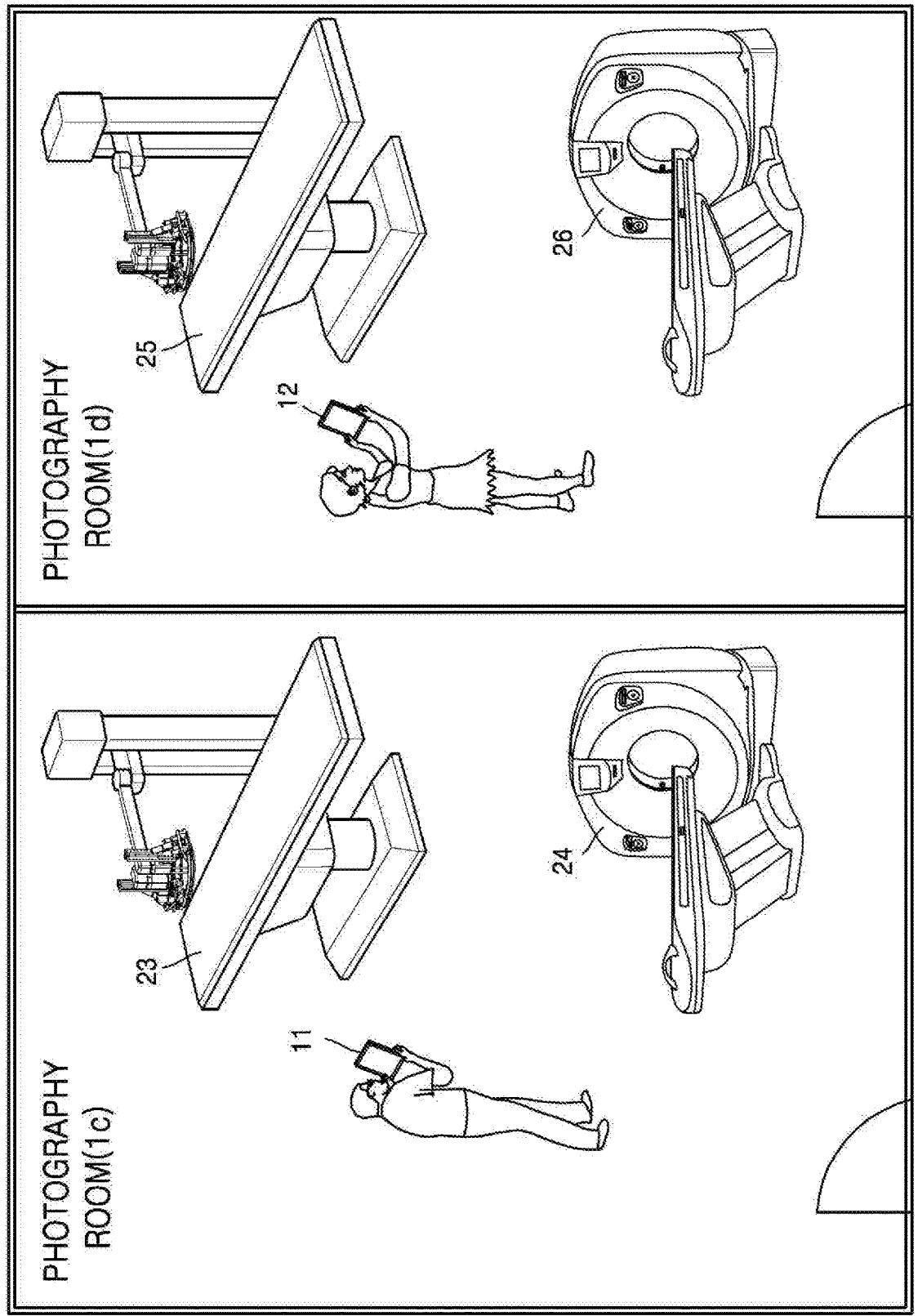

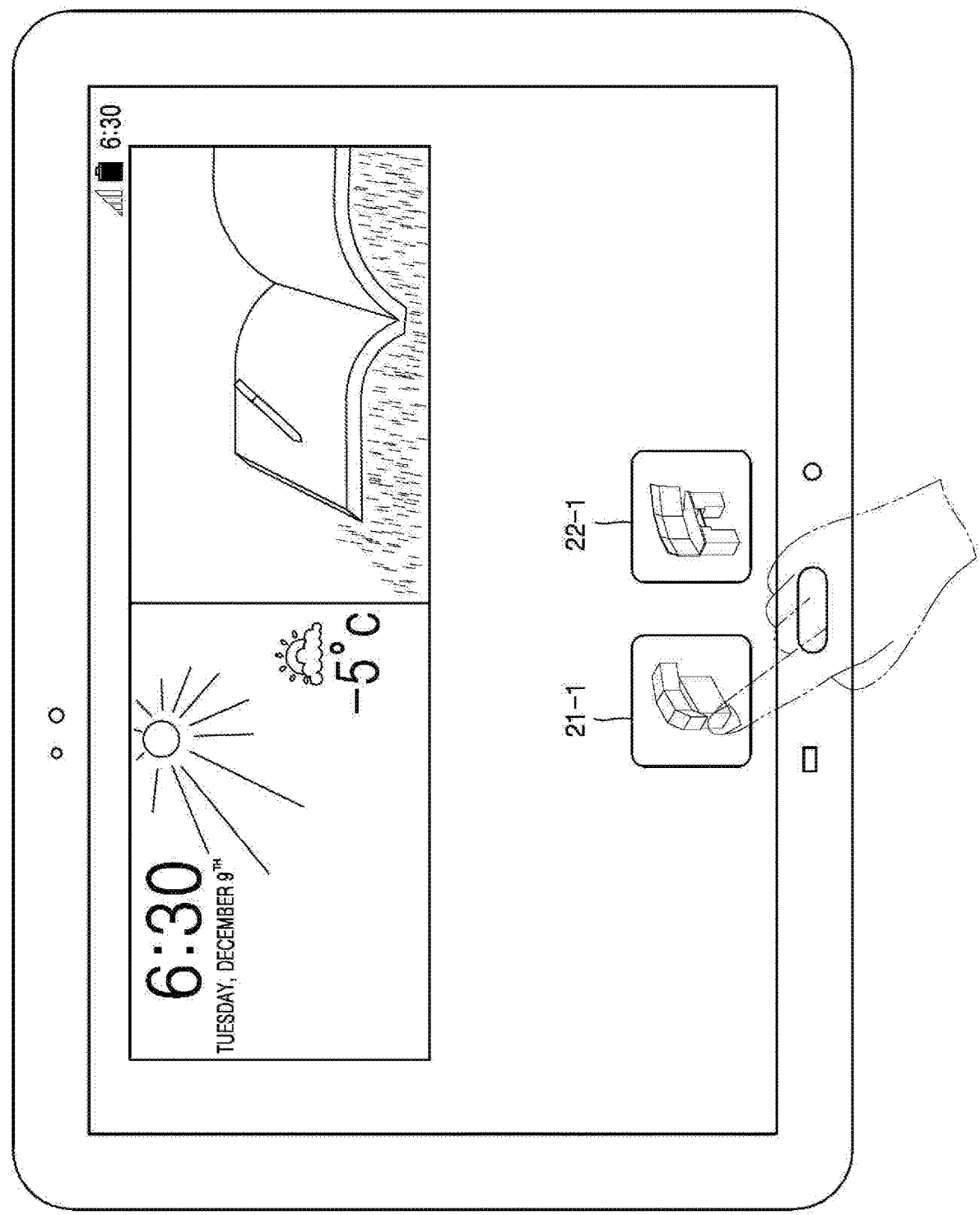

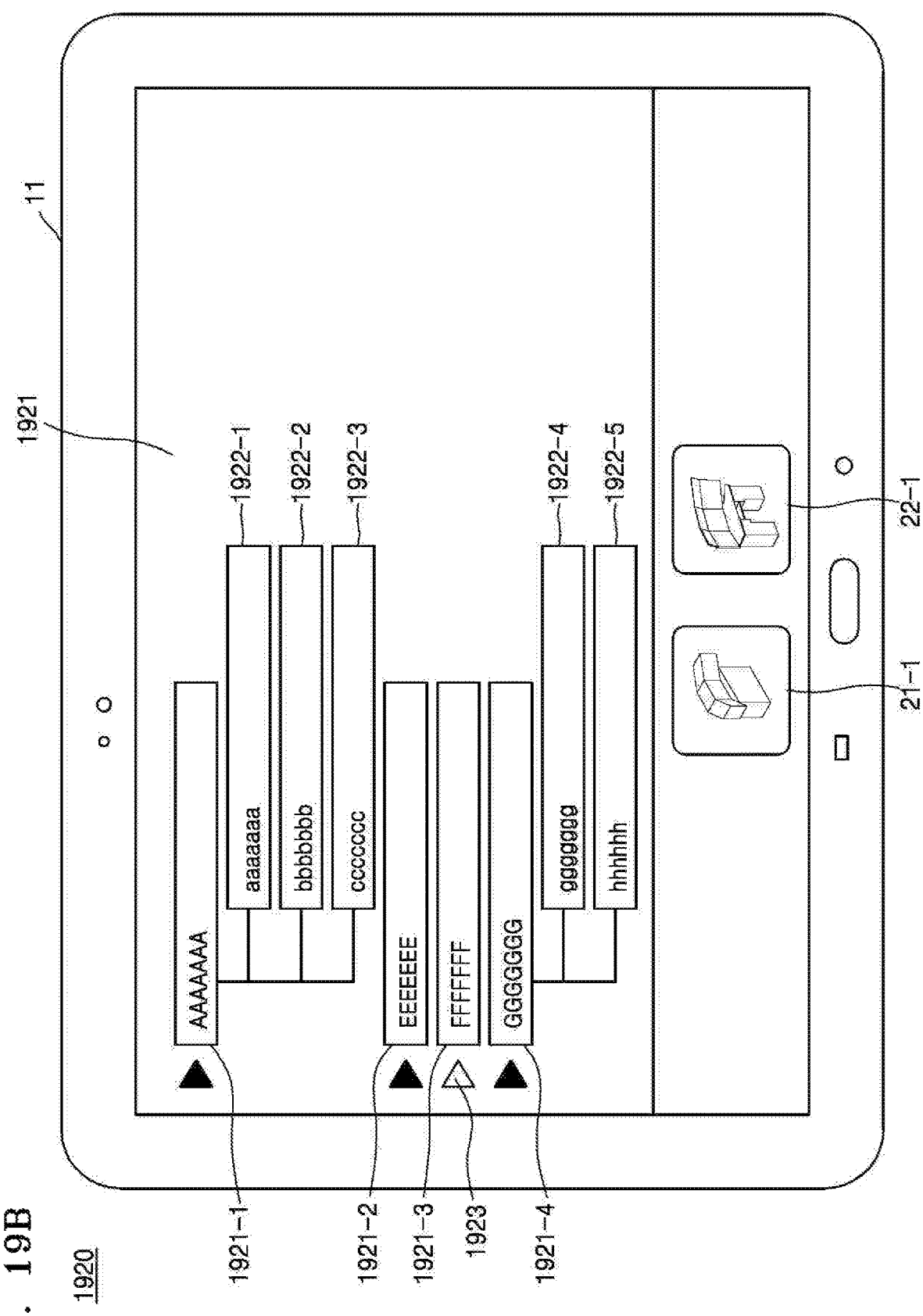

FIG. 20C
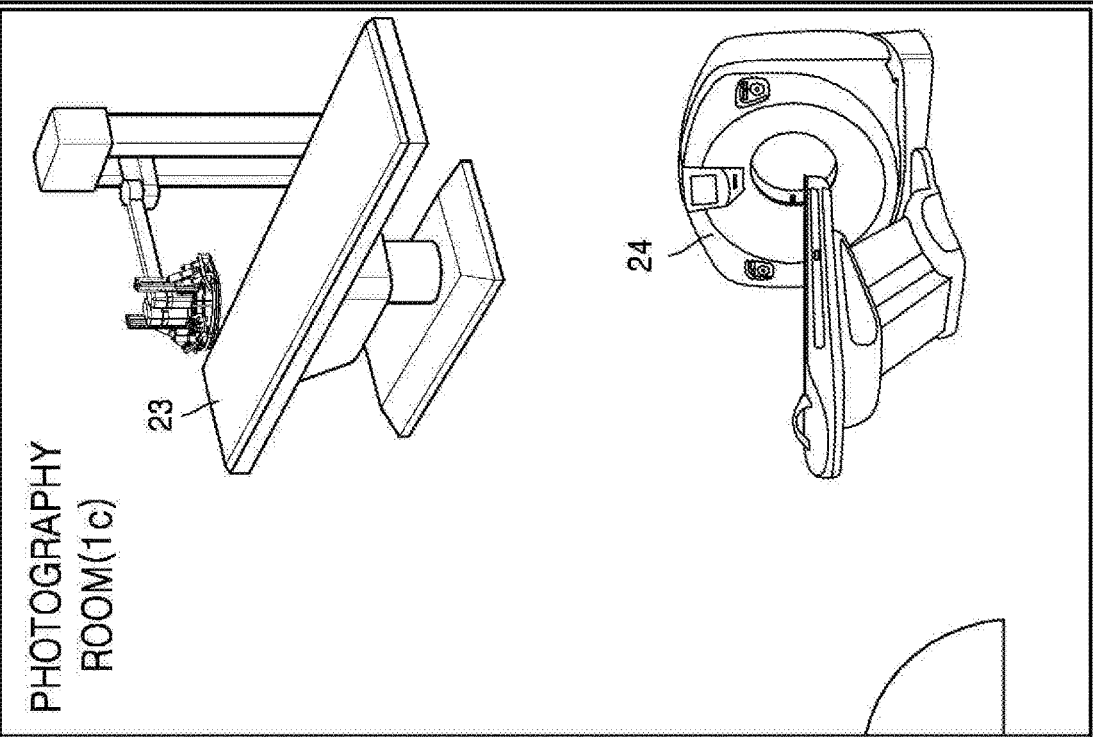
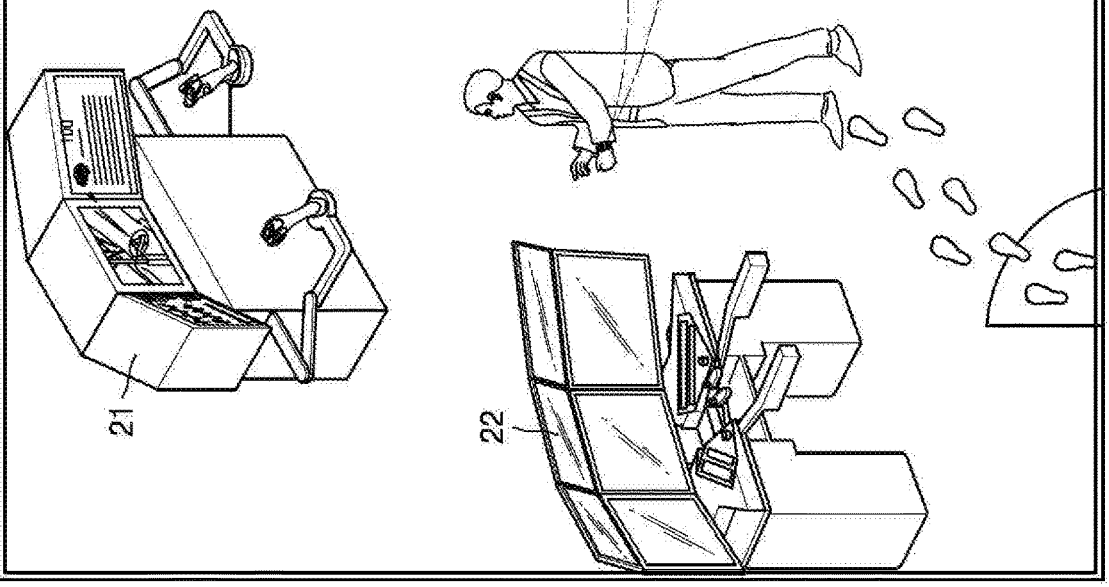

MOBILE TERMINAL AND METHOD OF CONTROLLING MEDICAL APPARATUS BY USING THE MOBILE TERMINAL

CROSS-REFERENCE TO RELATED APPLICATION

This application claims priority from Korean Patent Application No. 10-2015-0019658, filed on Feb. 9, 2015, in the Korean Intellectual Property Office, the disclosure of which is incorporated herein in its entirety by reference.

BACKGROUND

1. Field

Apparatuses and methods consistent with exemplary embodiments relate to a mobile device and a method of controlling a medical apparatus, and more particularly, to a method of controlling a medical apparatus by using a mobile terminal that includes a touch screen.

2. Description of the Related Art

In general, information may be input to medical apparatuses for capturing images of or diagnosing patients. In addition, medical apparatuses may obtain desired information by capturing images of or diagnosing patients. Examples of medical apparatuses for capturing images of or diagnosing patients may include X-ray apparatuses, ultrasound diagnosis apparatuses, computed tomography (CT) scanners, and magnetic resonance imaging (MRI) apparatuses. Examples of medical apparatuses for inputting information necessary for capturing images of or diagnosing patients may include console work stations.

A console work station is usually located in a control room. When a user (e.g., a doctor or a nurse) inputs information necessary for capturing images of a patient by using a manipulator (e.g., a console), the console work station may provide a result of the input via a viewer or a top display. The information necessary for capturing images of the patient may include, for example, an X-Ray dosage, a photography portion, a photography time, and a photography start location and a photography end location on a table.

A photographing apparatus that captures images of patients is usually located in a photography room (e.g., a shielded room) that is separate from the control room. When the user inputs information, such as a photography location, and start and end of photography, by using a manipulator (e.g., an Operator Panel Assembly (OPA) or an Operator Control Box (OCB)), the photographing apparatus may capture images of the patient.

In such situations, in order to capture images of the patient, the user has to individually manipulate the console work station in the control room and the photographing apparatus in the photography room by using different manipulators.

SUMMARY

When a user has to individually manipulate a console work station in a control room and a photographing apparatus in a photography room by using different manipulators, the user may be inconvenienced when the user captures images of a patient.

Accordingly, one or more exemplary embodiments include a mobile terminal that a user may use to intuitively and conveniently control medical apparatuses (e.g., console work stations or photographing apparatuses).

Additional aspects will be set forth in part in the description which follows and, in part, will be apparent from the description, or may be learned by practice of the presented exemplary embodiments.

According to an aspect of an exemplary embodiment, a method of controlling a medical apparatus by using a mobile terminal that includes a touch screen includes displaying, in response to determining that at least one medical apparatus is within a certain range from the mobile terminal based on location information of the at least one medical apparatus, at least one piece of identification information that corresponds to the at least one medical apparatus; detecting a user input for selecting first identification information from the at least one piece of identification information; and displaying, in response to the user input, a user interface for controlling a first medical apparatus that corresponds to the first identification information, on the touch screen.

The at least one medical apparatus may be at least one medical apparatus selected from a plurality of installed medical apparatuses that are found by a medical apparatus management server or the mobile terminal and determined to be within the certain range from the mobile terminal.

The method may further include detecting a second user input for selecting second identification information from the at least one piece of identification information; and displaying, in response to the second user input for selecting the second identification information, the user interface for controlling the first medical apparatus that corresponds to the first identification information and a user interface for controlling the second medical apparatus that corresponds to the second identification information, on the touch screen.

The displaying of the user interface for controlling the first medical apparatus may include simultaneously displaying the user interface for controlling the first medical apparatus and the at least one piece of identification information that corresponds to the at least one medical apparatus.

The displaying the at least one piece of identification information that corresponds to the at least one medical apparatus may include displaying the at least one piece of identification information on a layout based on a location where the at least one medical apparatus is installed.

A plurality of user interaction elements in the user interface may be arranged in a same order, a same direction, or both the same order and the same direction as a plurality of UI elements in a manipulator of the first medical apparatus.

The first identification information may be at least one selected from location information of the first medical apparatus, a model name of the first medical apparatus, a manufacturer of the first medical apparatus, an image of the first medical apparatus, and a shortcut icon of an application related to the first medical apparatus.

The method may further include displaying, in response to a user input that is performed via the user interface, a result of controlling the medical apparatus related to a body of a patient.

The mobile terminal may be attachable to and detachable from the first medical apparatus.

According to an aspect of an exemplary embodiment, a mobile terminal for controlling a medical apparatus includes a touch screen configured to display, in response to determining that at least one medical apparatus is within a certain range from the mobile terminal based on location information of the at least one medical apparatus, at least one piece of identification information that corresponds to the at least one medical apparatus; and a processor configured to control the touch screen to, in response to a user input for selecting first identification information from the at least one piece of identification information being detected via the touch screen, display a user interface for controlling a first medical apparatus that corresponds to the first identification information.

The at least one medical apparatus may be at least one medical apparatus selected from a plurality of installed medical apparatuses that are found in a medical apparatus management server or the mobile terminal and determined to be within the certain range from the mobile terminal.

The touch screen may detect a second user input for selecting second identification information from the at least one piece of identification information, and the processor may control the touch screen such that, in response to the second user input for selecting the second identification information, display the user interface for controlling the first medical apparatus that corresponds to the first identification information and a user interface for controlling the second medical apparatus that corresponds to the second identification information on the touch screen.

The touch screen may simultaneously display the user interface for controlling the first medical apparatus and the at least one piece of identification information that corresponds to the at least one medical apparatus.

In response to the at least one piece of identification information that corresponds to the at least one medical apparatus being displayed on the touch screen, the touch screen may display the at least one piece of identification information on a layout based on a location where the at least one medical apparatus is installed.

A plurality of user interaction (UI) elements in the user interface may be arranged in a same order, a same direction, or both the same order and the same direction as a plurality of UI elements in a manipulator of the first medical apparatus.

The first identification information may be at least one selected from location information of the first medical apparatus, a model name of the first medical apparatus, a manufacturer of the first medical apparatus, an image of the first medical apparatus, and a shortcut icon of an application related to the first medical apparatus.

In response to a user input that is performed via the user interface, the touch screen may display a result of controlling the medical apparatus related to a body of a patient.

The mobile terminal may be attachable to and detachable from the first medical apparatus.

According to an aspect of an exemplary embodiment, a non-transitory computer-readable recording medium having recorded thereon a program that performs displaying, in response to determining that at least one medical apparatus is within a certain range from the mobile terminal based on location information of the at least one medical apparatus, at least one piece of identification information that corresponds to the at least one medical apparatus, on a touch screen; detecting a user input for selecting first identification information from the at least one piece of identification information; and displaying, in response to the user input, a user interface for controlling a first medical apparatus that corresponds to the first identification information, on the touch screen.

According to an aspect of an exemplary embodiment, a non-transitory computer-readable recording medium having recorded thereon an executable program that when executed performs: in response to determining that at least one medical apparatus is within a certain range of the mobile terminal based on at least one from among location information of the at least one medical apparatus or location information of the mobile terminal, displaying at least one piece of identification information that corresponds to the at least one medical apparatus; detecting a selection of first identification information from the at least one piece of displayed identification information; and in response to the selection of first identification information, displaying a user interface for controlling a first medical apparatus that corresponds to the first identification information.

The location information may be at least one selected from among building information, room information, network information, coordinate information, distance information, orientation information, movement information, direction of movement information, and direction information of the at least one medical apparatus.

The executable program may further perform: detecting a second user input for selecting second identification information from the at least one piece of identification information; and in response to the second user input, displaying the user interface for controlling the first medical apparatus and a user interface for controlling the second medical apparatus.

The executable program may further perform: changing at least one of a plurality of user interaction (UI) elements in the user interface from an activated state to a deactivated state or from a deactivated state to an activated state, based on the location information of the at least one medical apparatus.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 is a schematic diagram of an interior of a hospital, according to an exemplary embodiment;

FIGS. 4A to 4D are diagrams of a mobile terminal displaying a user interface for controlling a medical apparatus, according to an exemplary embodiment;

FIGS. 5A to 5C are diagrams of a mobile terminal displaying a user interface for controlling a medical apparatus, according to another exemplary embodiment;

FIGS. 6A and 6B are diagrams of a mobile terminal displaying a user interface for controlling a medical apparatus, according to another exemplary embodiment;

FIGS. 7A to 7F are diagrams of a mobile terminal displaying a user interface for controlling a medical apparatus, according to another exemplary embodiment;

FIGS. 9A to 9D are diagrams of a mobile terminal displaying a user interface for controlling a medical apparatus, according to another exemplary embodiment;

FIGS. 17A to 17C are diagrams for describing using a plurality of mobile terminals to control a medical apparatus, according to an exemplary embodiment;

FIGS. 19A and 19B are diagrams of a mobile terminal displaying a user interface for controlling a medical apparatus, according to another exemplary embodiment;

FIGS. 20A to 20C are diagrams of various types of mobile terminals to which an exemplary embodiment may be applied.

DETAILED DESCRIPTION

Figure 2A:
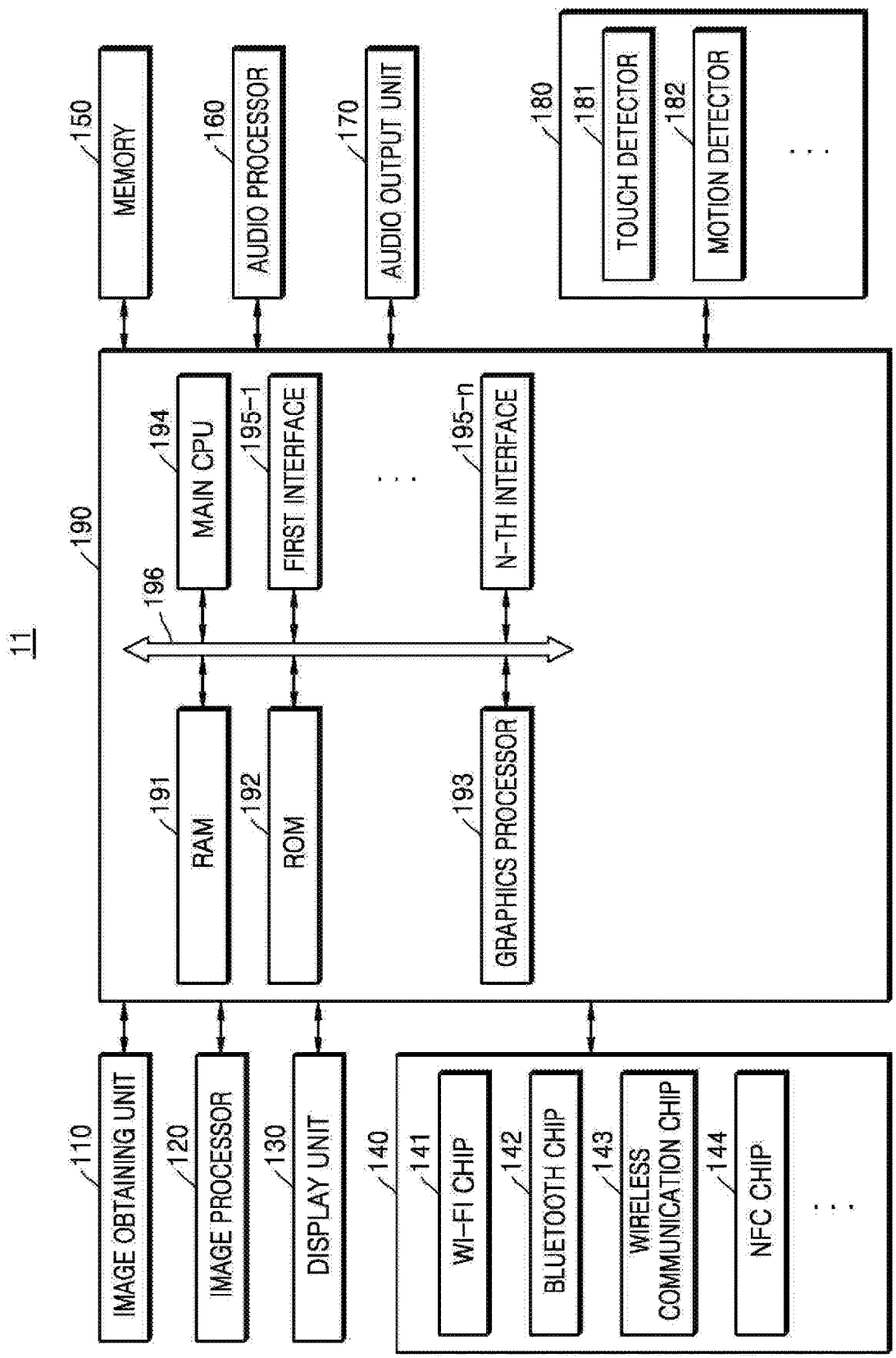
FIG. 2A is a block diagram of a mobile terminal according to an exemplary embodiment.

Terms used in the present specification will be briefly described, and then exemplary embodiments will be described in detail.

The terms used in the exemplary embodiments are selected as general terms used currently as widely as possible, but in specific cases, terms arbitrarily selected by the applicant are also used, and in such cases the meanings are mentioned in the corresponding detailed description section, so the present inventive concept should be understood not by literal meanings of the terms but by given meanings of the terms.

As the inventive concept allows for various changes and numerous exemplary embodiments, particular exemplary embodiments will be illustrated in the drawings and described in detail in the written description. However, this is not intended to limit the inventive concept to particular modes of practice, and it is to be appreciated that all changes, equivalents, and substitutes that do not depart from the spirit and technical scope are encompassed in the inventive concept. In the description, certain detailed explanations of the related art are omitted when it is deemed that they may unnecessarily obscure the essence of the inventive concept.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The terms such as "unit," "-er(-or)," and "module" described in the specification refer to an element for performing at least one function or operation, and may be implemented in hardware, software, or the combination of hardware and software. Also, except for a "module" or a "unit" that has to be implemented as a specific hardware, a plurality of "modules" or a plurality of "units" may be integrally formed as at least one module and implemented in at least one processor (not shown).

Throughout the specification, it will also be understood that when an element is referred to as being "connected to" another element, it can be directly connected to the other element, or electrically connected to the other element while intervening elements may also be present. Also, when a portion "includes" an element, another element may be further included, rather than excluding the existence of the other element, unless otherwise described.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

According to the exemplary embodiments, a user input may include, but is not limited to, at least one selected from a touch input, a bending input, a voice input, a button input, a motion input, and a multimodal input.

According to the exemplary embodiments, the "touch input" may include a touch gesture performed by a user on a display or a cover to control an apparatus. Also, the "touch input" may include an act of touching (e.g., floating or hovering) at a certain distance away from the display without touching the display. The touch input may include, but is not limited to, a touch and hold gesture, a tap gesture (touch and then release), a double-tap gesture, a panning gesture, a flick gesture, a touch-and-drag gesture (touch and then move in a direction), and a pinch gesture.

According to the exemplary embodiments, the "button input" refers to an input where the user uses a physical button on an apparatus to control the apparatus.

According to the exemplary embodiments, the "motion input" refers to a motion the user applies to an apparatus by to control the apparatus. For example, the motion input may include an input for rotating the apparatus, tilting the apparatus, or moving the apparatus up, down, left, and right.

According to the exemplary embodiments, the "multimodal input" refers to a combination of at least two input methods. For example, an apparatus may receive a touch input and a motion input of the user, or receive a touch input and a voice input of the user.

According to the exemplary embodiments, an "application" refers to a series of computer program sets devised to perform certain tasks. According to the exemplary embodiments, various types of applications may be provided. For example, game applications, video reproduction applications, map applications, memo applications, calendar applications, phone book applications, broadcasting applications, exercise support applications, payment service applications, image folder applications, medical apparatus control applications, and applications for providing a user interface of medical apparatuses.

According to the exemplary embodiments, "application identification information" may be unique information for distinguishing an application from another application. For example, identification information of an application may include, but is not limited to, an icon, an index list, a unique identification number, and link information.

According to the exemplary embodiments, a user interaction (UI) element refers to an element that may interact with the user and provide visual, auditory, and olfactory feedback according to a user input. The UI element may be shown as at least one selected from an image, a text, or a video. Alternatively, when there is an area where the above-described information is not displayed but feedback may be provided according to a user input, this area may be referred to as a UI element. Also, the UI element may be, for example, the above-described application identification information.

According to the exemplary embodiments, "UI element is deactivated" may indicate at least one selected from a user input for selecting a UI element is not processed, power of a touch sensor corresponding to a UI element is blocked, a UI element is controlled such that the UI element is not displayed, a black screen is displayed because at least a portion of power in a display that displays a UI element is blocked, or even when a UI element is selected, visual, auditory, or olfactory feedback that corresponds to the selection is not provided.

FIG. 1 is a schematic diagram of an interior 1a of a hospital, according to an exemplary embodiment;

Referring to FIG. 1, the interior 1a of the hospital may be divided into a control room 1b and a photography room (or, a shielded room) 1c. Medical apparatuses 21 and 22 (e.g., a console work station) that control photographing devices in the photography room 1c may be installed in the control room 1b. Medical apparatuses 23 and 24 (e.g., an X-ray apparatus, an ultrasound diagnosis apparatus, a computed tomography (CT) scanner, and a magnetic resonance imaging (MRI) apparatus) that capture images of patients may be installed in the photography room 1c.

"Installing a medical apparatus" may indicate that a medical apparatus is set such that information necessary for capturing images of or diagnosing patients may be input or desired information may be obtained by capturing images of or diagnosing patients, and fixed in a room. Alternatively, even when the medical apparatus is movable, once the medical apparatus is set, the medical apparatus may be fixed in the set state for a long period (e.g., 1 year or more).

In FIG. 1, when a user has a mobile terminal 11, the user may use the mobile terminal 11 in the control room 1b or move to the photography room 1c and use the mobile terminal 11. Based on a distance from the installed medical apparatuses 21 to 24 to the mobile terminal 11, a user interface for controlling the first to fourth medical apparatuses 21 to 24 may be displayed on the mobile terminal 11.

FIG. 2A is a block diagram of the mobile terminal 11 according to an exemplary embodiment.

A structure of the mobile terminal 11 shown in FIG. 2A may be applied to various types of mobile devices, for example, a smartphone, a tablet, a laptop, a personal digital assistant (PDA), an electronic frame, or a wearable device such as a wrist watch or a head-mounted display (HMD).

As shown in FIG. 2A, the mobile terminal 11 may include at least one selected from an image obtaining unit 110 (an image receiver, an image obtainer, etc.), an image processor 120, a display unit 130 (e.g., a display, etc.), a communicator 140 (e.g., a transceiver, etc.), a memory 150, an audio processor 160, an audio output unit 170 (e.g., an audio output, etc.), a detector 180 (e.g., a sensor etc.), and a processor 190 (e.g., a controller, etc.). The structure of the mobile terminal 11 shown in FIG. 2A is only an example, and exemplary embodiments are not limited thereto. Therefore, components shown in FIG. 2A may be omitted, modified, or added according to a type or a purpose of the mobile terminal 11.

The image obtaining unit 110 may obtain image data from various sources. For example, the image obtaining unit 110 may receive image data from an external server or an external device.

Also, the image obtaining unit 110 may capture an image of an external environment of the mobile terminal 11 and obtain image data. For example, the image obtaining unit 110 may be provided as a camera that captures an image of an external environment of the mobile terminal 11. In this case, the image obtaining unit 110 may include a lens (not shown) through which an image is transmitted and an image sensor (not shown) that detects the image that is transmitted through the lens. The image sensor may be provided as a charge-couples device (CCD) image sensor or a complementary metal-oxide semiconductor (CMOS) image sensor. The image processor 120 may process the image data that is obtained by the image obtaining unit 110.

The image processor 120 is a component that processes the image data that is received from the image obtaining unit 110. The image processor 120 may perform various image processing operations on the image data, such as decoding, scaling, noise filtering, frame rate conversion, and resolution conversion.

The display unit 130 displays at least one of video frames generated by processing the image data in the image processor 120 and various screens generated in a graphics processor 193.

The display unit 130 may be provided in various ways. The display unit 130 may be implemented as, for example, a liquid crystal display (LCD), an organic light-emitting diode (OLED) display, an Active-Matrix (AM) OLED display, or a plasma display panel (PDP). The display unit 130 may include additional components according to an implementation method. For example, when the display unit 130 is implemented by using a liquid crystal method, the display unit 130 may include an LCD display panel (not shown), a backlight unit (not shown) that supplies light to the LCD display panel, and a panel driver substrate (not shown) that drives a panel (not shown). The display unit 130 may be combined with a touch detector 181 of the detector 180 and thus be provided as a touch screen (200 of FIG. 2B).

The display unit 130 may be coupled to at least one of a front surface area, a side surface area, and a back surface area of the mobile terminal 11 in the form of a bent display or transparent display. A bent display may be implemented as a flexible display or a typical display that is not flexible. For example, the bent display may be provided by connecting a plurality of flat displays.

When the bent display is implemented as a flexible display, the flexible display may be a paper-thin, flexible substrate that may be curved, bent, or rolled without damage. Such flexible display may be manufactured by using not only a generally-used glass substrate but also a plastic substrate. When a plastic substrate is used, a low-temperature manufacturing processor may be used instead of an existing manufacturing processor to prevent the plastic substrate from being damaged. Alternatively, the flexible display may become flexible to be folded and unfolded by replacing a glass substrate, which covers liquid crystals in an LCD, an OLED display, an AM-OLED display, or a PDP, with a plastic film. Such flexible display is not only thin and lightweight, but also is strong against impact, may be curved or bent, and may be manufactured in various forms.

The communicator 140 establishes communication between various types of external devices by using various communication methods. The communicator 140 may include at least one selected from a Wi-Fi chip 141, a Bluetooth chip 142, a wireless communication chip 143, and a near field communication (NFC) chip 144. The processor 190 may communicate with an external server or an external device through the communicator 140.

In particular, the Wi-Fi chip 141 may communicate with the Bluetooth chip 142 by using a Wi-Fi standard and a Bluetooth standard, respectively. When the Wi-Fi chip 141 or the Bluetooth chip 142 is used, first, transmission and reception of connection information, such as a service set identifier (SSID) and session keys are performed, a communication connection is established based on the connection information, and then, transmission and reception of various pieces of information are performed. The wireless communication chip 143 may communicate by using various communication protocols such as IEEE, ZigBee, $3^{rd}$ generation (3G), 3G Partnership Project (3GPP), and Long Term Evolution (LTE). The NFC chip 144 refers to a chip that operates by using an NFC method that uses a frequency band of 13.56 MHz from among various RF-ID frequency bands such as 135 kHz, 13.56 MHz, 433 MHz, 860 MHz to 960 MHz, or 2.45 GHz.

The memory 150 may store programs and data that are necessary for operations of the mobile terminal 11. The memory 150 may be provided as a non-volatile memory, a volatile memory, a flash memory, a hard disk drive (HDD), or a solid state drive (SSD). The processor 190 may access the memory 150, and the processor 190 may read, write, edit, delete, and renew data. In the present exemplary embodiments, the term "memory" may include the memory 150, ROM (not shown) or RAM (not shown) in the processor 190, or a memory card (not shown, e.g., micro SD card or a memory stick) mounted in the mobile terminal 11. In particular, the memory 150 may store programs and data for configuring various screens that are to be displayed on a display area.

Figure 3:
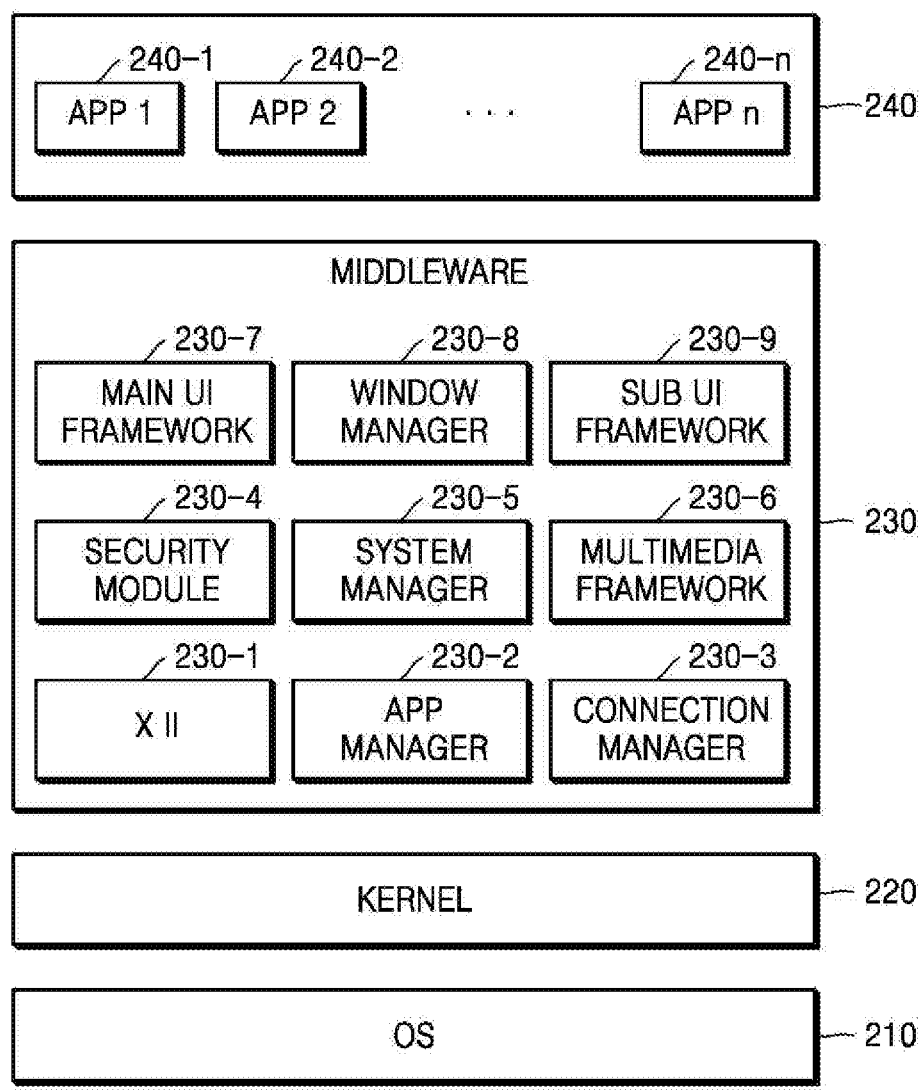
FIG. 3 is a structure of software stored in a mobile terminal, according to an exemplary embodiment.

Hereinafter, a structure of software stored in the mobile terminal 11 will be described with reference to FIG. 3. Referring to FIG. 3, software that includes an operating system (OS) 210, a kernel 220, middleware 230, and an application module 240 may be stored in the memory 150.

The OS 210 controls and manages overall operations of hardware. That is, the OS 210 is a level that is in charge of basic functions such as hardware management, storage, and security.

The kernel 220 functions as a path for transmitting signals, such as a touch signal, that are detected by the detector 180 to the middleware 230.

The middleware 230 includes various software modules that control operations of the mobile terminal 11. Referring to FIG. 3, the middleware 230 includes an X11 module 230-1, an APP manager 230-2, a connection manager 230-3, a security module 230-4, a system manager 230-5, a multimedia framework 230-6, a main UI framework 230-7, a window manager 230-8, and a sub UI framework 230-9.

The X11 module 230-1 receives various event signals from hardware units in the mobile terminal 11. Examples of an 'event' may include, for example, a user gesture detection event, a system alarm event, and a program execution or end event.

The APP manager 230-2 is a module that manages an execution state of the application module 240 that is installed in the memory 150. When an application execution event is detected by the X11 module 230-1, the APP manager 230-2 opens and executes an application that corresponds to the event.

The connection manager 230-3 is a module for supporting wired or wireless network connection. The connection manager 230-3 may include various modules such as a DNET module or a Universal Plug and Play (UPnP) module.

The security module 230-4 is a module that supports certification, permission, or security storage with respect to hardware.

The system manager 230-5 may monitor a state of each component in the mobile terminal 11 and provide a result of the monitoring to other modules. For example, if battery power is low, an error occurs, or a communication connection is disabled, the system manager 230-5 may provide a result of monitoring the above state to the main UI framework 230-7 or the sub UI framework 230-9 and output a notification message or an alarm sound.

The multimedia framework 230-6 is a module for reproducing multimedia content that is stored in the mobile terminal 11 or provided from an external source. The multimedia framework 230-6 may include a player module, a camcorder module, and a sound processing module. Accordingly, the multimedia framework 230-6 may reproduce the multimedia content and then generate and reproduce a screen and sounds.

The main UI framework 230-7 is a module for providing various user interfaces to be displayed on a main area of the display unit 130, and the sub UI framework 230-9 is a module for providing various UIs to be displayed on a sub-area of the display unit 130. The main UI framework 230-7 and the sub UI framework 230-9 may include an image composition module for configuring various UI elements, a coordinates composition module for calculating coordinates at which a UI element is to be displayed, a rendering module for rendering the configured UI element at the calculated coordinate, and a 2-dimensional (2D)/3-dimensional (3D) UI toolkit for providing a tool for configuring a 2D or 3D UI.

The window manager 230-8 may detect a touch event by using a body portion of the user or a pen, or other events. When the window manager 230-8 detects an event, the window manager 230-8 may transmit an event signal to the main UI framework 230-7 or the sub UI framework 230-9, and perform an operation that corresponds to the event.

In addition, when the user touches and drags the screen, various program modules, for example, a writing module for drawing a line along a trace of the dragging or an angle calculation module for calculating a pitch angle, a roll angle, or a yaw angle based on a sensor value that is detected by a motion detector (182 of FIG. 2A), may be stored in the mobile terminal 11.

The application module 240 includes various applications 240-1 to 240-n for supporting various functions. For example, program modules for providing various services, such as, a navigation program module, a game module, an electronic book module, a calendar module, and an alarm management module, may be included. Such applications may be installed by default, or the user may randomly install the applications. When a UI element is selected, a main CPU (194 of FIG. 2A) may execute an application that corresponds to the selected UI element by using the application module 240.

The software structure shown in FIG. 3 is an example, and exemplary embodiments are not limited thereto. Therefore, the components shown in FIG. 3 may be omitted, modified, or added according to a type or a purpose of the mobile terminal 11.

Referring back to FIG. 2A, the audio processor 160 processes audio data of image content. The audio processor 160 may perform various processing operations such as decoding, amplifying, or noise filtering of audio data. The audio data that is processed by the audio processor 160 may be output to the audio output unit 170.

The audio output unit 170 outputs not only audio data that is decoded, amplified, or noise filtered by the audio processor 160, but also various notification sounds or voice messages. In particular, the audio output unit 170 may be provided as a speaker. However, this is only an exemplary embodiment, and the audio output unit 170 may be provided as an output terminal that may output audio data.

The detector 180 detects various user interactions. The detector 180 may be formed of various sensors, and may include at least one sensing device that may detect a state change of the mobile terminal 11. For example, the detector 180 may include at least one selected from a touch sensor, an acceleration sensor, a gyro sensor, an illuminance sensor, a proximity sensor, a pressure sensor, a noise sensor (e.g., a microphone), a video sensor (e.g., a camera module), a pen sensor, and a timer.

The detector 180 may be classified as the touch detector 181, a motion detector 182, and so on according to a detection purpose, but is not limited thereto. The classification does not indicate physical classification. At least one sensor may function as the touch detector 181 and a motion detector 182. Also, according to an implementation method, components or functions of the detector 180 may be partially included in the processor 190.

For example, the touch detector 181 may detect a touch input of the user by using a touch sensor attached on a back surface of a display panel. The processor 190 may obtain information such as touch coordinates and touch time from the touch detector 181, and determine a type of the touch input (e.g., a tap gesture, a double-tap gesture, a panning gesture, a flick gesture, or a touch-and-drag gesture). Alternatively, the processor 190 may directly determine the type of the touch input by using the touch coordinates and the touch time that are obtained by the touch detector 181.

The motion detector 182 may use at least one selected from an acceleration sensor, a tilt sensor, a gyro sensor, and a 3-axis magnetic sensor to detect a motion (e.g., rotation or tilting) of the mobile terminal 11. Also, the motion detector 182 may transmit generated electric signals to the processor 190. For example, although the motion detector 182 estimates an acceleration speed by adding motion acceleration and gravity acceleration of the mobile terminal 11, if the mobile terminal 11 does not move, the motion detector 182 may only estimate gravity acceleration.

A microphone (not shown) may receive the voice of a user (e.g., start photography, pause photography, or end photography) for controlling a medical apparatus via the mobile terminal 11, and recognize the voice of the user via a user voice recognition module. Also, the microphone may transmit a recognition result to the processor 190. In this case, the user voice recognition module may not be located in the microphone, but be located in a portion of the processor 190 or outside the mobile terminal 11.

The processor 190 controls overall operations of the mobile terminal 11 by using the various programs stored in the memory 150.

The processor 190 may include RAM 191, ROM 192, the graphics processor 193, a main CPU 194, first to n-th interfaces 195-1 to 195-$n$, and a bus 196. The RAM 191, the ROM 192, the graphics processor 193, the main CPU 194, and the first to n-th interfaces 195-1 to 195-$n$ may be connected to each other via the bus 196.

The RAM 191 stores an OS and an application program. Specifically, when the mobile terminal 11 is booted, the O/S may be stored in the RAM 191, and various pieces of user-selected application data may be stored in the RAM 191.

The ROM 192 stores a set of instructions for system booting. When a turn on instruction is input to the mobile terminal 11 and thus power is supplied to the mobile terminal 11, according to instructions stored in the ROM 192, the main CPU 194 may boot a system by copying an O/S that is stored in the memory 150 to the RAM 191 and executing the O/S. When booting is finished, the main CPU 194 may copy various application programs that are stored in the memory 150 to the RAM 191, and execute the copied application programs in the RAM 191 to perform various operations.

The graphics processor 193 generates a screen that includes various objects, such as items, images, or text, by using a computing unit (not shown) and a rendering unit (not shown). The computing unit may use a control instruction that is received from the detector 180 to compute properties such as a coordinate value, a shape, a size, a color of each object according to a layout of a screen. Also, the rendering unit may generate a screen with various layouts that include objects, based on the properties computed by the computing unit. The screen generated by the rendering unit may be displayed on a display area of the display unit 130.

The main CPU 194 may access the memory 150, and perform a booting operation by using the O/S that is stored in the memory 150. Also, the main CPU 194 may perform various operations by using programs, content, and data that are stored in the memory 150.

The first to n-th interfaces 195-1 to 195-$n$ are connected to the above-described components. One of the first to n-th interfaces 195-1 to 195-$n$ may be a network interface that is connected with an external device via a network.

In particular, while pieces of identification information that correspond to medical apparatuses are displayed on the mobile terminal 11, when a user input for selecting first identification information from among the plurality of pieces of identification information is detected via a touch screen, the processor 190 may control the touch screen such that a user interface for a first medical apparatus that corresponds to the first identification information is displayed.

Figure 2B:
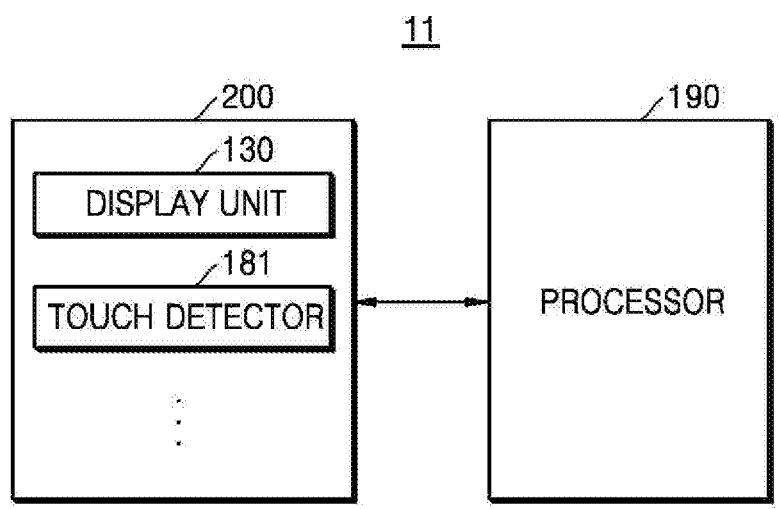
FIG. 2B is a block diagram of a mobile terminal according to another exemplary embodiment.

FIG. 2B is a block diagram of the mobile terminal 11 according to another exemplary embodiment.

Referring to FIG. 2B, the mobile terminal 11 may include the touch screen 200 and the processor 190.

The touch screen 200 may be provided as a combination of the touch detector 181 and the display unit 130.

The touch detector 181 (e.g., a touch panel) may detect a finger input of the user, and output a touch event value that corresponds to a detected touch signal. The touch panel may be mounted under the display unit 130. The touch detector 181 may detect the finger input of the user by using, for example, capacitive sensing technology and resistive sensing technology. According to the capacitive sensing technology, touch coordinates are computed by sensing subtle electricity that is generated from the body of the user. According to the resistive sensing technology, touch coordinates are computed by using two electrode plates in a touch panel to sense current that flows when upper and lower plates at a touched point contact each other.

According to another example of the mobile terminal 11, the touch screen 200 may further include a pen detector (e.g., a pen recognition panel, not shown). The pen detector may detect a pen input of the user that uses a touch pen (e.g., a stylus pen or a digitizer pen), and output a pen proximity event value or a pen touch event value. The pen detector may be an electromagnetic radiation (EMR)-type detector, and may detect a touch input or a proximity input according to electromagnetic field strength that changes when a pen approaches or touches the pen detector. In particular, the pen recognition panel may include an electron induction coil sensor with a grid structure and an electronic signal processor that sequentially provides AC signals of predetermined frequencies on each loop coil of the electron induction coil sensor. When a pen including a resonance circuit is near a loop coil of the pen recognition panel, a magnetic field transmitted from the loop coil may generate current based on mutual electron induction at the resonance circuit in the pen. Based on this current, an induction magnetic field is generated from coils that form the resonance circuit in the pen, and the pen recognition panel detects this induction magnetic field in a loop coil that is in a signal reception state. Thus, a proximity location or a touch location of the pen may be detected.

Since the example of the processor 190 is already described above, the description of the processor 190 will not be repeated.

FIGS. 4A to 4D are diagrams of the mobile terminal 11 displaying a user interface for controlling a medical apparatus, according to an exemplary embodiment;

Referring to 410 of FIG. 4A, the user carrying the mobile terminal 11 may move to the control room 1b of the interior 1a. Here, a first medical apparatus 21 and a second medical apparatus 22 may be located in the control room 1b. For example, the first medical apparatus 21 and the second medical apparatus 22 may be a first work station and a second console work station, respectively. Also, a third medical apparatus 23 and a fourth medical apparatus 24 may be located in the photography room 1c. For example, the third medical apparatus 23 and the fourth medical apparatus 24 may be an X-ray apparatus and a CT apparatus, respectively.

In this case, based on location information of the first to fourth medical apparatuses 21 to 24 of the interior 1a, the mobile terminal 11 or a medical apparatus management server (not shown) may determine the first and second medical apparatuses 21 and 22, which are located within a certain range from the mobile terminal 11, as medical apparatuses to be controlled via the mobile terminal 11. The term 'within certain range' may include at least one selected from within a certain distance, within a certain angle, within a certain height, within a certain room, within a certain building, and within a certain radius.

Specifically, the processor 190 of the mobile terminal 11 may obtain the location information of the first to fourth medical apparatuses 21 to 24 from the medical apparatus management server or the first to fourth medical apparatuses 21 to 24. Alternatively, the user may manually input the location information of the first to fourth medical apparatuses 21 to 24 so that the processor 190 may directly receive the location information of the first to fourth medical apparatuses 21 to 24. Here, the medical apparatus management server is a server that stores respective locations and unique identification information of the first and second medical apparatuses 21 and 22 or a server included in a cloud. The medical apparatus management server may store the location information of the first and second medical apparatuses 21 and 22 in advance before the mobile terminal 11 is moved into the interior 1a.

The medical apparatus management server may obtain the location information of the first to fourth medical apparatuses 21 to 24 directly from the first to fourth medical apparatuses 21 to 24 or from a manufacturer or merchandiser of the first to fourth medical apparatuses 21 to 24. Alternatively, the medical apparatus management server may receive the location information of the first to fourth medical apparatuses 21 to 24 from the user or a medical apparatus manager who manually inputs the location information of the first to fourth medical apparatuses 21 to 24. The location information of the first to fourth medical apparatuses 21 to 24 may include at least one selected from coordinate information, distance information, room information, network information, orientation information, movement information, direction of movement information, and direction information. For example, coordinate information of the first to fourth medical apparatuses 21 to 24 may be based on a coordinate system of the Global Positioning System (GPS) (e.g., World Geodetic System (WGS) 84) or Geodetic Reference System (GRS) 80. In this case, the location information of the first to fourth medical apparatuses 21 to 24 may be shown as a mathematical location using longitudes and latitudes. Alternatively, the location information of the first to fourth medical apparatuses 21 to 24 may be shown as a relative location with regard to a distance and a direction from a reference point (e.g., a base station, an access point (AP), a hub, or a mobile terminal), or a relational location according to a distance and a direction of at least one medical apparatus of which a location is known. In addition, location information may indicate whether a medical apparatus is connected to a same network as the mobile terminal 11.

Next, when the location information of the first to fourth medical apparatuses 21 to 24 is obtained, the processor 190 may use the obtained location information and search for at least one medical apparatus (21, 22) that is within a certain range from the mobile terminal 11 (e.g., within a 5 m radius from the mobile terminal 11). Alternatively, the medical apparatus management server may use the obtained location information and search for at least one medical apparatus (21, 22) that is within a certain range from the mobile terminal 11. In this case, the medical apparatus management server may provide information related to the found first and second medical apparatuses 21 and 22 to the mobile terminal 11.

After the first and second medical apparatuses 21 and 22 within a certain range from the mobile terminal 11 are found, for example, the first and second medical apparatuses 21 and 22 may be determined as medical apparatuses that are to be controlled via the mobile terminal 11.

Figure 4B:
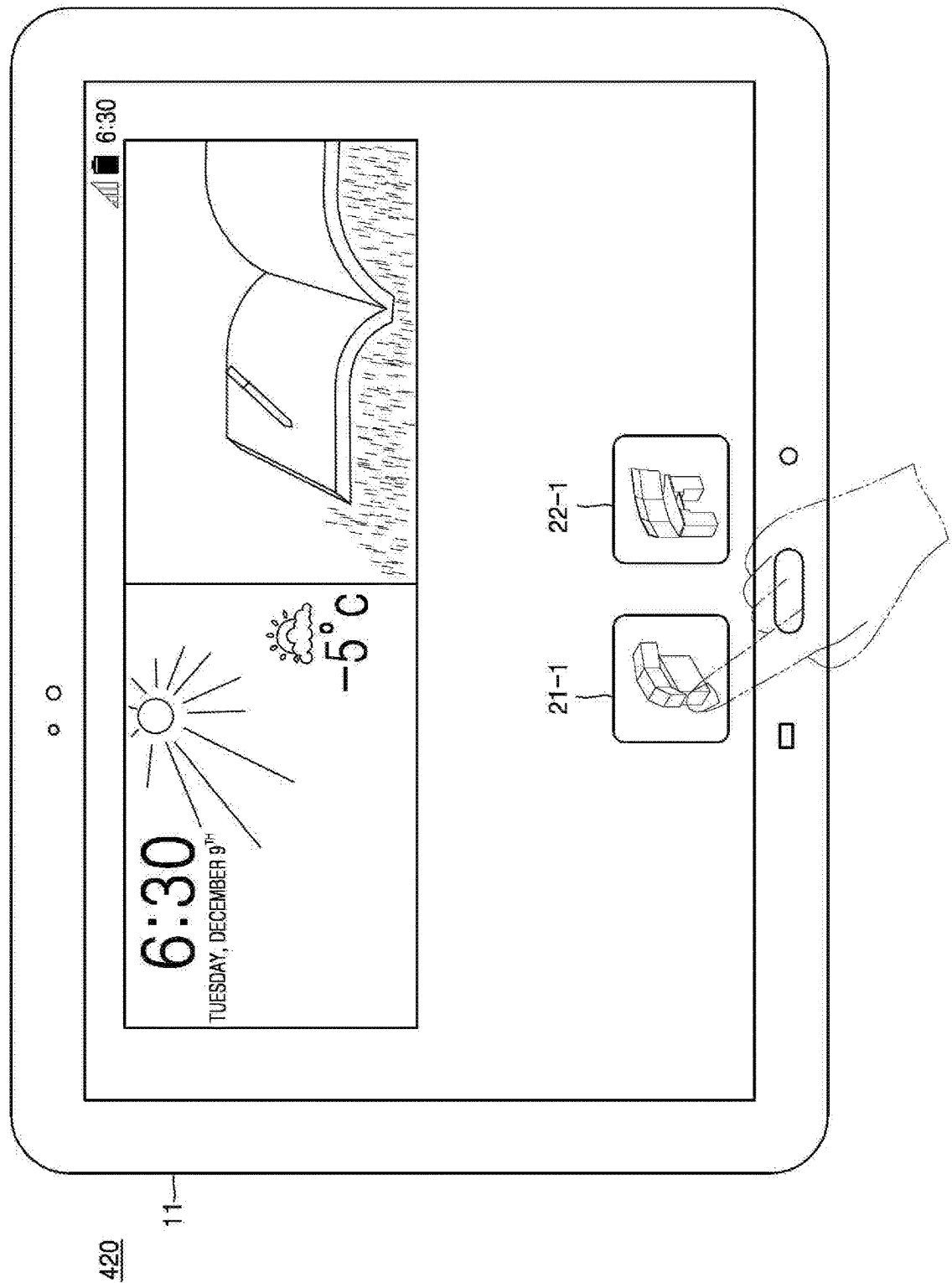

When the first and second medical apparatuses 21 and 22 are determined to be within a certain range from the mobile terminal 11, as shown in 420 FIG. 4B, the processor 190 may control the touch screen 200 such that identification information (e.g., shortcut icons) 21-1 and 22-1 that corresponds to the first and second medical apparatuses 21 and 22 are displayed. In other words, the shortcut icons may be displayed based on a location of the mobile terminal and/or locations of the medical apparatuses.

Here, when a user interface for controlling a medical apparatus is provided via an application that corresponds to the medical apparatus, identification information that corresponds to the medical apparatus may be a shortcut icon of the application. Alternatively, the identification information that corresponds to the medical apparatus may be a widget related to the application. Next, the touch screen 200 may detect a user input for selecting the identification information 21-1 that corresponds to the first medical apparatus 21 from among the identification information 21-1 and 22-1.

Figure 4C:
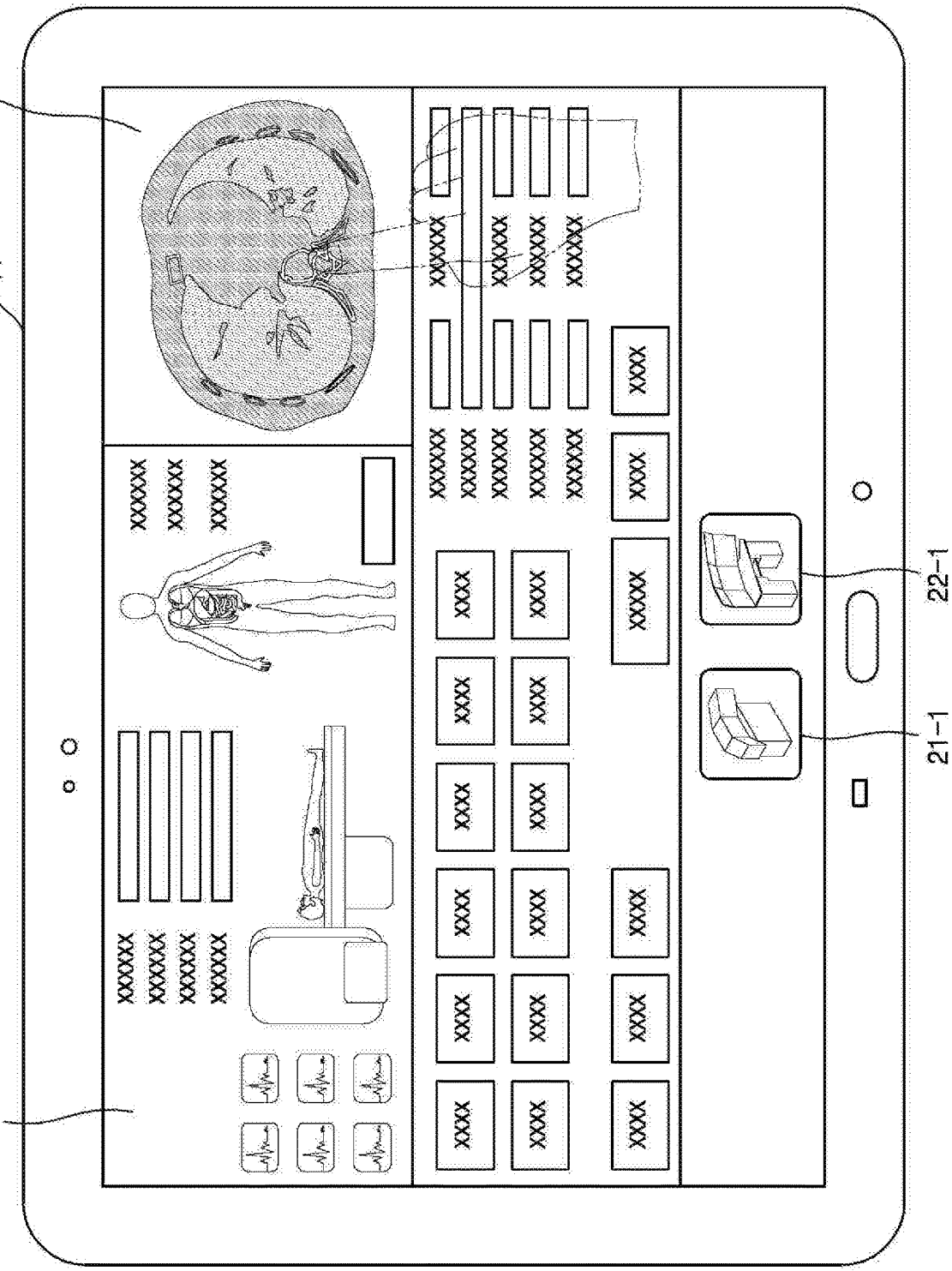

In response to the user input, as shown in 430 of FIG. 4C, the processor 190 may control the touch screen 200 such that a user interface 431 for controlling the first medical apparatus 21 that corresponds to the selected identification information is displayed. Specifically, the processor 190 may execute an application that corresponds to a selected icon, and control the touch screen 200 such that the user interface 431 for controlling the first medical apparatus 21 is displayed as an execution screen of the application.

The user interface 431 may include UI elements for controlling the first medical apparatus 21. For example, the UI elements may include at least one selected from a UI element for inputting patient information, a UI element for setting a scan parameter, a UI element for setting a scan type, a UI element for setting a scan start point and a scan end point, a UI element for starting scanning, and a UI element for finishing scanning.

In this case, the user interface 431 for controlling the first medical apparatus 21 which is displayed on the touch screen 200 may be substantially the same as or similar to an interface of a manipulator (e.g., console) of the first medical apparatus 21. For example, an arrangement order or direction of at least some UI elements in the user interface 431 may be the same as that of at least some UI elements in the manipulator of the first medical apparatus 21. In this case, even if the UI elements in the user interface 431 have different sizes or shapes than the UI elements of the manipulator of the first medical apparatus 21, the user interface 431 may be regarded as being substantially the same as the interface of the manipulator of the first medical apparatus 21.

In addition, along with the user interface 431, at least some of the identification information 21-1 and 22-1 that corresponds to the first and second medical apparatuses 21 and 22 that are within a certain range from the mobile terminal 11 may be displayed on the touch screen 200. In this case, when the touch screen 200 detects the identification information 22-1 that corresponds to the second medical apparatus 22 from among the identification information 21-1 and 22-1, the processor 190 may control the touch screen 200 such that a user interface for controlling the second medical apparatus 22 is displayed.

Next, the touch screen 200 may detect a user input for selecting a UI element 431-1 from among the UI elements in the user interface 431. The UI element 431-1 may be related to an image of a patient.

Figure 4D:
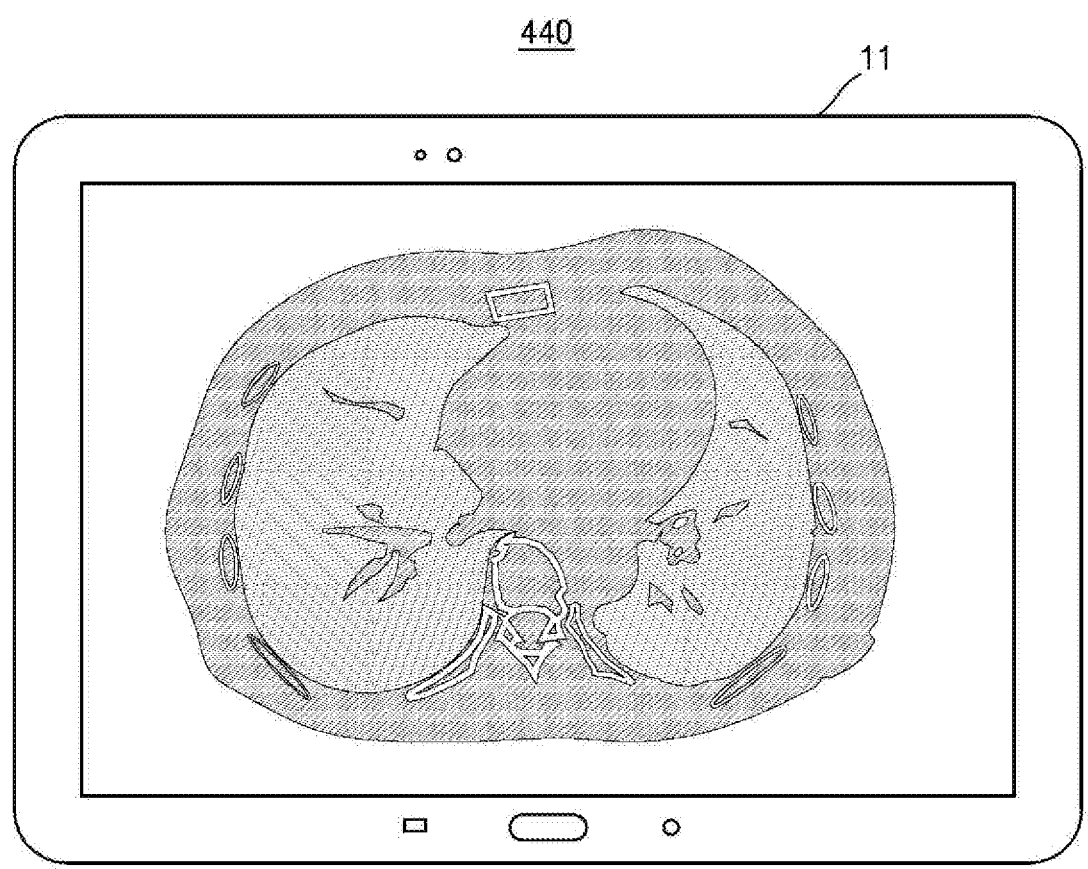

In response to the user input for selecting the UI element 431-1 shown in FIG. 4C, as shown in 440 of FIG. 4D, the processor 190 may control the touch screen 200 such that the image of the patient related to the selected UI element 431-1 is enlarged and displayed as a result of controlling the first medical apparatus 21.

As another example, the touch screen 200 may detect a user input for inputting a parameter via a UI element from among the UI elements in the user interface 431. In response to the user input, the processor 190 may control the touch screen 200 such that a diagnosis or estimation result of a patient, which is obtained by applying the parameter, is displayed as a result of controlling the first medical apparatus 21.

As described above, since the mobile terminal 11 may control both of the first and second medical apparatuses 21 and 22, the user may be able to conveniently manipulate two apparatuses instead of having to separately manipulate the apparatuses. Also, since the user may control the first and second medical apparatuses 21 and 22 in a desired location, the user does not have to inconveniently move to manipulate an apparatus.

Figure 5B:
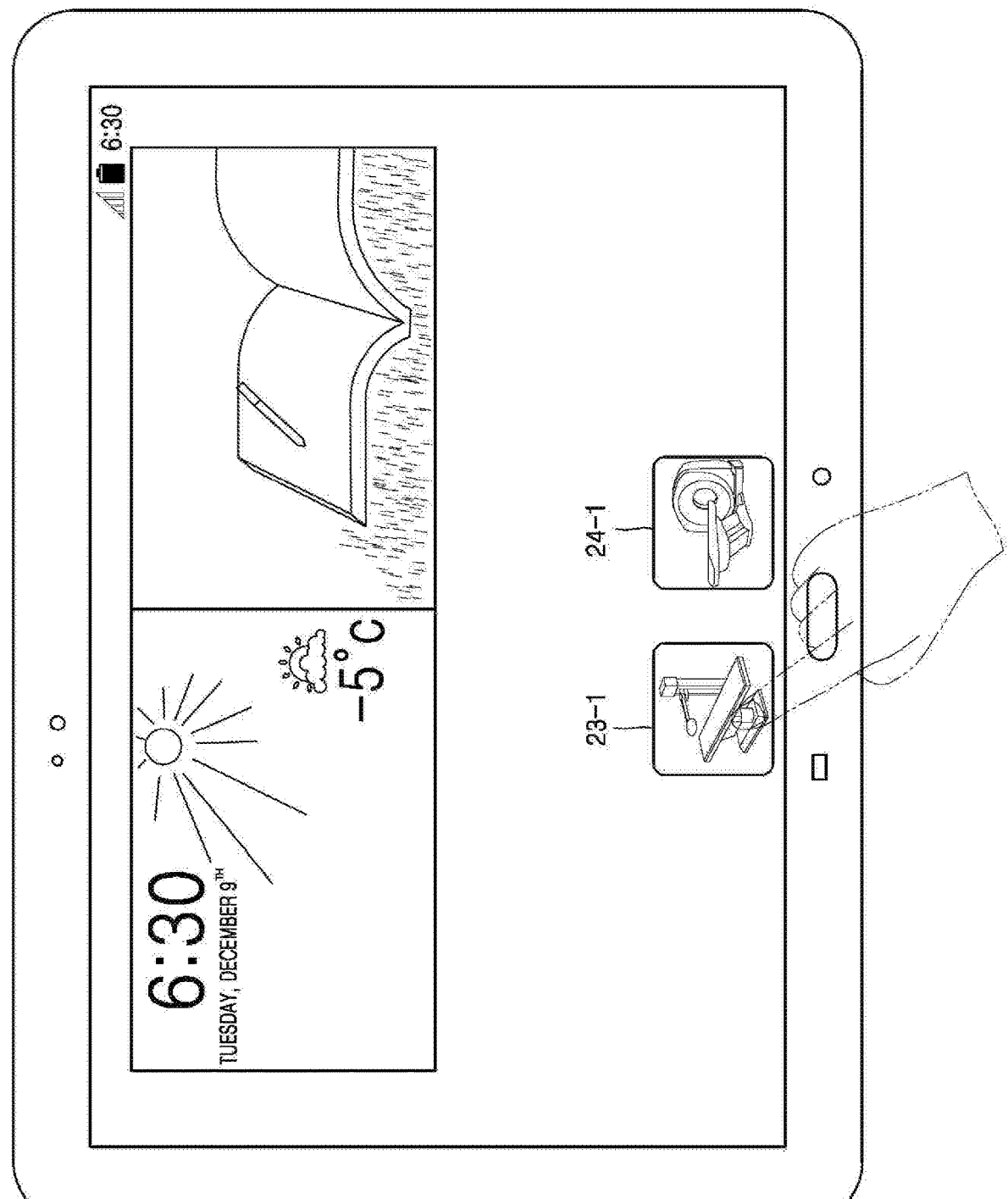
Figure 5C:
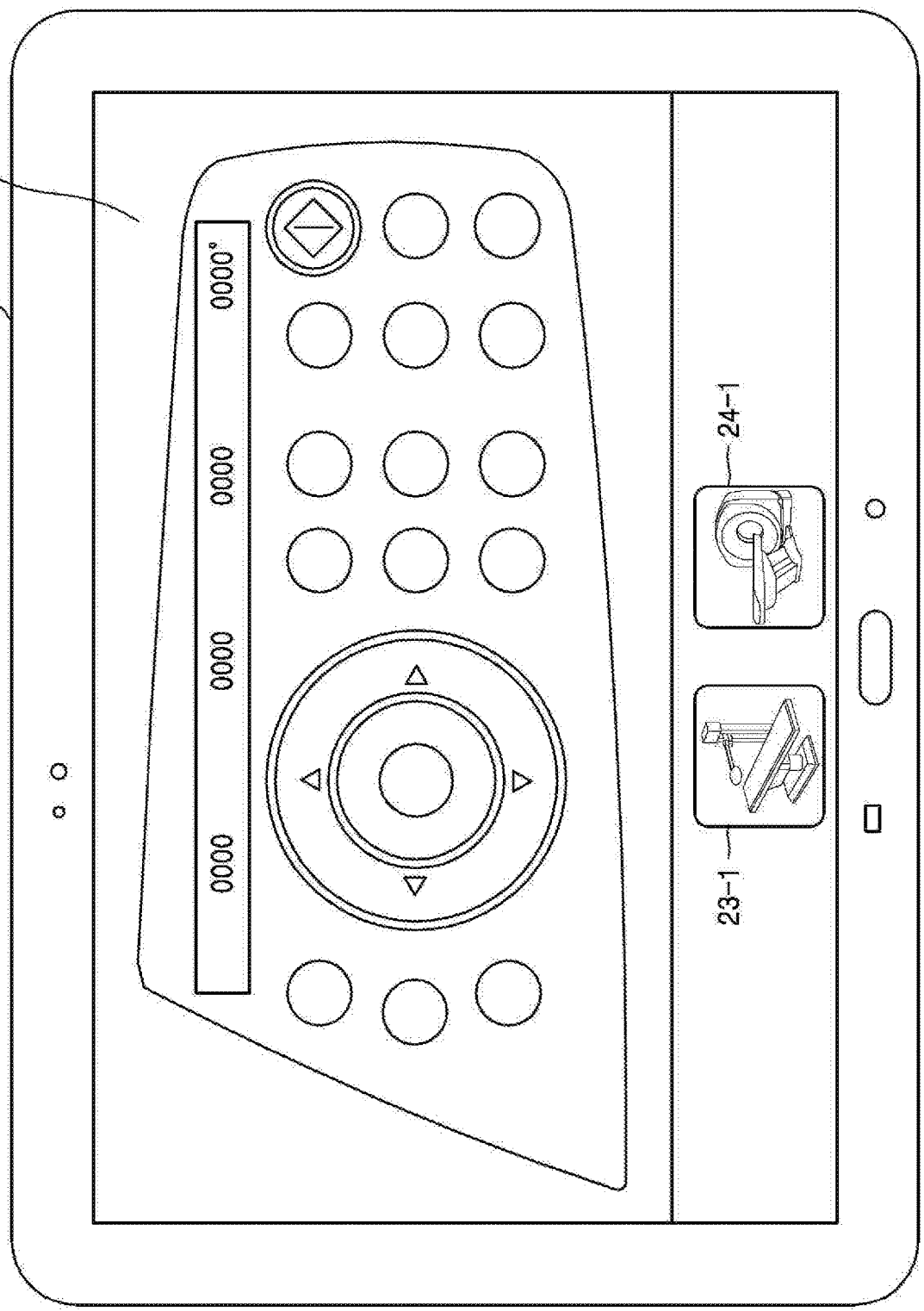

FIGS. 5A to 5C are diagrams of the mobile terminal 11 displaying a user interface for controlling a medical apparatus, according to another exemplary embodiment.

Referring to 510 of FIG. 5A, the user carrying the mobile terminal 11 may move to the photography room 1c of the interior 1a. Here, the third medical apparatus 23 and the fourth medical apparatus 24 may be located in the photography room 1c. For example, the third medical apparatus 23 and the fourth medical apparatus 24 may be an X-ray apparatus and a CT apparatus, respectively.

In this case, based on the location information of the first to fourth medical apparatuses 21 to 24 of the interior 1a, the mobile terminal 11 or the medical apparatus management server may determine medical apparatuses to be controlled via the mobile terminal 11. For example, the third medical apparatus 23 and the fourth medical apparatus 24 may be found as at least one medical apparatus within a certain range from the mobile terminal 11.

If the first to fourth medical apparatuses 21 to 24 that are located within a certain range from the mobile terminal 11 have already been found, without performing an additional process of searching for a medical apparatus, the mobile terminal 11 or the medical apparatus management server may determine at least one from among the first to fourth medical apparatuses 21 to 24 that are within a certain range from the mobile terminal 11 as a medical apparatus to be controlled via the mobile terminal 11.

When the third and fourth medical apparatuses 23 and 24 are determined as medical apparatuses within a certain range from the mobile terminal 11, as shown in 520 of FIG. 5B, the processor 190 may control the display unit 130 of the touch screen 200 such that identification information 23-1 and 24-1 that corresponds to the third and fourth medical apparatuses 23 and 24 is displayed. Next, the touch screen 200 may detect a user input for selecting the identification information 23-1 that corresponds to the third medical apparatus 23 from among the identification information 23-1 and 24-1.

In response to the user input for selecting the identification information 23-1, as shown in 530 of FIG. 5C, the processor 190 may control the touch screen 200 such that a user interface 531 for controlling the third medical apparatus 23 that corresponds to the selected identification information is displayed. The user interface 531 may include UI elements for controlling the third medical apparatus 23. For example, the UI elements may include at least one selected from a UI element for adjusting a location of a table, a UI element for turning on or off a laser, a UI element for adjusting gantry tilting, and a UI element for locking or unlocking a cradle.

In this case, the user interface 531 for controlling the third medical apparatus 23 which is displayed on the touch screen 200 may be substantially the same as or similar to an interface of a manipulator (e.g., OPA) of the third medical apparatus 23. For example, an arrangement order or direction of at least some UI elements in the user interface 531 may be the same as that of at least some UI elements in the manipulator of the third medical apparatus 23.

Also, along with the user interface 531, at least some of the identification information 23-1 and 24-1 that corresponds to the third and fourth medical apparatuses 23 and 24 that are within a certain range from the mobile terminal 11 may be displayed on the touch screen 200. Alternatively, only the identification information 24-1 that corresponds to the fourth medical apparatus 24 and the user interface 531 may be displayed on the touch screen 200.

Figure 6B:
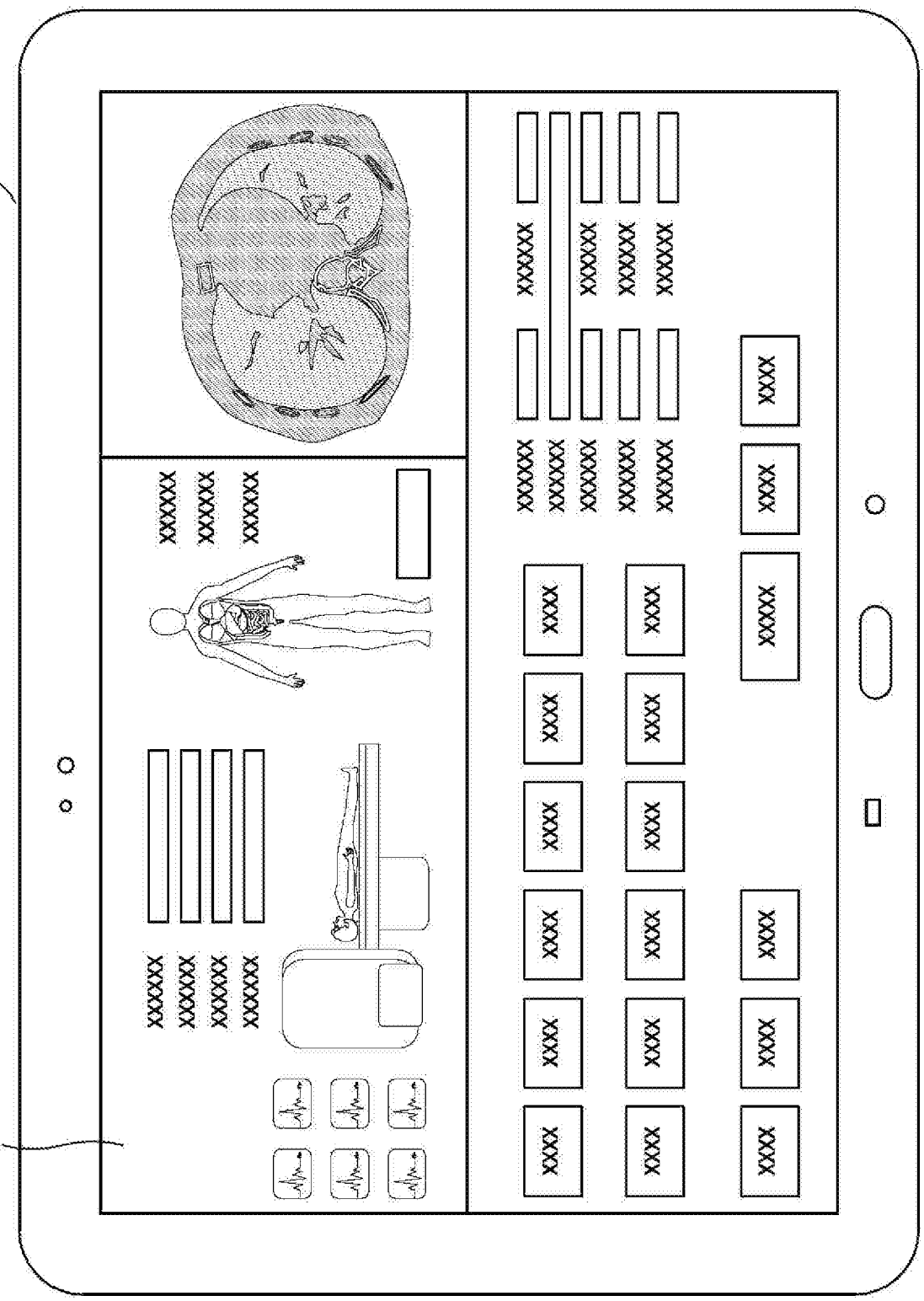

FIGS. 6A and 6B are diagrams of the mobile terminal 11 displaying a user interface for controlling a medical apparatus, according to another exemplary embodiment.

Referring to 610 of FIG. 6A, the user carrying the mobile terminal 11 may move to the control room 1b. Here, the first medical apparatus 21 may be located in the control room 1b. The first medical apparatus 21 may be, for example, a console work station. In this case, only the first medical apparatus 21 may be found as a medical apparatus that is within a certain range from the mobile terminal 11. According to an exemplary embodiment, a user interface of the closest medical apparatus to the mobile terminal may be automatically displayed.

When only the first medical apparatus 21 is found, as shown in 620 of FIG. 6B, the mobile terminal 11 may control the touch screen 200 such that a user interface 621 for controlling the first medical apparatus 21 is displayed. The user interface 621 may be automatically displayed without having to receive a user input when the first medical apparatus 21 is found. Alternatively, when notification information (e.g., an icon of a home panel or a pop-up message), which notifies that there is a medical apparatus that is found based on a movement of the user, is displayed, the user interface 621 may be displayed in response to a user input for selecting the notification information.

FIGS. 7A to 7F are diagrams of the mobile terminal 11 displaying a user interface for controlling a medical apparatus, according to another exemplary embodiment.

Referring to 710 of FIG. 7A, the user carrying the mobile terminal 11 may move to the interior 1a. In this case, the mobile terminal 11 or the medical apparatus management server may determine medical apparatuses to be controlled via the mobile terminal 11 based on the location information of the first to fourth medical apparatuses 21 to 24. The mobile terminal 11 or the medical apparatus management server may determine at least one medical apparatus that is within a certain range from the mobile terminal 11 (e.g., within a 10 m radius from the mobile terminal 11) as a medical apparatus to be controlled via the mobile terminal 11. For example, the first to fourth medical apparatuses 21 to 24 that are located within a certain range from the mobile terminal 11 (e.g., within a 10 m radius from the mobile terminal 11) as medical apparatuses to be controlled via the mobile terminal 11.

Figure 7B:
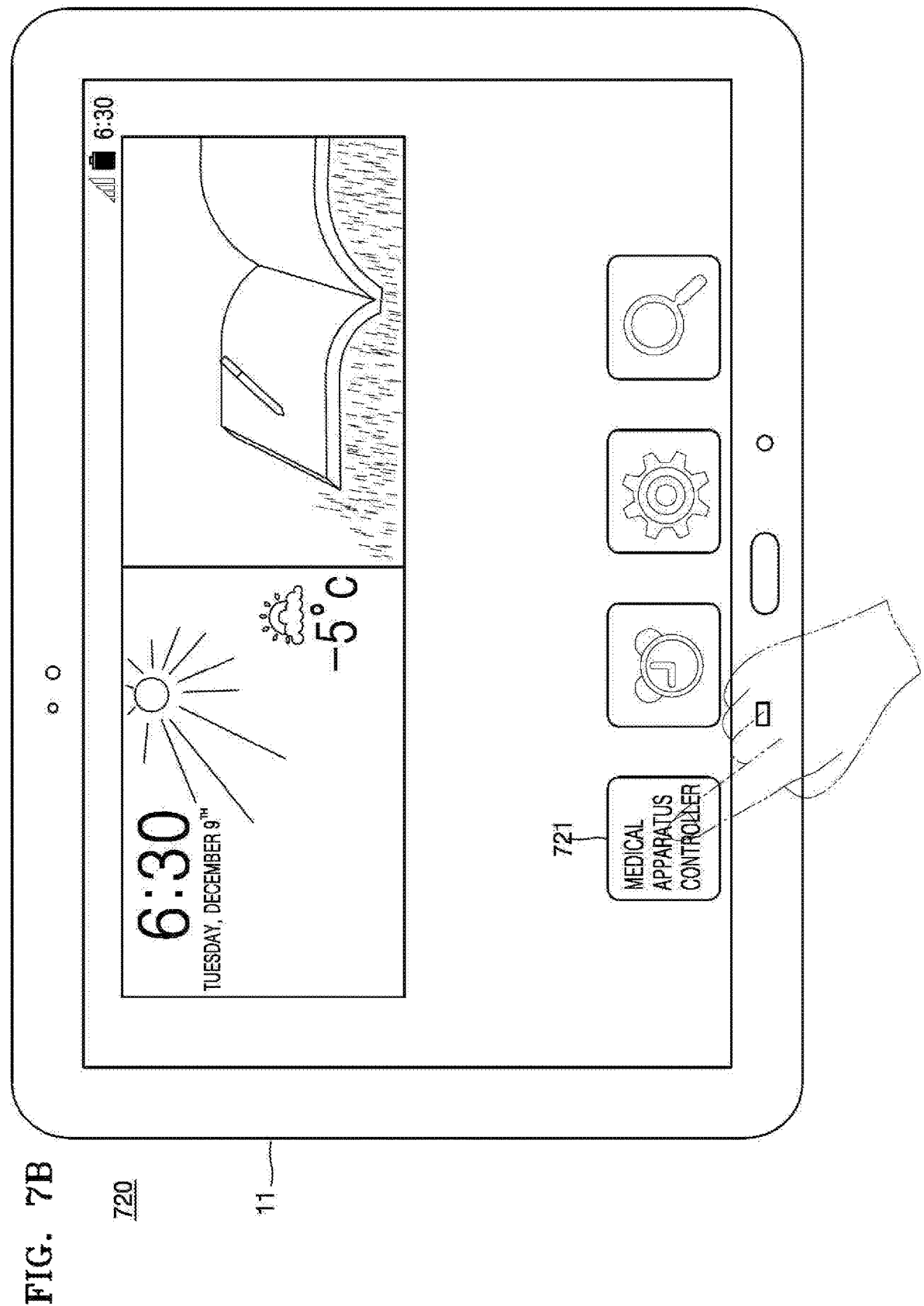

When the first to fourth medical apparatuses 21 to 24 are determined to be within a certain range from the mobile terminal 11, as shown in 720 of FIG. 7B, the touch screen 200 may detect a user input for selecting identification information (e.g., an icon) 721 of a medical apparatus control application.

Figure 7C:
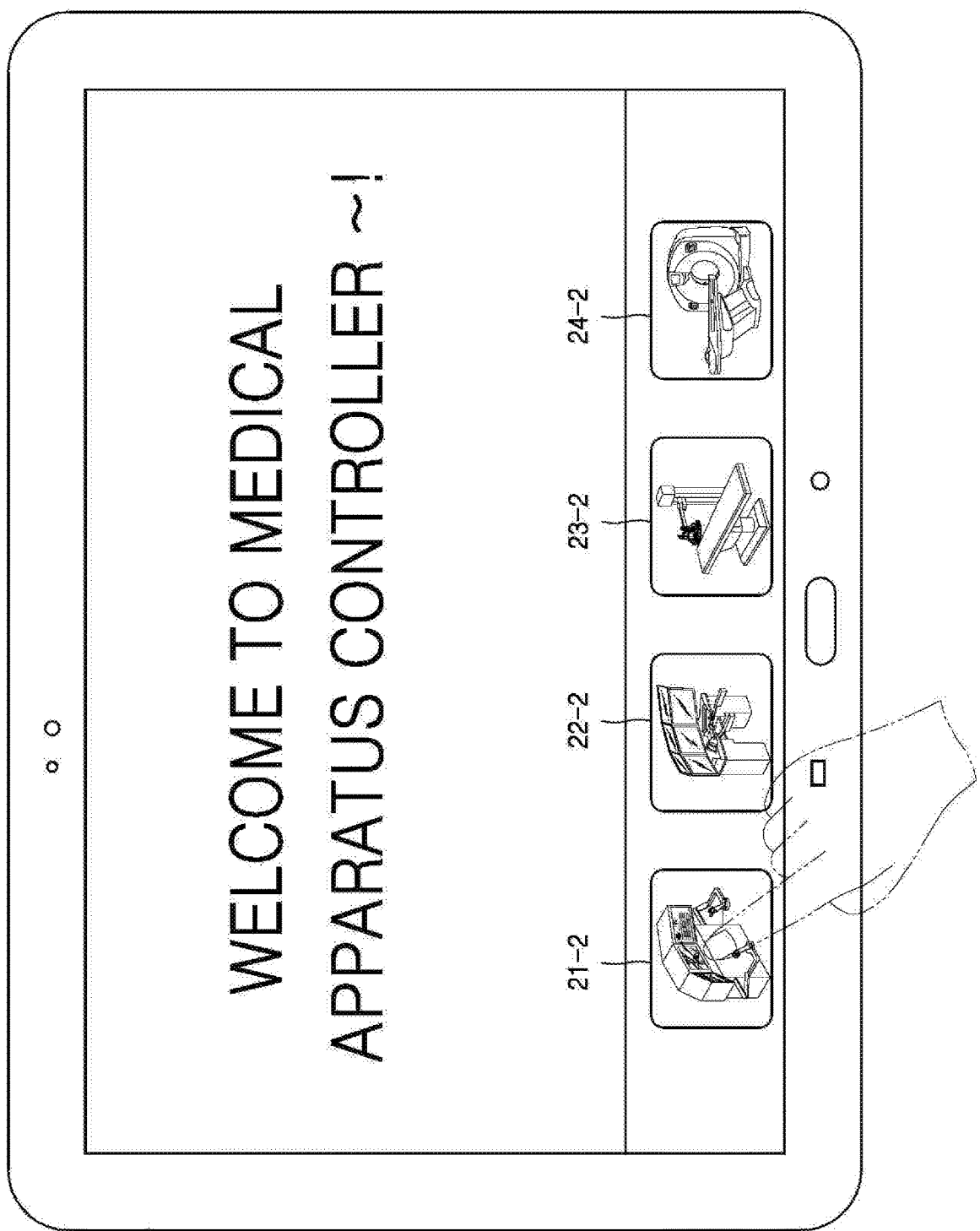

In response to the user input for selecting the identification information 721, as shown in 730 of FIG. 7C, the processor 190 may execute the medical apparatus control application, and control the touch screen 200 such that identification information (e.g., images or text icons) 21-2 to 24-2 that corresponds to the first to fourth medical apparatuses 21 to 24 is displayed. According to another exemplary embodiment, the first to fourth medical apparatuses 21 to 24 that are located within a certain range from the mobile terminal 11 may be determined after the medical apparatus control application is executed.

Next, the touch screen 200 may detect a user input for selecting the identification information 21-2 that corresponds to the first medical apparatus 21 from among the identification information 21-2 to 24-2.

Figure 7D:
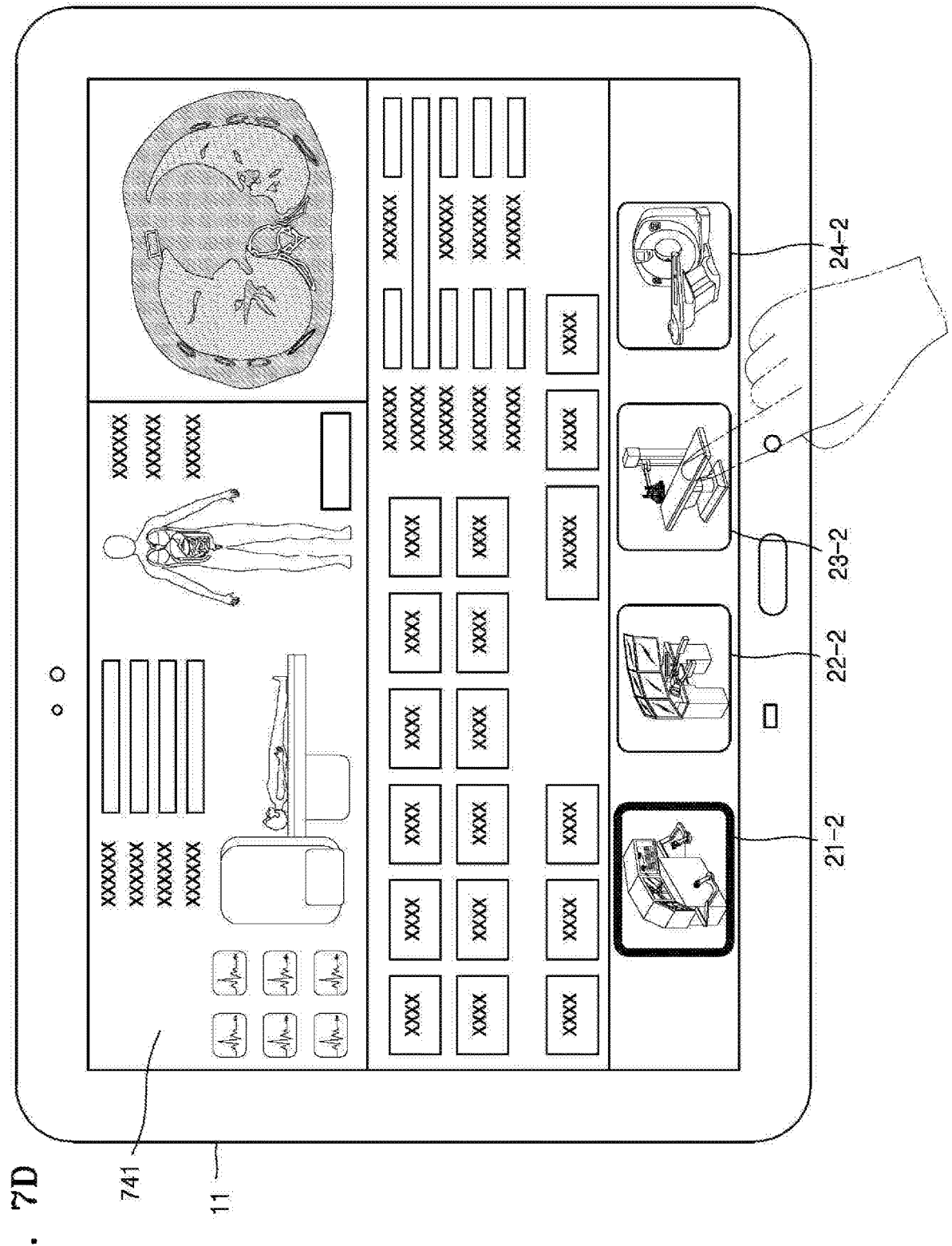

In response to the user input for selecting the identification information 21-2, as shown in 740 of FIG. 7D, the processor 190 may control the touch screen 200 such that a user interface 741 for controlling the first medical apparatus 21 that corresponds to the selected identification information 21-2 is displayed. Here, along with the user interface 741, the identification information 21-2 to 24-2 that corresponds to the first to fourth medical apparatuses 21 to 24 that are within a certain range from the mobile terminal 11 may be displayed. As shown in FIG. 7D, the identification information 21-2 that corresponds to the first medical apparatus 21 may be highlighted and thus distinguished from the identification information 22-2 to 24-2.

Next, the touch screen 200 may detect a user input for selecting the identification information 23-2 that corresponds to the third medical apparatus 23 from among the identification information 21-2 to 24-2.

Alternatively, the touch screen 200 may detect a user input for performing a touch-and-drag gesture or a swipe gesture in a direction until a user interface for controlling the third medical apparatus 23 is displayed on the user interface 741 that is currently displayed on the touch screen 200.

Figure 7E:
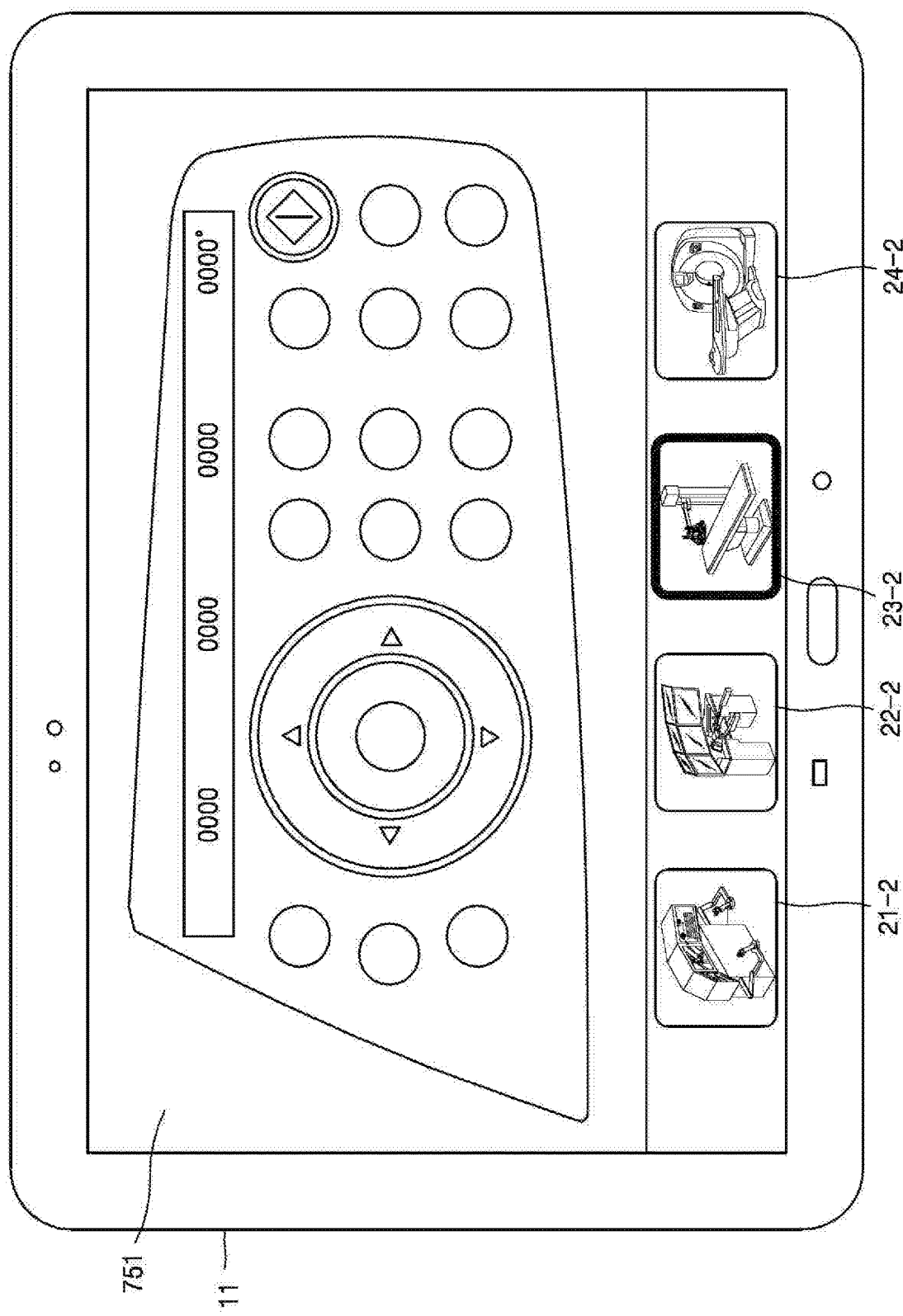

In response to the user input, as shown in 750 of FIG. 7E, the processor 190 may control the touch screen 200 such that a user interface 751 for controlling the third medical apparatus 23 is displayed. Here, the identification information 21-2 to 24-2 that corresponds to the first to fourth medical apparatuses 21 to 24 that are within a certain range from the mobile terminal 11 may be displayed along with the user interface 751, and the identification information 23-2 that corresponds to the third medical apparatus 23 may be highlighted.

According to another exemplary embodiment, in a state in which the identification information (e.g., images or text icons) 21-2 to 24-2 that corresponds to the first to fourth medical apparatuses 21 to 24 is displayed, as shown in 730 of FIG. 7C, the processor 190 may detect a user input for selecting the identification information 21-2 that corresponds to the first medical apparatus 21 and the identification information 23-2 that corresponds to the third medical apparatus 23. The user input may be a multi-touch input that simultaneously touches the identification information 21-2 and 23-2, or, a touch input that sequentially touches the identification information 21-2 and 23-2 within a predetermined time (e.g., within a second).

Figure 7F:
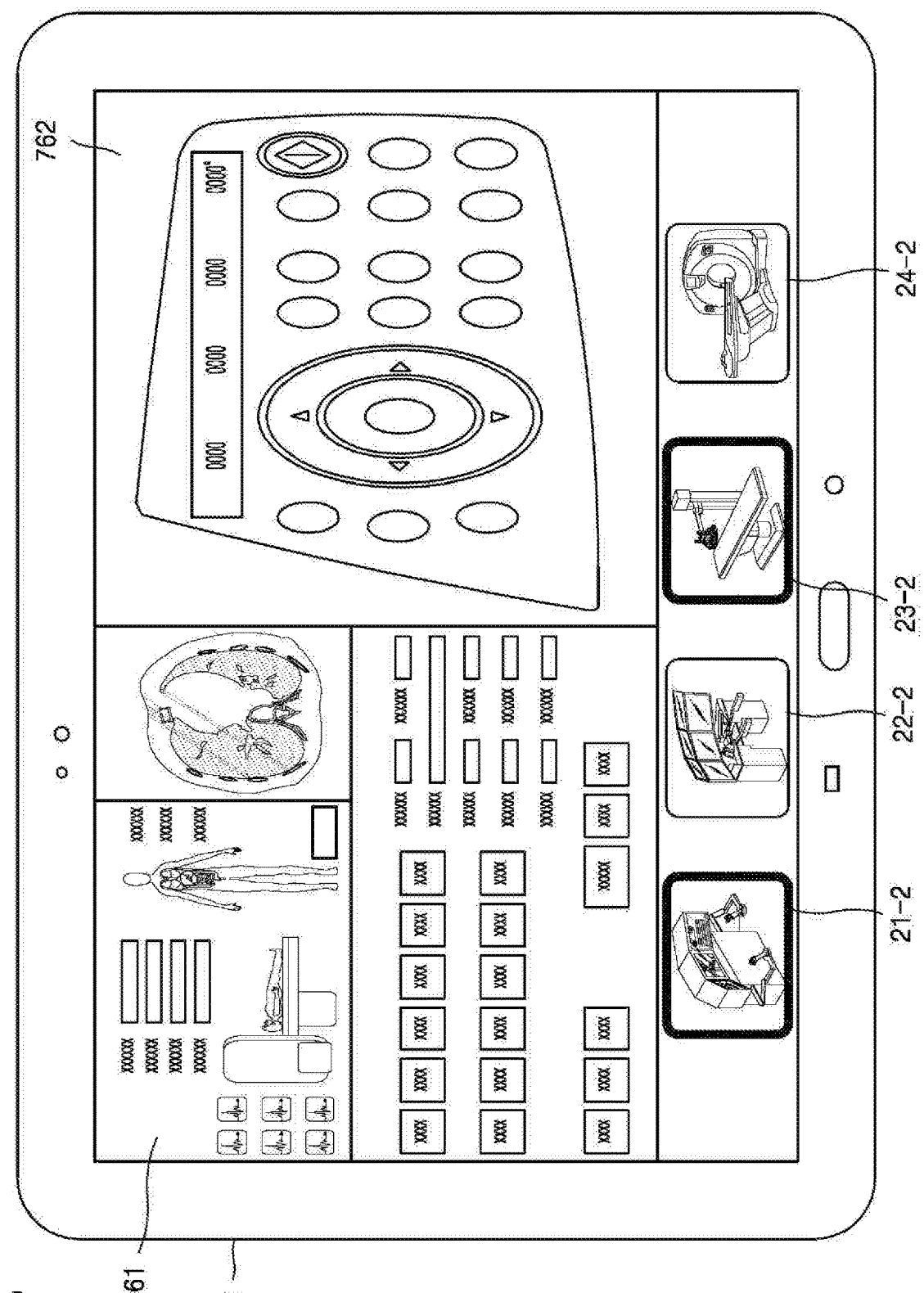

In response to the user input, as shown in 760 of FIG. 7F, the processor 190 may control the touch screen 200 such that a user interface 761 for controlling the first medical apparatus 21 and a user interface 762 for controlling the third medical apparatus 23 are simultaneously displayed. In this case, the identification information 21-2 that corresponds to the first medical apparatus 21 and the identification information 23-2 that corresponds to the third medical apparatus 23 may be highlighted.

Figure 8A:
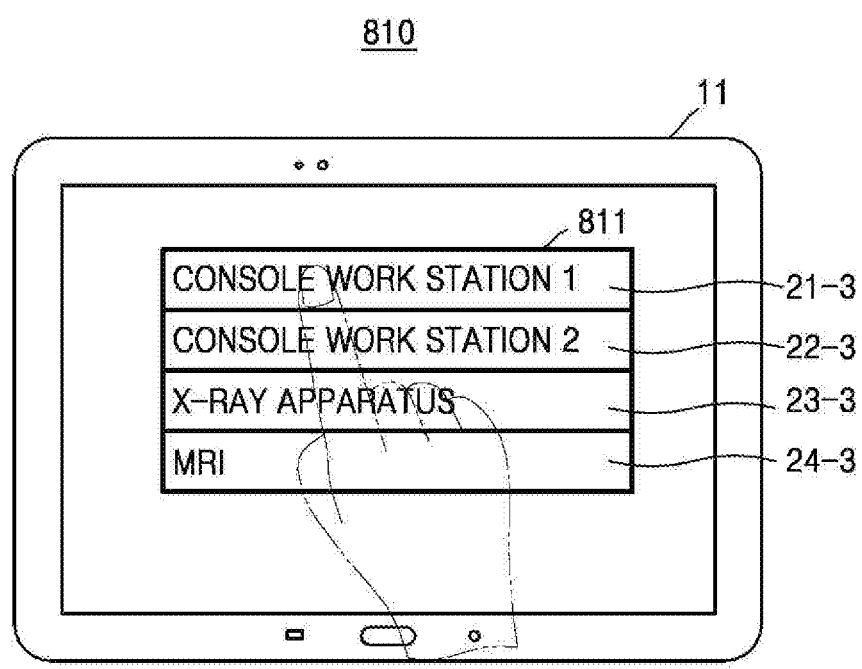
FIGS. 8A to 8C are diagrams of a mobile terminal displaying a user interface for controlling a medical apparatus, according to another exemplary embodiment.
Figure 8B:
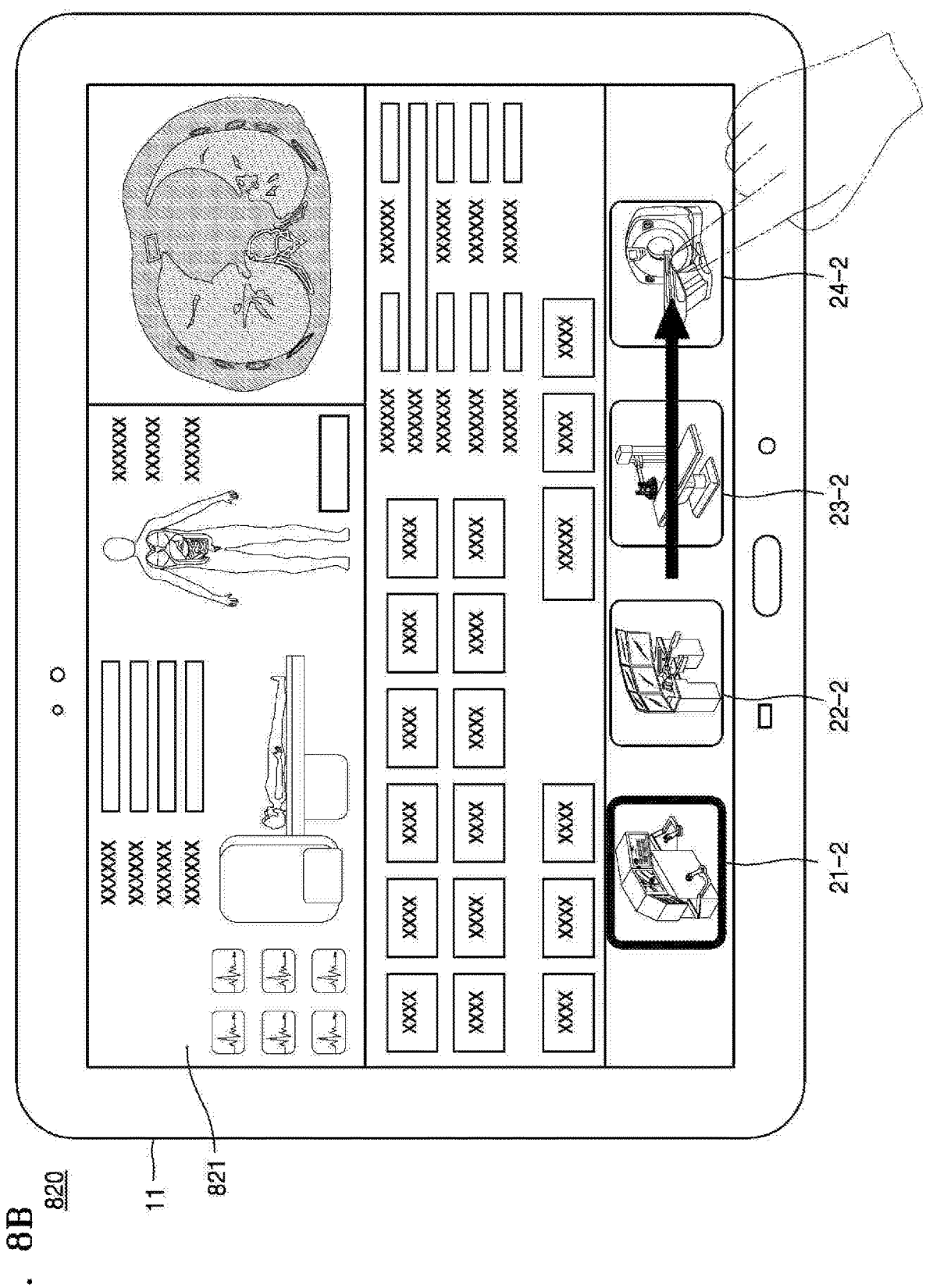
Figure 8C:
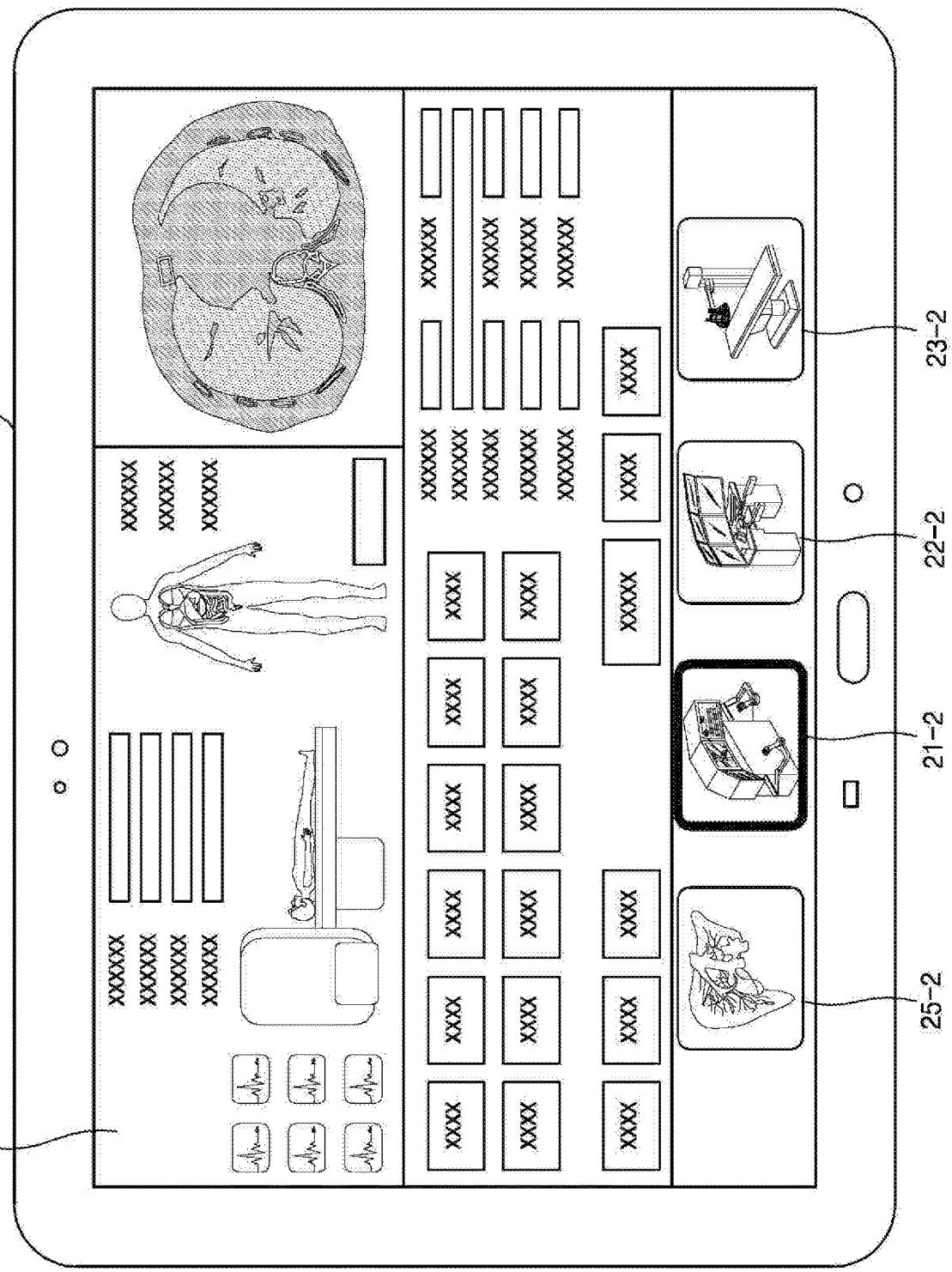

FIGS. 8A to 8C are diagrams of the mobile terminal 11 displaying a user interface for controlling a medical apparatus, according to another exemplary embodiment.

Referring to 810 of FIG. 8A, the processor 190 may control the touch screen 200 such that a medical apparatus control application is executed and thus a list 811 of medical apparatuses that are located within a certain range from the mobile terminal 11 is displayed. The list 811 may include identification information (e.g., names, model numbers, manufacturers, images, location information) 21-3 to 24-3 of the first to fourth medical apparatuses 21 to 24. While the list 811 is displayed, the touch screen 200 may detect a user input for selecting the identification information 21-3 of the first medical apparatus 21.

In response to the user input, as shown in 820 of FIG. 8B, the processor 190 may control a display unit such that a user interface 821 for controlling the first medical apparatus 21 is displayed. Along with the user interface 821, the identification information 21-3 to 24-3 that corresponds to the first to fourth medical apparatuses 21 to 24 may be displayed on an area of the touch screen 200. The touch screen 200 may detect a user input (e.g., a touch-and-drag gesture or a swipe gesture) on the area of the touch screen 200.

In response to the user input, as shown in 830 of FIG. 8C, the processor 190 may control the touch screen 200 such that at least some pieces of the identification information 21-2 to 24-2 are moved or removed and such that at least one piece of identification information 25-2 of at least one medical apparatus is displayed. In this case, the at least one medical apparatus that corresponds to the at least one piece of identification information 25-2 may be determined as at least one medical apparatus that is not located within a certain range from the mobile terminal 11 but found by the mobile terminal 11 or the medical apparatus management server.

FIGS. 9A to 9D are diagrams of the mobile terminal 11 displaying a user interface for controlling a medical apparatus, according to another exemplary embodiment.

Figure 9B:
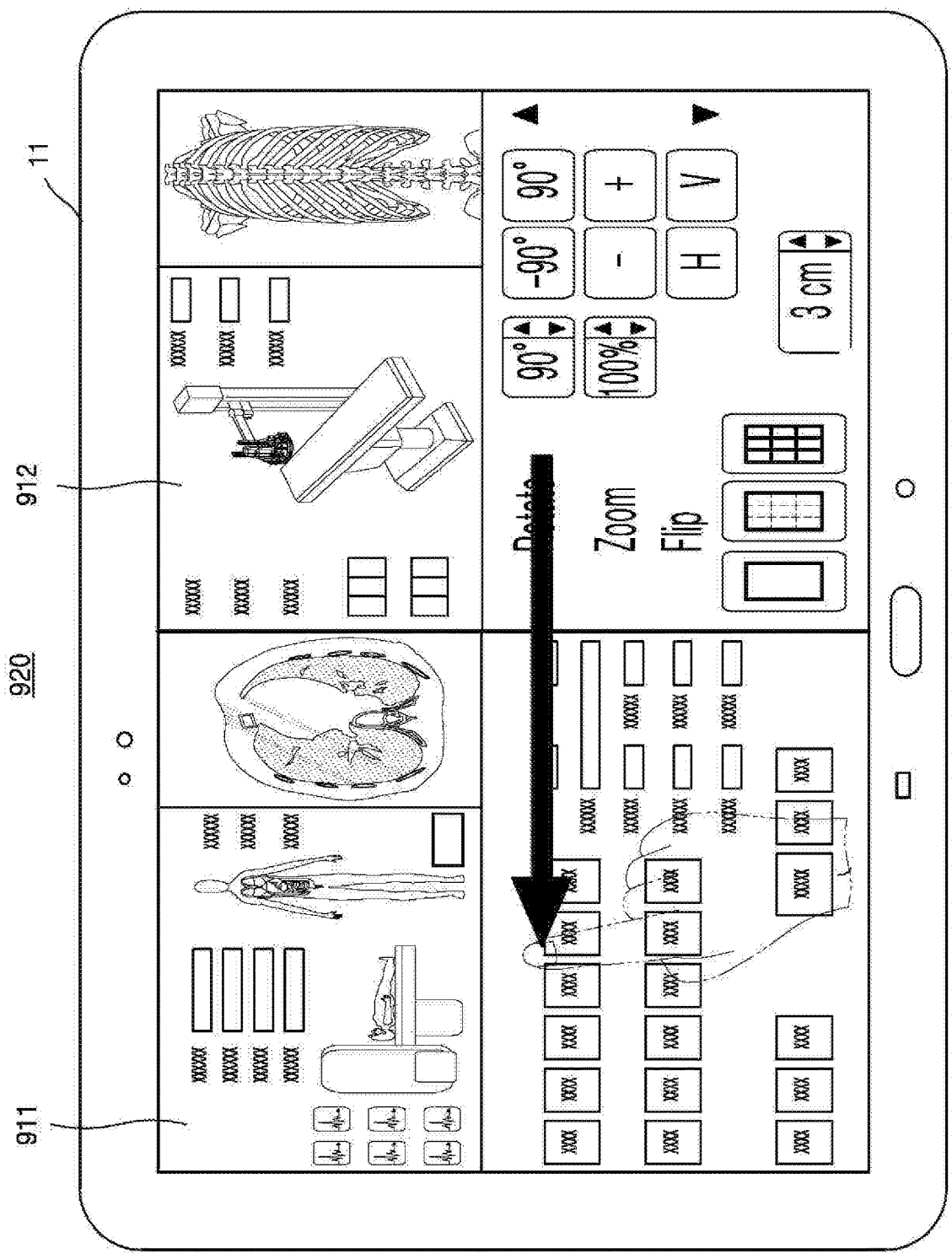

Referring to FIGS. 9A and 9B, when the processor 190 executes a medical apparatus control application, the processor 190 may control the touch screen 200 such that user interfaces 911 to 914 for controlling the first to fourth medical apparatuses 21 to 24 located within a certain range from the mobile terminal 11 are displayed in 910. FIG. 9A shows the user interfaces 911 to 914 for controlling the first to fourth medical apparatuses 21 to 24, and FIG. 9B shows the user interfaces 911 and 912 for controlling the first and second medical apparatuses 21 and 22.

In 920 of FIG. 9B, the touch screen 200 may detect a touch-and-drag gesture or a swipe gesture in a direction.

Figure 9C:
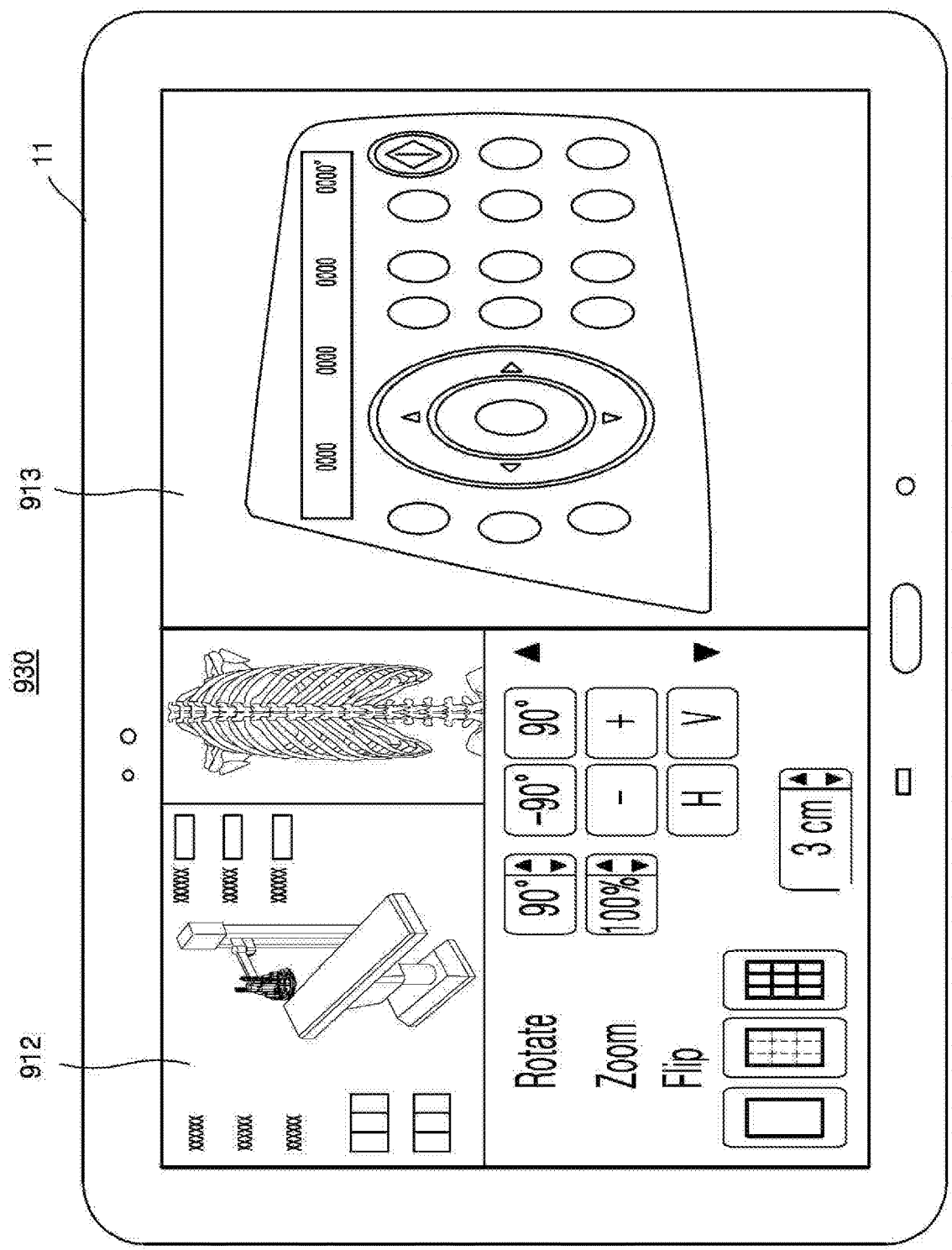

In response to the user input, as shown in 930 of FIG. 9C, the processor 190 may control the touch screen 200 such that the user interface 913 for controlling the third medical apparatus 23 from among the first to fourth medical apparatuses 21 to 24 located within a certain range from the mobile terminal 11 are simultaneously displayed with the user interface 912. Next, the touch screen 200 may detect a user input for selecting the user interface 913 from among the user interfaces 912 and 913.

Figure 9D:
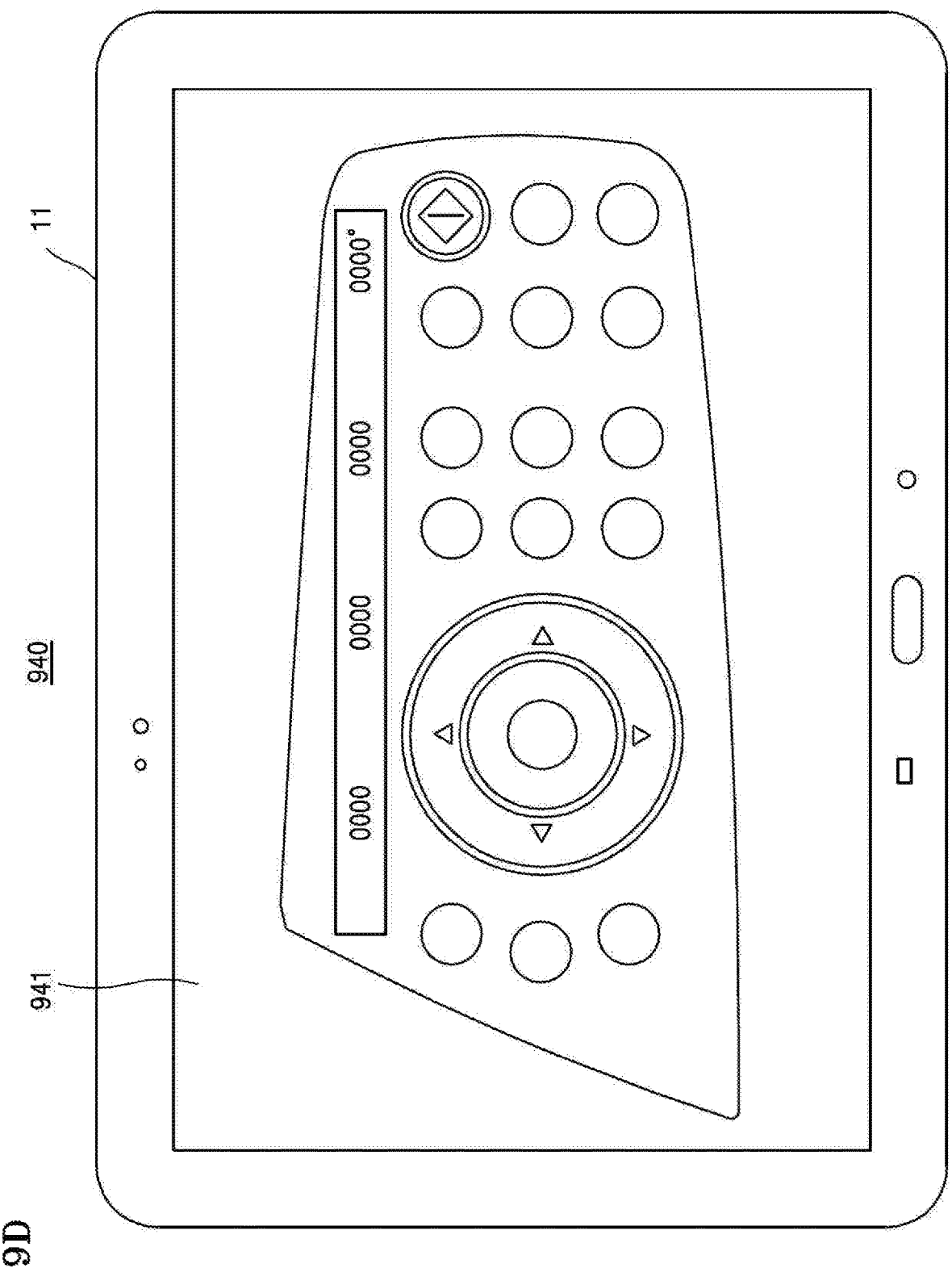

In response to the user input, as shown in 940 of FIG. 9D, the processor 190 may control the touch screen 200 such that an enlarged user interface 941 is displayed. Sizes of UI elements in the enlarged user interface 941 may be greater than UI elements in the user interface 913 that is not enlarged. In addition, more UI elements may be included in the enlarged user interface 941 than the user interface 913 that is not enlarged. Moreover, functions of the UI elements in the enlarged user interface 941 may be more diverse and detailed than functions of the UI elements in the user interface 913 that is not enlarged.

Figure 10A:
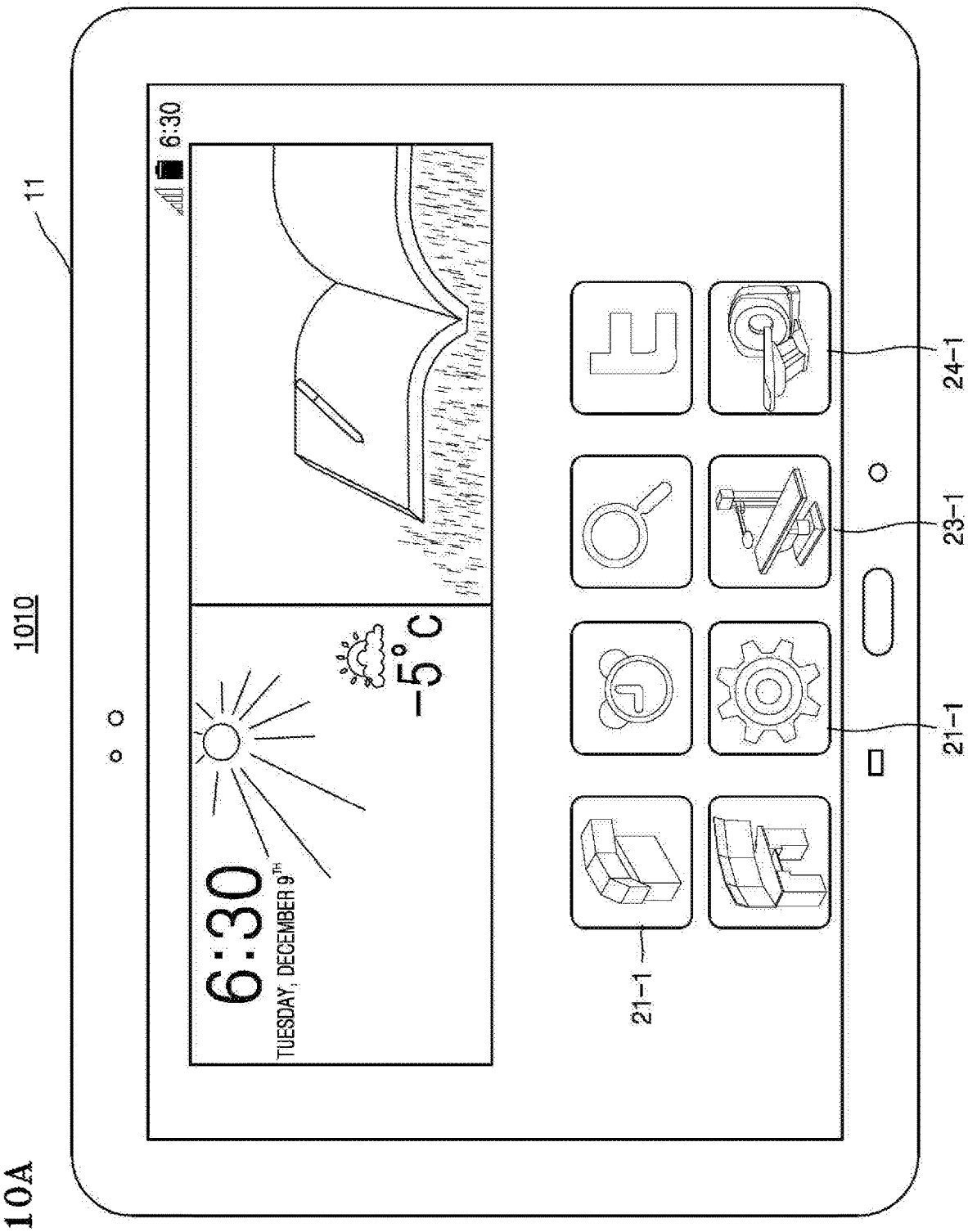
FIGS. 10A and 10B are diagrams of a mobile terminal displaying identification information of a medical apparatus, according to an exemplary embodiment.
Figure 10B:
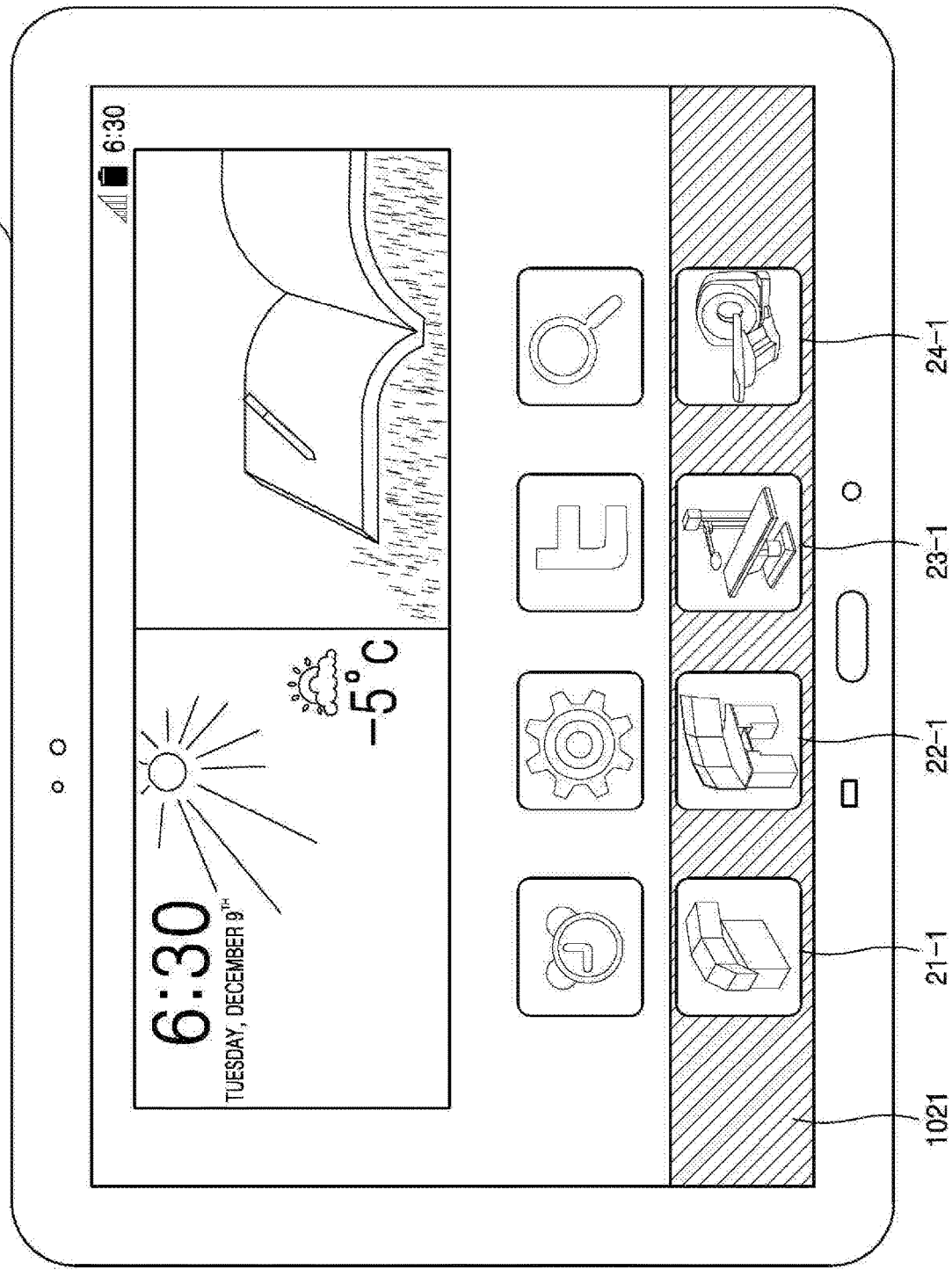

FIGS. 10A and 10B are diagrams of the mobile terminal 11 displaying identification information of a medical apparatus, according to an exemplary embodiment.

Referring to 1010 of FIG. 10A, the processor 190 may control the touch screen 200 such that shortcut icons (identification information 21-1 to 24-1) of the first to fourth medical apparatuses 21 to 24 are displayed with other icons on a home screen. Next, when the user carrying the mobile terminal 11 moves to the interior 1a where the first to fourth medical apparatuses 21 to 24 are located, the processor 190 may control the touch screen 200 such that the identification information 21-1 to 24-1 of the first to fourth medical apparatuses 21 to 24 that are within a certain range from the mobile terminal 11 are relocated or arranged and then displayed. For example, as shown in 1020 of FIG. 10B, the processor 190 may control the touch screen 200 such that the identification information 21-1 to 24-1 of the first to fourth medical apparatuses 21 to 24 are arranged and displayed on an area 1021 of the touch screen 200.

Figure 11A:
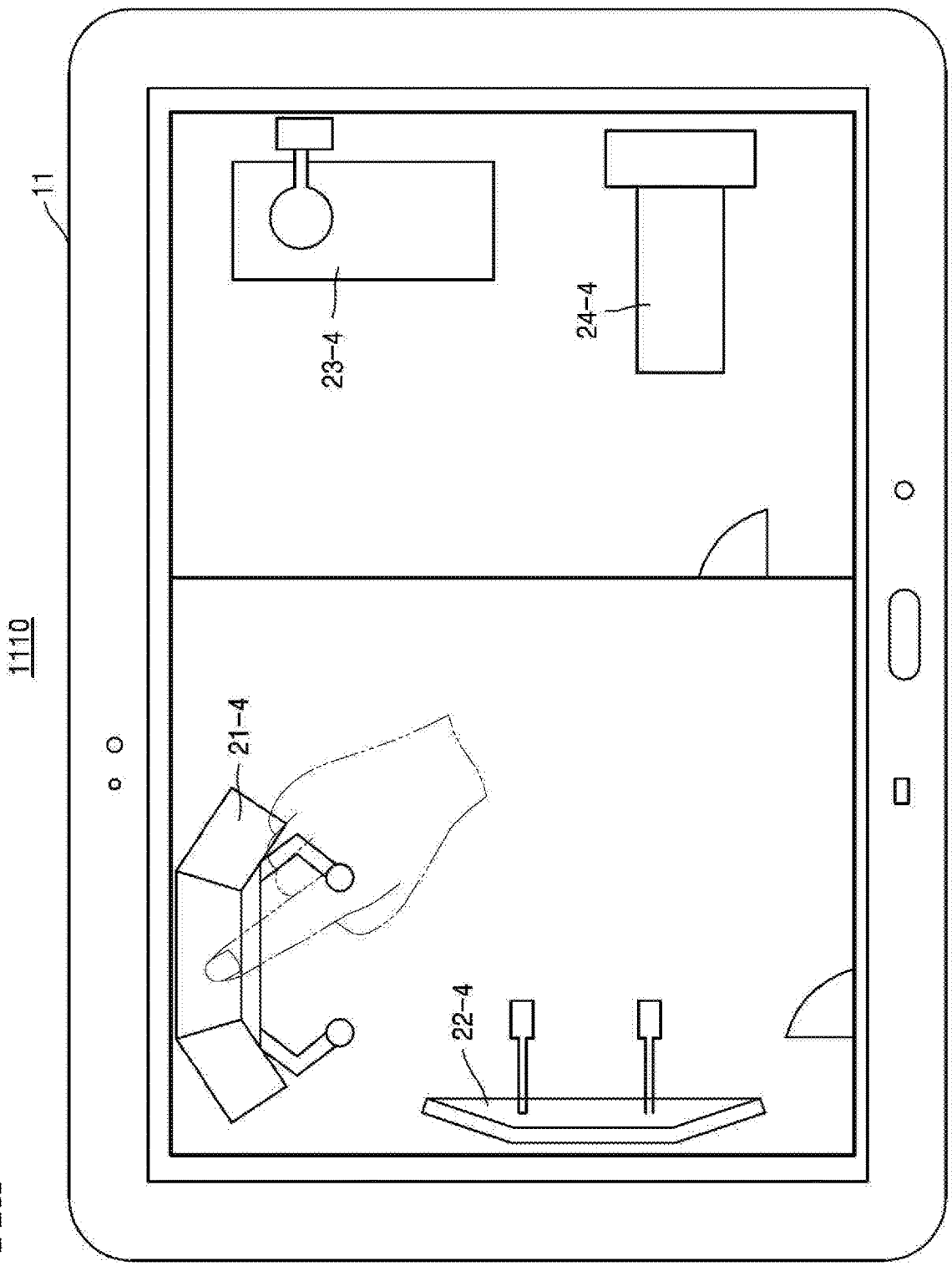
FIGS. 11A and 11B are diagrams of a mobile terminal displaying identification information of a medical apparatus, according to another exemplary embodiment.
Figure 11B:
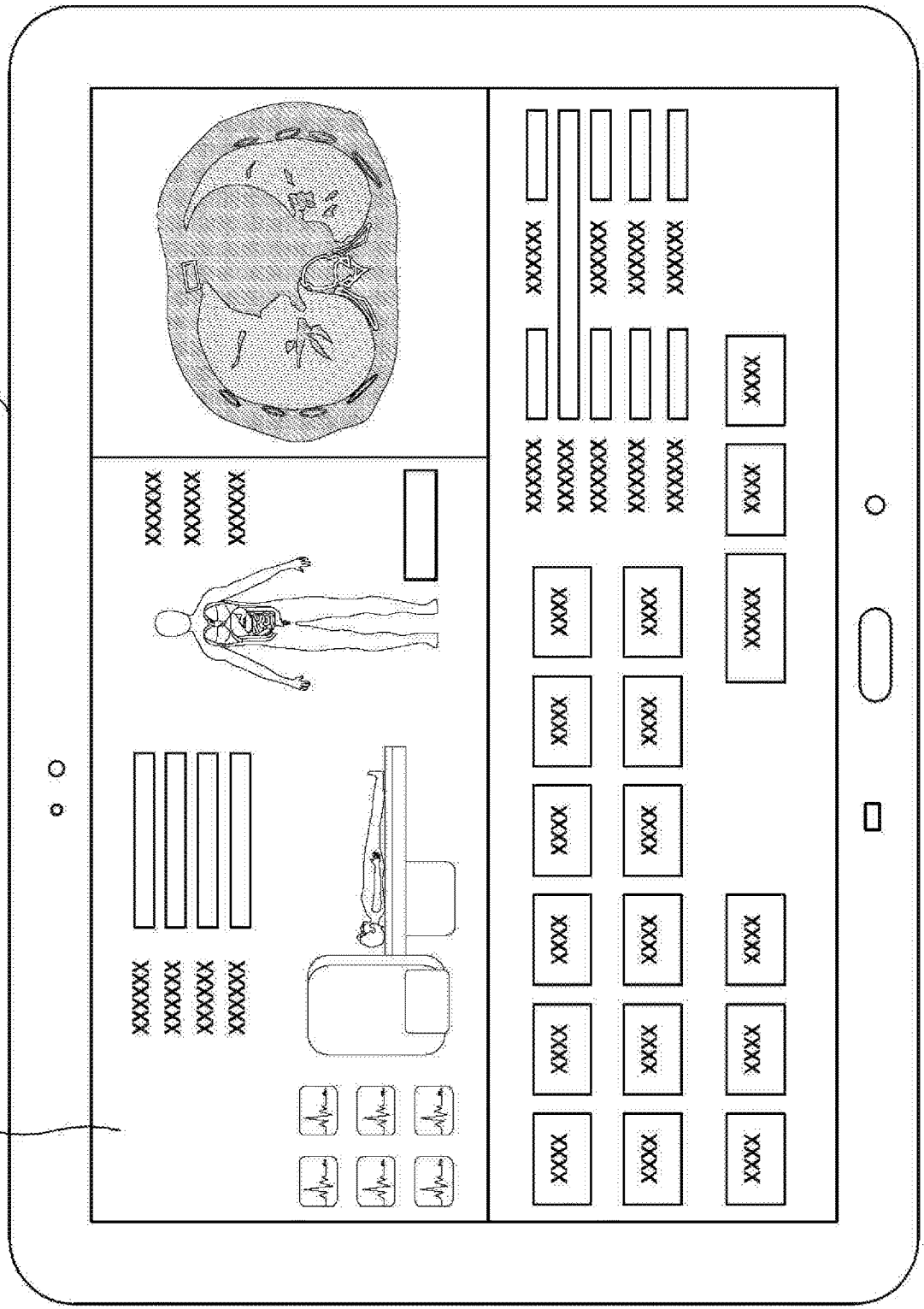

FIGS. 11A and 11B are diagrams of the mobile terminal 11 displaying identification information of a medical apparatus, according to another exemplary embodiment.

Referring to 1110 of FIG. 11A, the processor 190 may control the touch screen 200 such that identification information (e.g., images or icons) 21-4 to 24-4 of the first to fourth medical apparatuses 21 to 24 is displayed on a layout with respect to respective locations of the first to fourth medical apparatuses 21 to 24 in the interior 1a. The first to fourth medical apparatuses 21 to 24 that correspond to the identification information 21-4 to 24-4 may be located within a certain range from the mobile terminal 11.

In this case, respective locations of the identification information 21-4 to 24-4 of the first to fourth medical apparatuses 21 to 24 that are displayed on the layout may be shown as absolute locations or relative locations. For example, with regard to relative top/bottom/left/right locations of the first to fourth medical apparatuses 21 to 24, the identification information 21-4 to 24-4 of the first to fourth medical apparatuses 21 to 24 may be displayed on a top/bottom/left/right side of the layout. Alternatively, the identification information 21-4 to 24-4 of the first to fourth medical apparatuses 21 to 24 may be displayed as 3D objects on a 3D layout.

Next, the touch screen 200 may detect a user input for selecting the identification information 21-4 from among the identification information 21-4 to 24-4 of the first to fourth medical apparatuses 21 to 24.

In response to the user input, as shown in 1120 of FIG. 11B, the processor 190 may control the touch screen 200 such that a user interface 1121 for controlling the first medical apparatus 21 that corresponds to the selected identification information 21-4.

Figure 12:
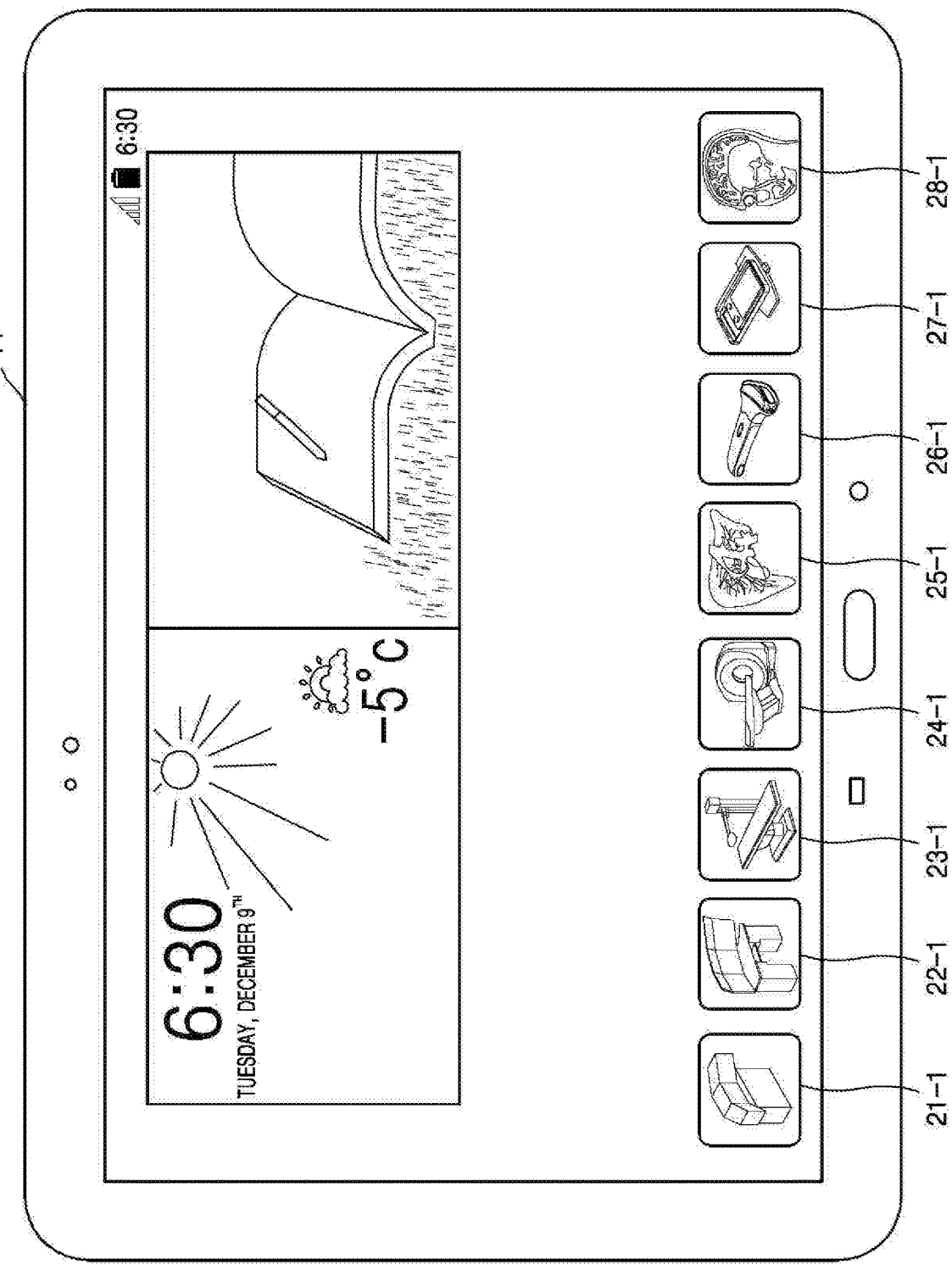
FIG. 12 is a diagram of a mobile terminal displaying identification information of a medical apparatus, according to another exemplary embodiment.

FIG. 12 is a diagram of the mobile terminal 11 displaying identification information of a medical apparatus, according to another exemplary embodiment.

Referring to FIG. 12, the processor 190 may control the touch screen 200 such that identification information 21-1 to 28-1 of medical apparatuses is displayed. The identification information 21-1 to 28-1 of the medical apparatuses may be displayed on an order from a medical apparatus that is nearest the mobile terminal 11 to the farthest. For example, the identification information 21-1 of the medical apparatus that is nearest to the mobile terminal 11 may be displayed at a leftmost side, and the identification information 28-1 of the medical apparatus that is farthest from the mobile terminal 11 may be displayed at a rightmost side.

As another example, if identification information of medical apparatuses are included in a list of the medical apparatuses, the identification information of the medical apparatus that is nearest to the mobile terminal 11 may be displayed at an upper side of the list, and the identification information of the mobile terminal 11 that is farthest away from the mobile terminal 11 may be displayed at a lower side of the list.

Figure 13:
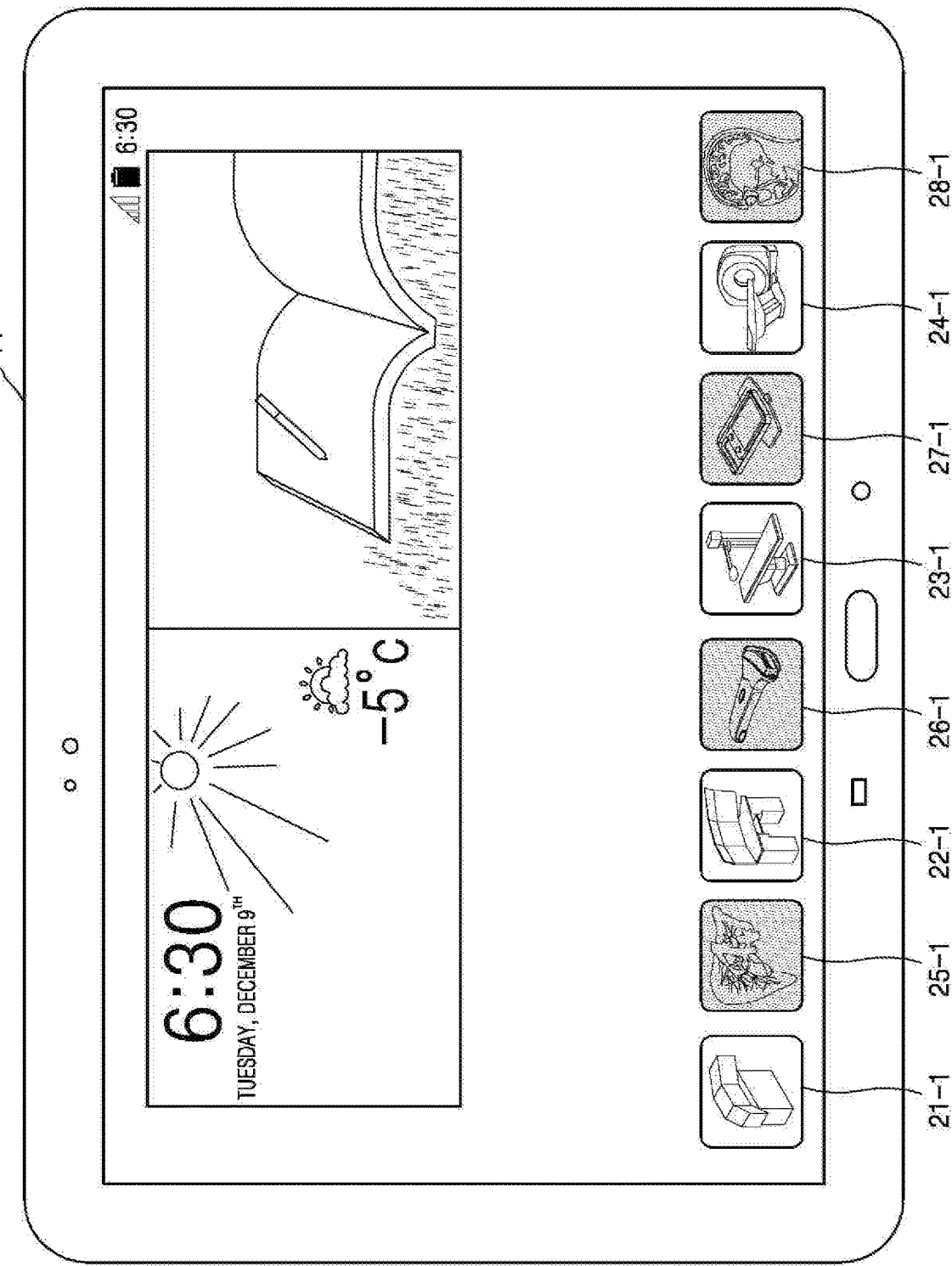
FIG. 13 is a diagram of a mobile terminal displaying identification information of a medical apparatus, according to another exemplary embodiment.

FIG. 13 is a diagram of the mobile terminal 11 displaying identification information of a medical apparatus, according to another exemplary embodiment.

Referring to FIG. 13, the processor 190 may control the touch screen 200 such that the identification information 21-1 to 28-1 of the medical apparatuses is displayed. In this case, the touch screen 200 may be controlled such that the identification information 21~1 to 24-1 of the medical apparatuses, which are determined to be located within a certain range from the mobile terminal 11, are activated and displayed, but the identification information 25~1 to 28-1 of the medical apparatuses, which are determined to be located outside a certain range from the mobile terminal 11, are deactivated and displayed. Activated identification information and deactivated identification information may be displayed with different shapes, sizes, contrasts, or colors.

Figure 14A:
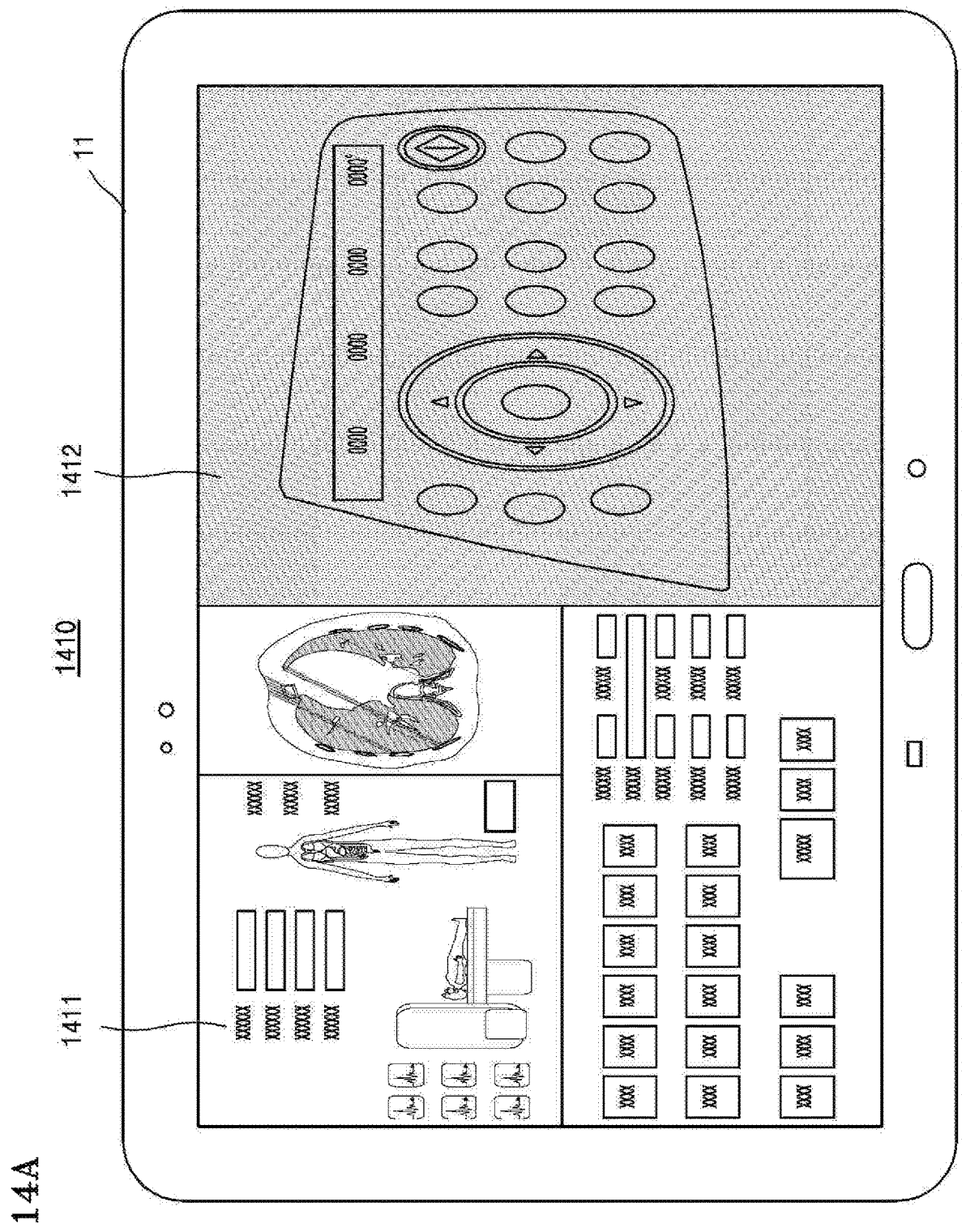
FIGS. 14A and 14B are diagrams of a mobile terminal displaying a user interface for controlling a medical apparatus, according to another exemplary embodiment.
Figure 14B:
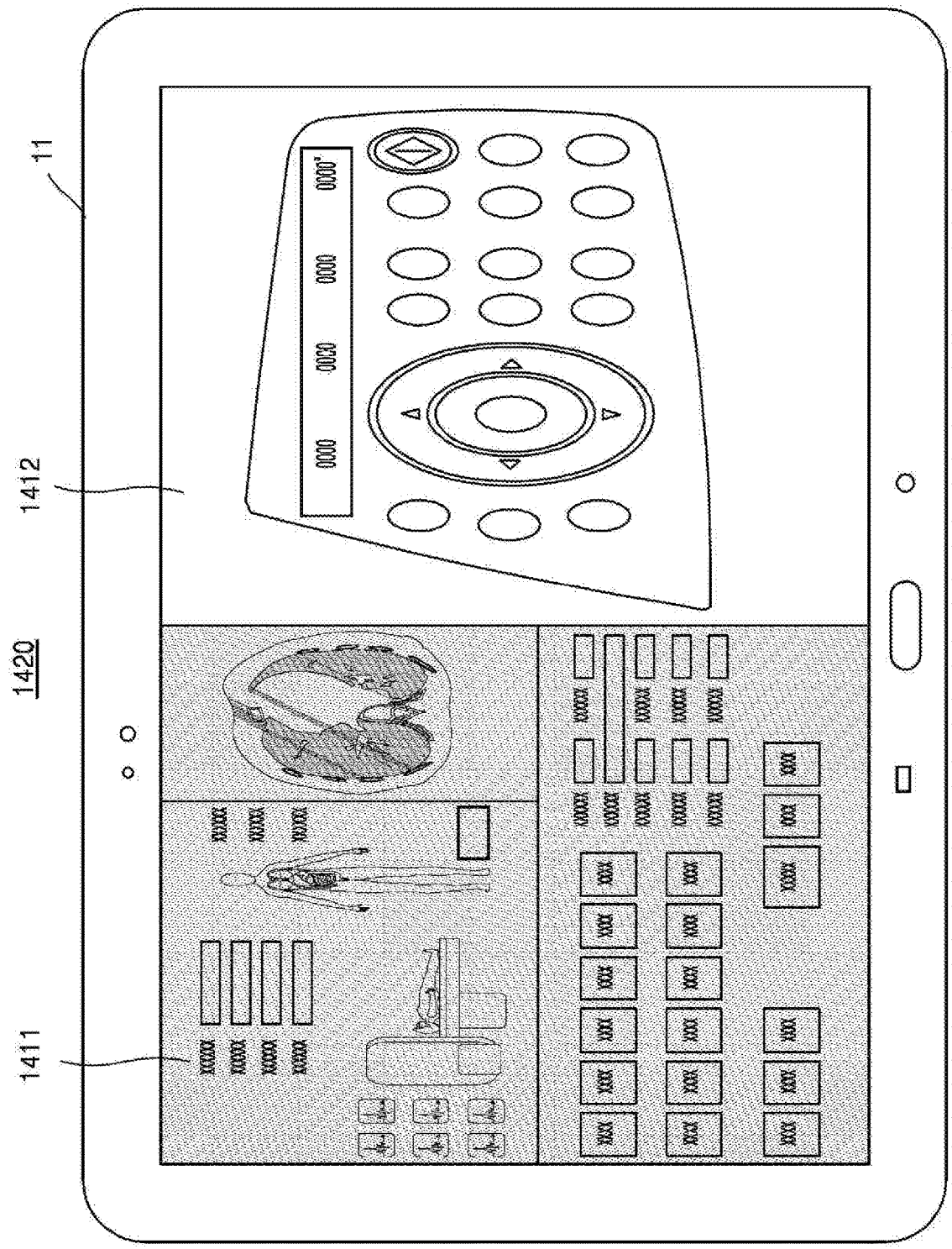

FIGS. 14A and 14B are diagrams of the mobile terminal 11 displaying a user interface for controlling a medical apparatus, according to another exemplary embodiment.

Referring to 1410 of FIG. 14A, the processor 190 may control the touch screen 200 such that user interfaces 1411 and 1412 of found medical apparatuses is displayed display. In this case, the touch screen 200 may be controlled such that the user interface 1411 of the medical apparatus that is determined to be within a certain range from the mobile terminal 11 may be activated and displayed, but the user interface 1412 of the medical apparatus that is determined to be outside a certain range from the mobile terminal 11 and located in another range may be deactivated and displayed.

Next, when the user moves and thus a location of the mobile terminal 11 is changed, as shown in 1420 of FIG. 14B, the processor 190 may control the touch screen 200 such that the user interface 1412 of the medical apparatus that is determined to be within a certain range from the mobile terminal 11 with respect to the changed location may be active and displayed, and the user interface 1411 that is determined to be outside a certain range from the mobile terminal 11 and located in another range may be deactivated and displayed.

Figure 15:
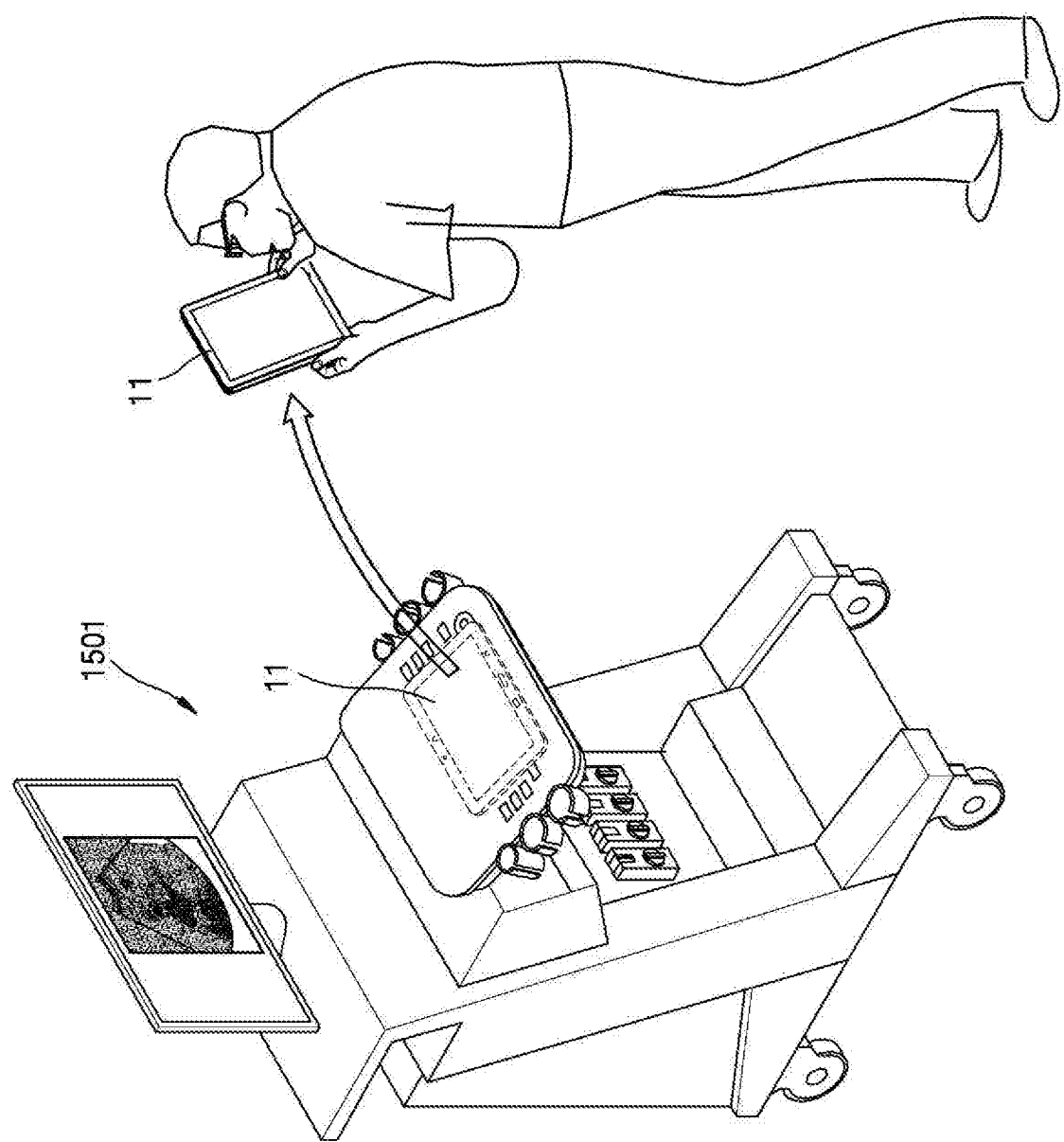
FIG. 15 is a diagram for describing using a mobile terminal as a manipulator of a medical apparatus, according to an exemplary embodiment.

FIG. 15 is a diagram for describing using the mobile terminal 11 as a manipulator of a medical apparatus 1501, according to an exemplary embodiment.

Referring to FIG. 15, the mobile terminal 11 may be attachable to and detachable from the medical apparatus 1501. For example, when a terminal coupling unit or a terminal attaching unit is provided in the medical apparatus 1501, the user may attach and detach the mobile terminal 11 to and from the terminal coupling unit or the terminal attaching unit. The terminal coupling unit or the terminal attaching unit may comprise a connector that is configured to connect to the mobile terminal 11 to the medical apparatus 1501 and through which data is sent and received. The terminal coupling unit or the terminal attaching unit may also comprise an attachment assembly configured to hold the mobile terminal 11 and/or detect that the mobile terminal 11 is attached to the medical apparatus 1501.

In this case, while controlling the medical apparatus 1501 via the mobile terminal 11, the user may attach the mobile terminal 11 to the terminal coupling unit or the terminal attaching unit of the medical apparatus 1501 and continue to control the medical apparatus 1501. Further, while controlling the medical apparatus 1501 via the mobile terminal 11 that is attached to the terminal coupling unit or the terminal attaching unit of the medical apparatus 1501, the user may separate the mobile terminal 11 and continue to control the medical apparatus 1501 while moving.

A user interface displayed on the mobile terminal 11 that is coupled or attached to the medical apparatus 1501 may be different from a user interface displayed on the mobile terminal 11 that is separated from the medical apparatus 1501.

For example, when the mobile terminal 11 that is separated from the medical apparatus 1501 is coupled to or attached to the medical apparatus 1501 while the mobile terminal 11 is displaying a plurality of user interfaces that correspond to medical apparatuses, the mobile terminal 11 may display only a user interface that corresponds to the medical apparatus 1501 to which the mobile terminal 11 is attached.

Accordingly, since the mobile terminal 11 may be attachable to and detachable from a medical apparatus, the user may more conveniently manipulate the medical apparatus with greater mobility, and a synergy effect may be generated due to such improvement.

Figure 16A:
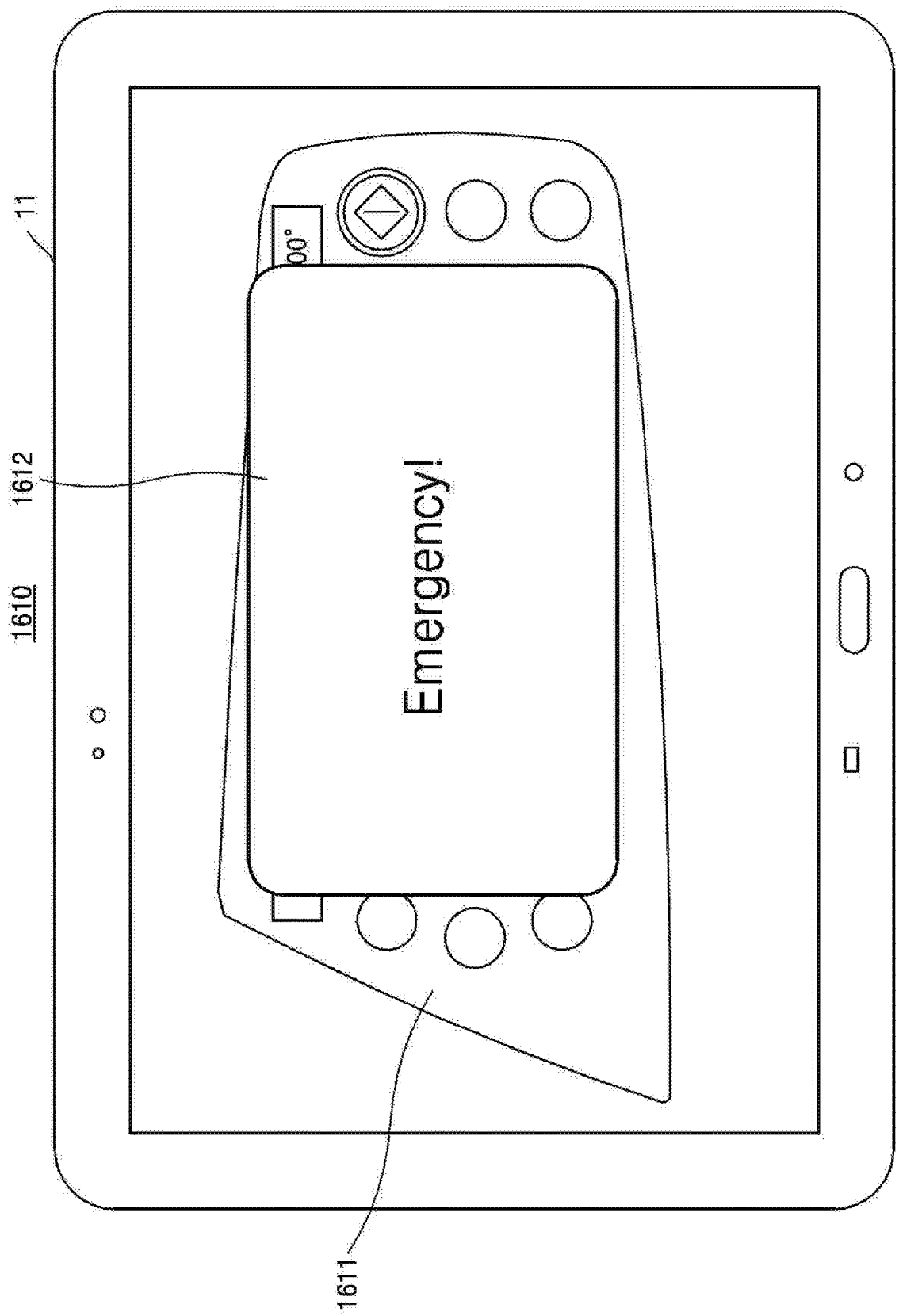
FIGS. 16A and 16B are diagrams for describing the displaying of notification information in a mobile terminal, according to an exemplary embodiment.
Figure 16B:
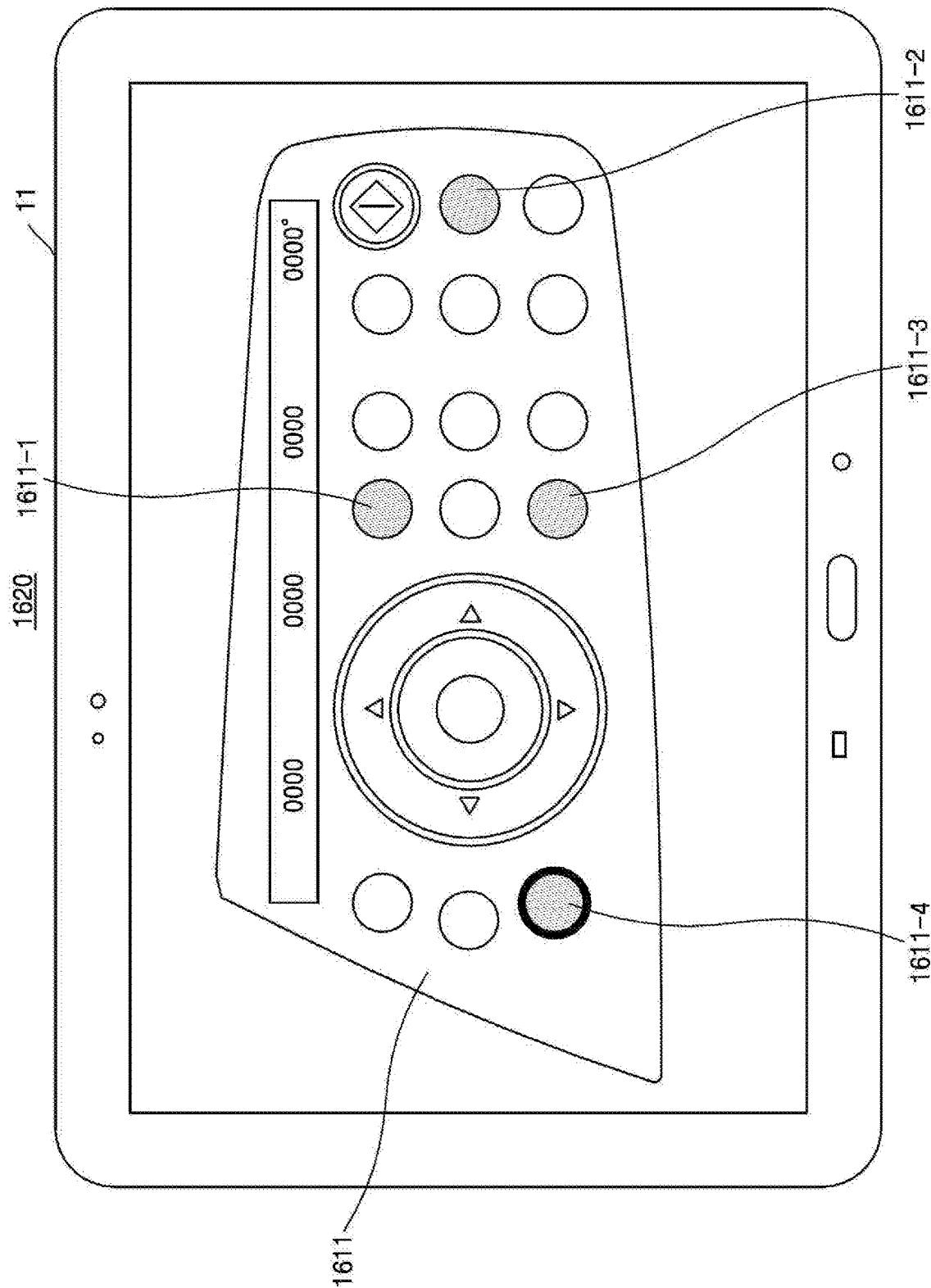

FIGS. 16A and 16B are diagrams for describing displaying notification information in the mobile terminal 11, according to an exemplary embodiment.

Referring to 1610 of FIG. 16A, when an emergency situation occurs while the user is controlling a first medical apparatus via a user interface 1611 that corresponds to the first medical apparatus, the processor 190 may control the touch screen 200 such that notification information 1612 is displayed. In this case, the notification information 1612 may be continuously displayed until a user input is detected or flash at certain rates.

The emergency situation may be, for example, a side-effect occurring in a patient when the user injects a contrast medium with an injector to capture an image of organs of the patient. An emergency situation or critical situation of a patient may be, for example, cardiac arrest, shock, or death.

In order to determine such situations, a cardiography apparatus may continuously monitor the heart rate of the patient. If it is determined that the heart rate of the patient is decreasing, the cardiography apparatus may transmit information that notifies a dangerous state of the patient to the mobile terminal 11. Alternatively, when the dangerous state of the patient is notified to an external cloud or server, the external cloud or server may transmit the information that notifies the dangerous state of the patient to the mobile terminal 11.

While the notification information 1612 is being displayed, a user input for selecting the notification information 1612 may be detected, or a predetermined time (e.g., 30 seconds or 300 seconds) may be elapsed.

In this case, as shown in 1620 of FIG. 16B, the processor 190 may control the touch screen 200 such that at least one selected from UI elements 1611-1, 1611-2, and 1611-3, which is irrelevant to diagnosis of the patient, is changed from an activated state from a deactivated state, so that the user to quickly determine. For example, the processor 190 may control such that a UI element that starts scanning of the patient is deactivated. Also, the processor 190 may recommend a UI element 1611-4 that is necessary for taking critical actions on the patient in an emergency situation. For example, the processor 190 may control the touch screen 200 such that the UI element 1611-4 necessary for taking urgent actions on the patient in the emergency situation may be highlighted (e.g., an animation effect such as changing saturation or brightness, flashing, or enlarging) and displayed. Alternatively, the processor 190 may control the touch screen 200 such that a new UI element that is necessary for taking urgent actions on the patient. The new UI element may be a UI element for controlling the first medical apparatus, or a UI element for controlling a second medical apparatus that is different from the first medical apparatus. Alternatively, the processor 190 may control the touch screen 200 such that a deactivated UI element is activated. That is, if a UI element that is necessary for taking urgent actions on the patient was deactivated, the processor 190 may change the UI element to an activated state.

The UI element that is necessary for taking urgent actions on the patient may include at least one selected from, for example, a UI element for locking and unlocking a cradle, a UI element for manipulating a table, a UI element for pausing or ending scanning, a UI element for manipulating gantry tilting, and a UI element for emergency stopping an operation of a gantry or stopping an operation of an injector.

According to another exemplary embodiment, an emergency situation may be when a table malfunctions. For example, the malfunctioning may occur when the table unintentionally moves due to a fault in a motor of the table, the table vertically collapses, or the table is set in a wrong manner.

In order to determine such situations, the table or a medical apparatus may include an impact or a shock sensor. In this case, when malfunctioning occurs, the sensor may transmit information that notifies the dangerous state of the patient to the mobile terminal 11. Alternatively, if the dangerous state of the patient is notified to an external cloud or server, the external cloud or server may transmit the information for notifying the dangerous state of the patient to the mobile terminal 11.

In this case, the processor 190 may control such that a UI element that is irrelevant for diagnosing the patient in the emergency situation is deactivated so that the user may quickly determine. For example, the processor 190 may control such that a UI element for starting scanning of the patient is deactivated. Also, the processor 190 may recommend a UI element that is necessary for taking urgent actions on the patient in the emergency situation. The UI element that is necessary for taking urgent actions may include at least one selected from, for example, a UI element for locking and unlocking a cradle, a UI element for manipulating the table, a UI element for pausing or ending scanning, and a UI element for emergency stopping an operation of the table.

According to another exemplary embodiment, an emergency situation may be when titling of a gantry malfunctions. For example, the malfunctioning may occur when the gantry inclines due to a fault in a motor of the gantry. Also, various situations that occur when designing the gantry or setting the motor of the gantry.

In order to determine such situations, the gantry or a medical apparatus may include an impact or a shock sensor. In this case, when malfunctioning occurs, the sensor may transmit information that notifies the dangerous state of the patient to the mobile terminal 11. Alternatively, if the dangerous state of the patient is notified to an external cloud or server, the external cloud or server may transmit the information for notifying the dangerous state of the patient to the mobile terminal 11.

In this case, the processor 190 may deactivate a UI element that is irrelevant for diagnosing the patient in the emergency situation so that the user may quickly determine. For example, the processor 190 may deactivate a UI element for starting scanning of the patient. Also, the processor 190 may recommend a UI element that is necessary for taking urgent actions on the patient in the emergency situation. The UI element that is necessary for taking urgent actions may include at least one selected from, for example, a UI element for locking and unlocking a cradle, a UI element for manipulating the table, a UI element for pausing or ending scanning, and a UI element for emergency stopping an operation of the gantry.

According to another exemplary embodiment, a communication connection may be disabled. For example, a communication connection between medical apparatuses via a controller area network (CAN) may be disabled. In this case, when information of disconnected medical apparatuses is transmitted to the mobile terminal 11, the processor 190 may control the touch screen 200 such that the information of the disconnected medical apparatuses is displayed on a pop-up screen image or a split screen image.

Figure 17B:
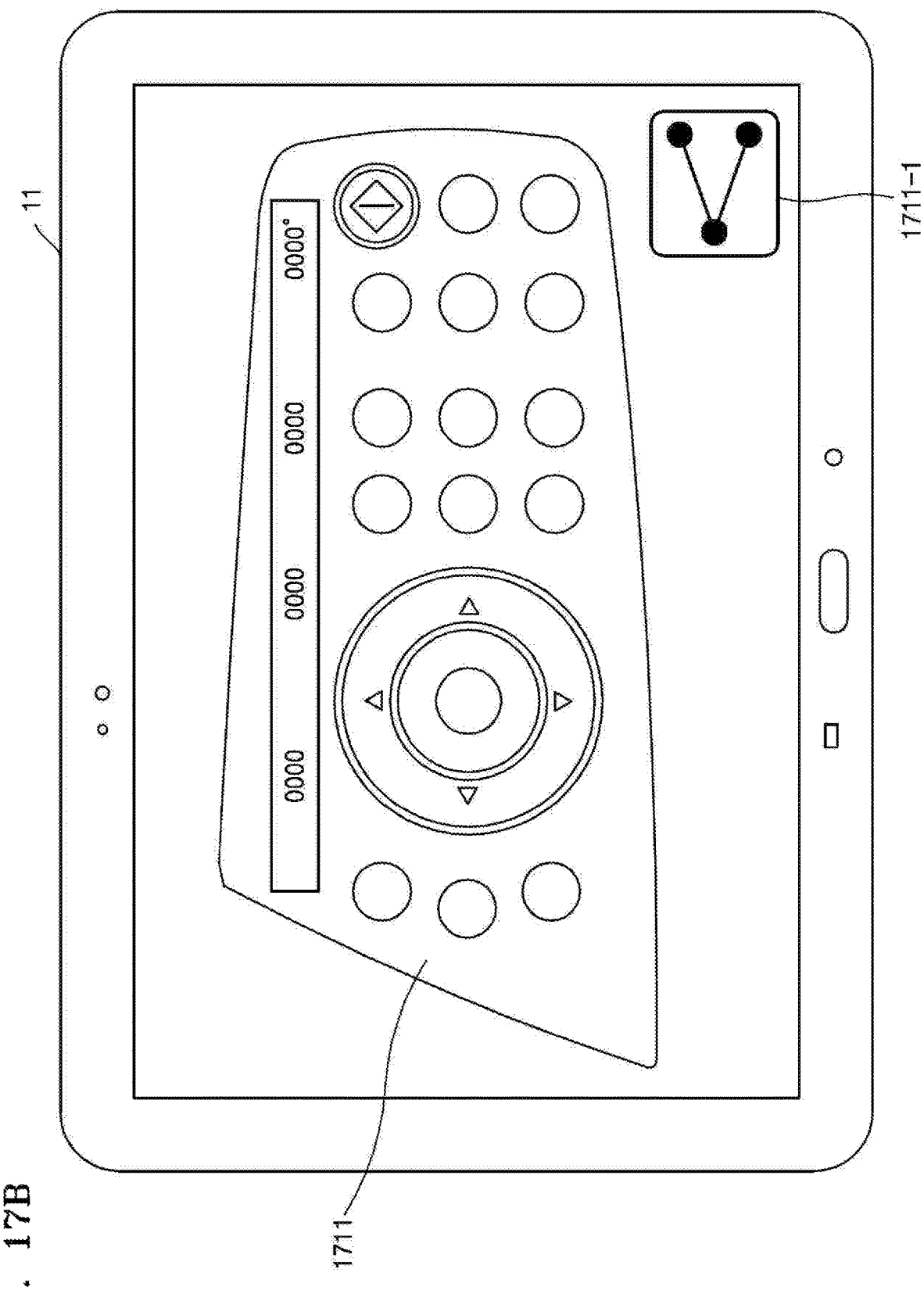
Figure 17C:
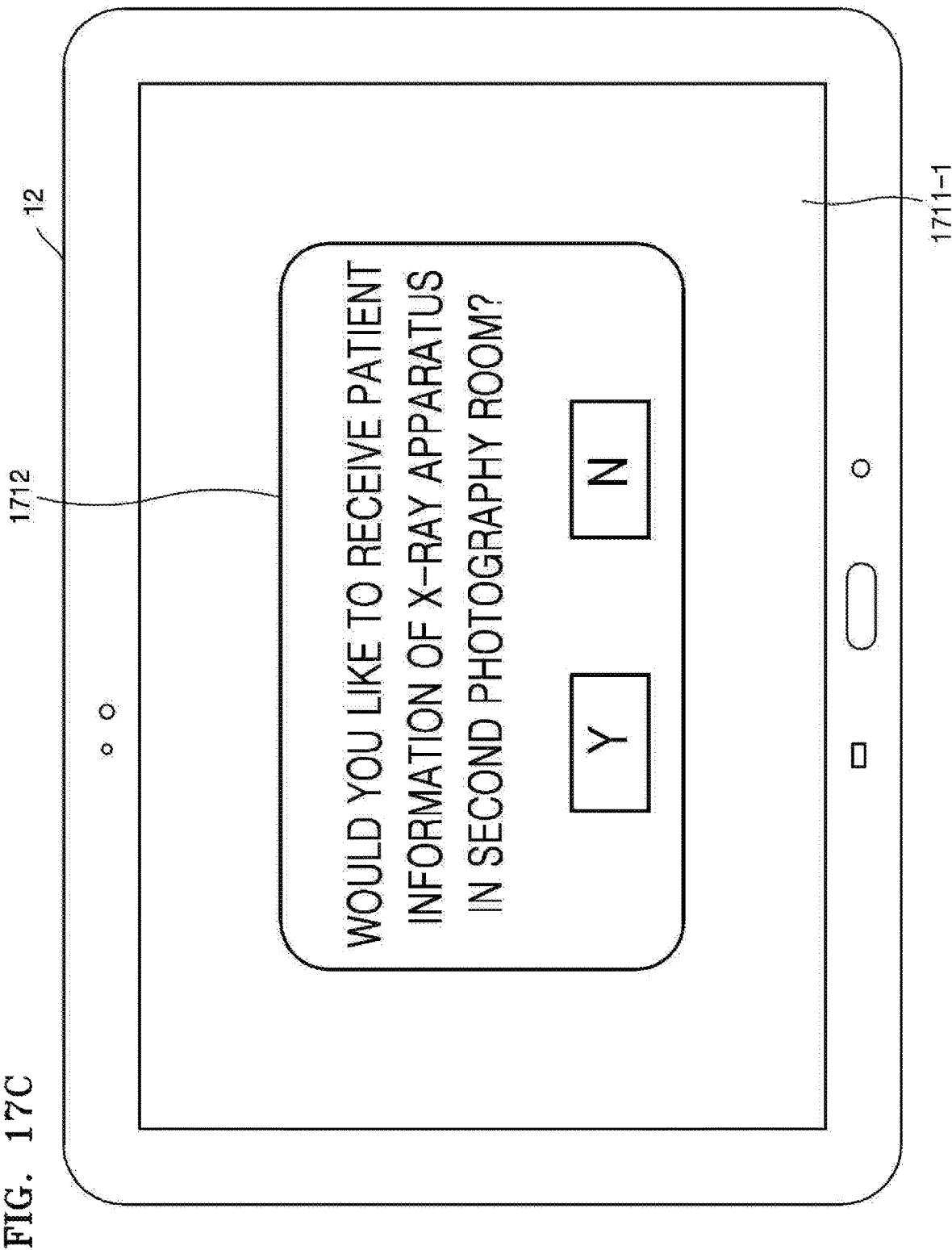

FIGS. 17A to 17C are diagrams for describing using a plurality of mobile terminals to control a medical apparatus, according to an exemplary embodiment.

Referring to FIG. 17A, when a first user carrying he mobile terminal 11 is located in a first photography room 1c, the processor 190 of the mobile terminal 11 may control the touch screen 200 such that a user interface for controlling at least one of the third and fourth medical apparatuses 23 and 24. In this case, the processor 190 may control such that information related to the user interface displayed on the mobile terminal 11 is transmitted to a mobile terminal 12 that is carried by a second user in a second photography room 1d with medical apparatuses 25 and 26.

For example, as shown in FIG. 17B, a UI element 1711-1, for sharing a user interface 1711 displayed on the mobile terminal 11 with the second user, may be displayed. In this case, in response to a first user input for selecting the UI element 1711-1, the processor 190 may control such that information related to the user interface 1711 is transmitted to the mobile terminal 12 of the second user. Also, when at least one medical apparatus is manipulated via the mobile terminal 11, the processor 190 may control such that information related to the user interface 1711 that is automatically being displayed is transmitted to the mobile terminal 12 of the second user. The information related to the user interface 1711 may be, for example, data generated by compressing the user interface 1711, identification information of user interface 1711, identification information of a medical apparatus that corresponds to the user interface 1711, or manipulation information that is input by a user via the user interface 1711.

As another example, when information related to a patient is obtained via the mobile terminal 11, the processor 190 may control such that the information related to the patient is transmitted to the mobile terminal 12 of the second user. For example, when an image or bio-information of the patient is obtained as a diagnosis result of the patient, the processor 190 may control such that the information related to the patient is transmitted to the mobile terminal 12 of the second user via the communicator 140.

Specifically, when a result of capturing an image of the patient by using the third medical apparatus 23 in the first photography room 1c is obtained, the mobile terminal 11 may transmit the result to the mobile terminal 12 that is located in the second photography room 1d.

Alternatively, when setting information (e.g., location information of a table) of a medical apparatus in the first photography room 1c is obtained, the mobile terminal 11 may transmit the setting information of the medical apparatus to the mobile terminal 12 that is located in the second photography room 1d.

The processor 190 of the mobile terminal 11 may control the touch screen 200 such that a menu for selecting a mobile terminal to which a user interface or information related to a patient is transmitted from among a plurality of mobile terminals. In this case, in response to a user input for selecting a mobile terminal from among the plurality of mobile terminals, the processor 190 may transmit a user interface or the information related to the patient to the selected mobile terminal.

Referring to FIG. 17C, when the user interface or the information related to the patient is received by the mobile terminal 11 in the first photography room 1c, the processor 190 of the mobile terminal 12 in the second photography room 1d may control the touch screen 200 such that notification information 1712 that notifies the information is received from the mobile terminal 11 is displayed. Next, in response to a user input for agreeing to receive the information, the mobile terminal 12 may receive the user interface displayed on the mobile terminal 11 or the information related to the patient which is estimated in the mobile terminal 11. Also, when the user requests or automatically, the mobile terminal 12 may control the touch screen 200 such that the received user interface or the received information related to the patient is displayed.

Accordingly, at least one selected from the user interface, the information related to the patient, and the setting information of a medical apparatus may be mirrored between the mobile terminals 11 and 12 located in different places. Therefore, users that diagnose an identical patient may be able to conveniently control a medical apparatus and quickly manipulate the medical apparatus with respect to an emergency patient.

Figure 18A:
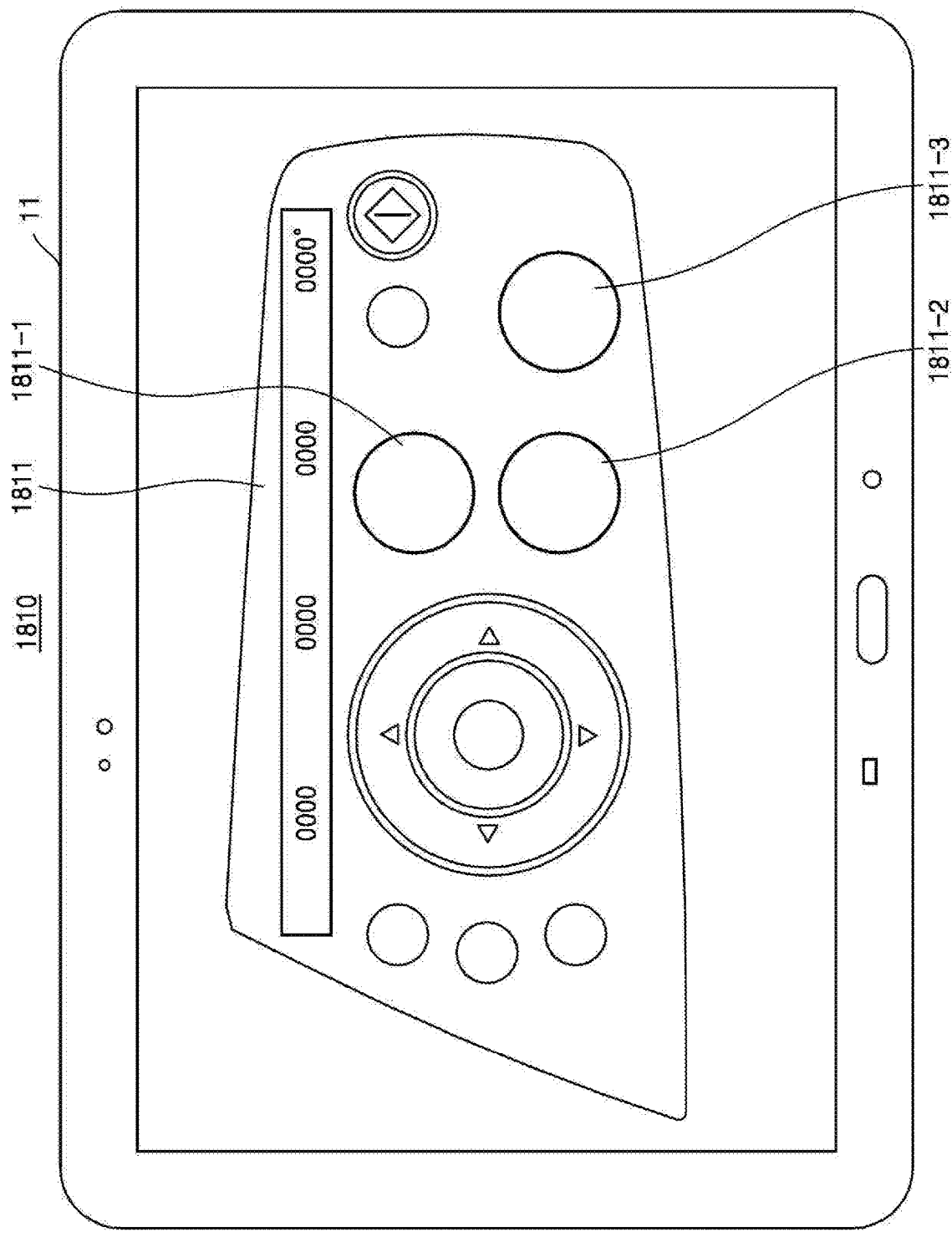
FIGS. 18A and 18B are diagrams of a mobile terminal displaying a user interface for controlling a medical apparatus, according to another exemplary embodiment.
Figure 18B:
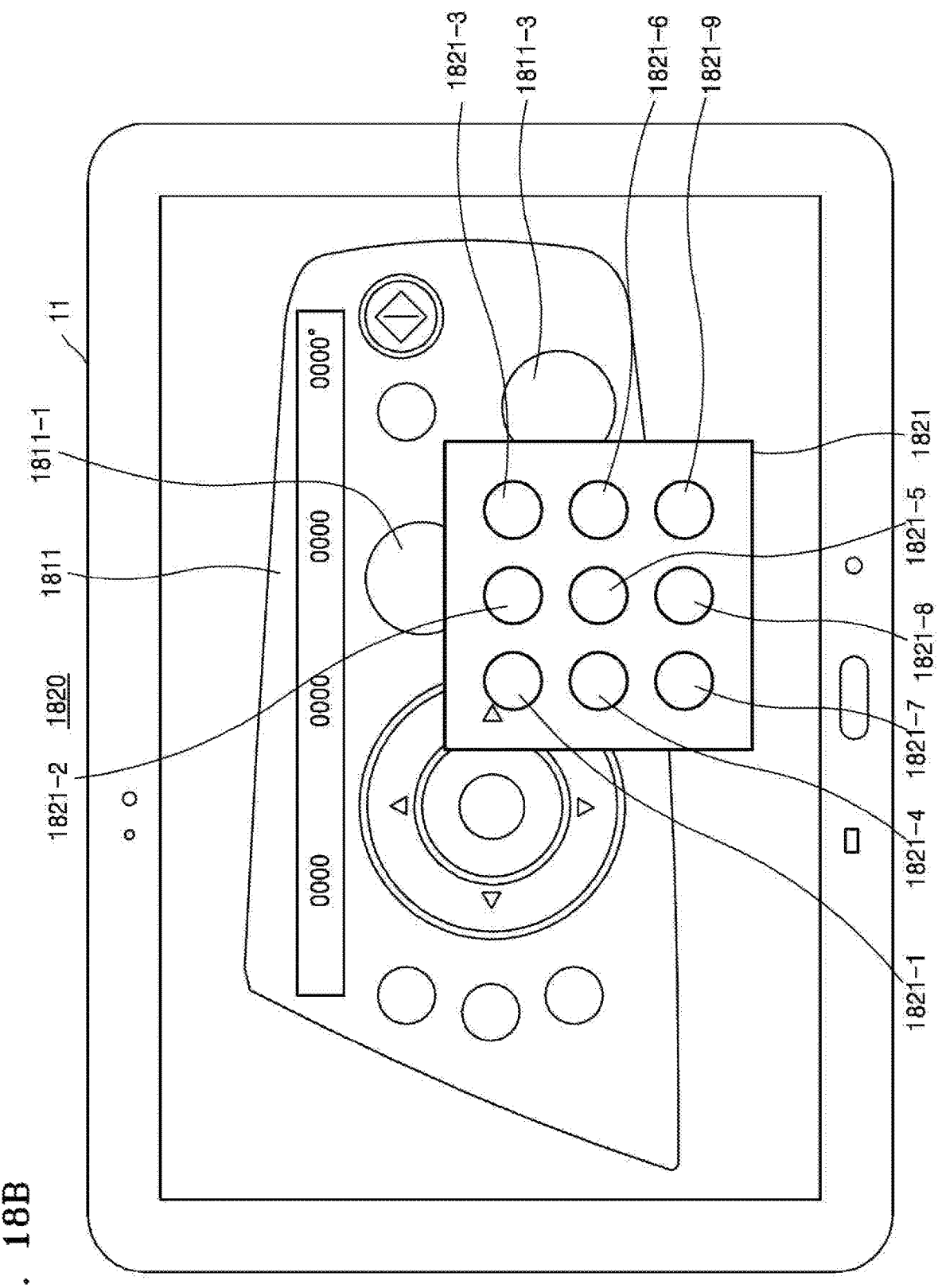

FIGS. 18A and 18B are diagrams of the mobile terminal 11 displaying a user interface 1811 for controlling a medical apparatus, according to another exemplary embodiment.

Referring to 1810 of FIG. 18A, the processor 190 may control a touch screen such that the user interface 1811 for controlling the medical apparatus is displayed. If the number of UI elements that may be displayed on the user interface 1811 is limited, representative UI elements 1811-1, 1811-2, and 1811-3 that represent a plurality of UI elements may be displayed on the user interface 1811.

In this case, in response to a user input for selecting the representative UI element 1811-1, the processor 190 may control a touch screen such that lower level UI elements 1821-1 to 1821-9 of the representative UI element 1811-1 are displayed, as shown in 1820 of FIG. 18B. The lower level UI elements 1821-1 to 1821-9 may be displayed on a pop-up screen 1821, a split screen, or a new screen. When the pop-up screen 1821 is displayed, the pop-up screen 1821 may be displayed near the representative UI element 1811-1 with an animation effect (e.g., enlarging, flashing, or rotating).

FIGS. 19A and 19B are diagrams of the mobile terminal 11 displaying a user interface for controlling a medical apparatus, according to another exemplary embodiment.

Referring to 1910 of FIG. 19A, the processor 190 may control the touch screen 200 such that the identification information 21-1 and 22-1 that corresponds to the first and second medical apparatuses 21 and 22 is displayed. While the identification information 21-1 and 22-1 is being displayed, the touch screen 200 may detect a user input for selecting the identification information 21-1 that corresponds to the first medical apparatus 21 from among the identification information 21-1 and 22-1.

In response to the user input, the processor 190 may control the touch screen 200 such that a user interface screen 1921, which includes UI elements 1921-1 to 1921-4 and 1922-1 to 1922-5 that are configured in a tree structure, is displayed, as shown in 1920 of FIG. 19B. For example, the processor 190 may control the touch screen 200 such that a hierarchy structure, which includes the upper level UI elements 1921-1 and 1921-4 that groups the lower level UI elements 1922-1 to 1922-5 for controlling the first medical apparatus 21, is displayed. In response to a user input for selecting the upper level UI elements 1921-1 and 1921-4, the processor 190 may control the touch screen 200 such that the lower level UI elements 1922-1 to 1922-5 for controlling the first medical apparatus 21 are displayed. The UI element 1921-3 for directly controlling the first medical apparatus 21 may be included in the UI elements 1921-1 to 1921-4. In this case, the UI element 1921-3 may have a different type of identification information 1923 so that the UI element 1921-3 is distinguished from other upper level UI elements 1921-1, 1921-2, and 1921-4 that include the lower level UI elements 1922-1 to 1922-5.

Figure 20A:
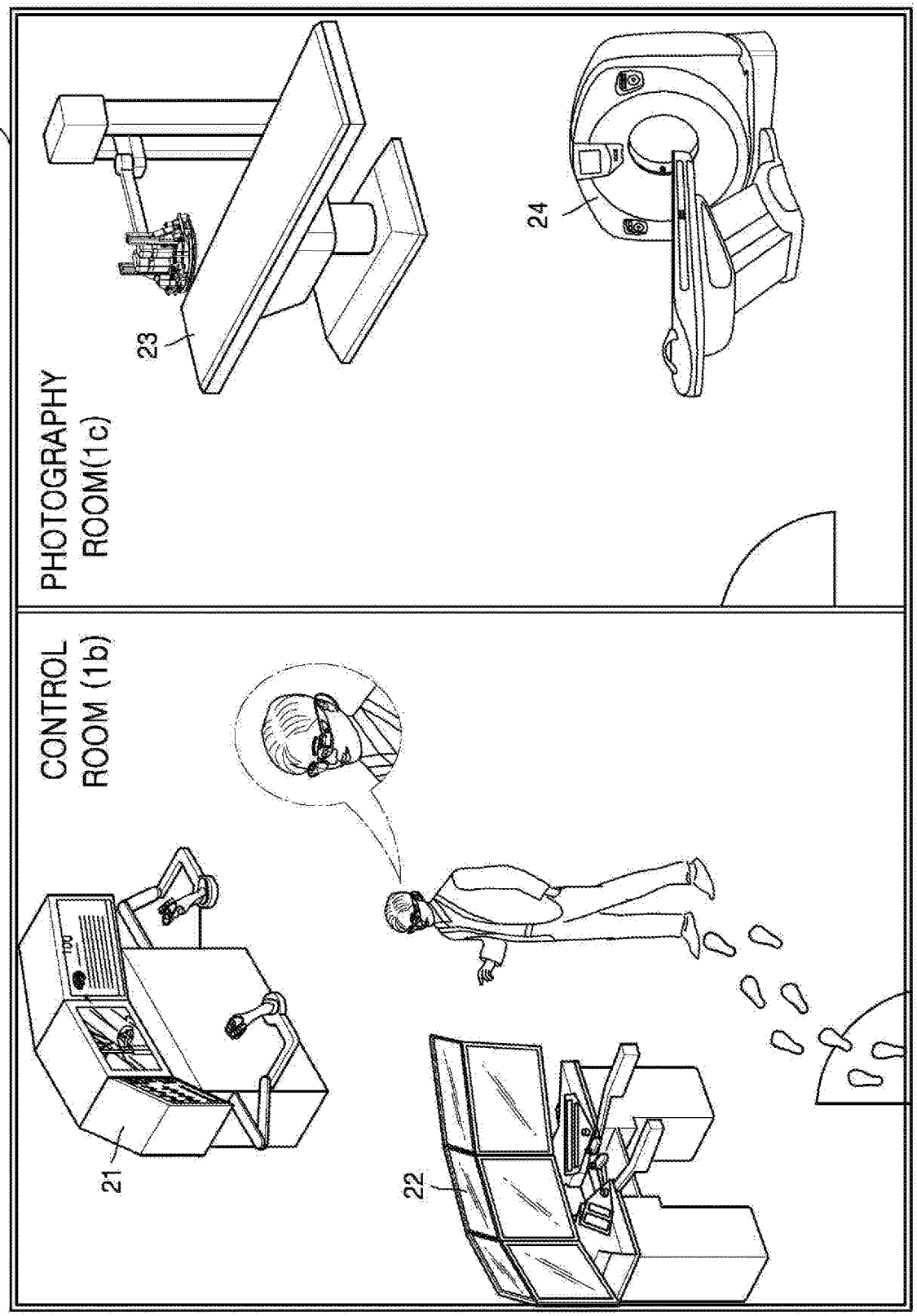
Figure 20B:
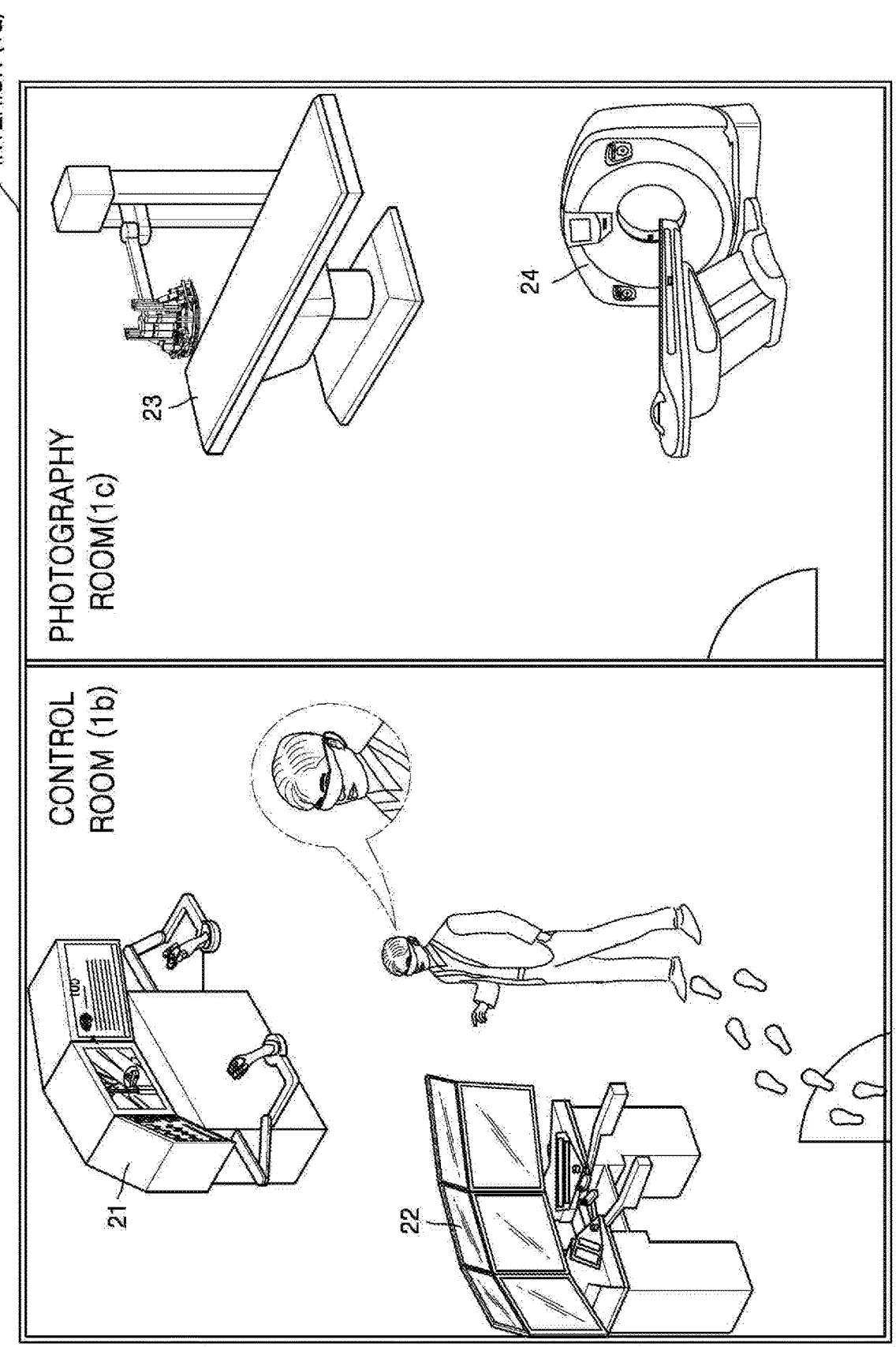

FIGS. 20A to 20C are diagrams of various types of mobile terminals to which an exemplary embodiment may be applied.

The above-described exemplary embodiments may be applied to wearable devices as shown in FIGS. 20A to 20C.

In FIG. 20A, in the case that a wearable device is a glasses-type device, a user may control a medical apparatus by using the glasses-type device. For example, when identification information of the medical apparatus or a user interface for controlling the medical apparatus is displayed on the glasses-type device, in response to a voice input of the user for selecting the identification information or a UI element in the user interface, a user interface of the medical apparatus which corresponds to the selected UI element may be displayed or a function of the medical apparatus which corresponds to the selected UI element may be controlled.

Alternatively, in FIG. 20B, in the case a wearable device is an HMD, the user may control the medical apparatus by using the HMD. For example, when identification information of the medical apparatus or a user interface for controlling the medical apparatus is displayed on the HMD, in response to a voice input, gaze, or a gesture of the user for selecting the identification information or a UI element in the user interface, a user interface of the medical apparatus which corresponds to the selected UI element may be displayed or a function of the medical apparatus which corresponds to the selected UI element may be controlled.

Alternatively, in FIG. 20C, in the case that a wearable device is a wrist watch, the user may control the medical apparatus by using the wrist watch. For example, when identification information of the medical apparatus or a user interface for controlling the medical apparatus is displayed on the wrist watch, in response to a voice input or a touch input of the user for selecting the identification information or a UI element in the user interface, a user interface of the medical apparatus which corresponds to the selected UI element may be displayed or a function of the medical apparatus which corresponds to the selected UI element may be controlled FIG. 21 is a flowchart of a method of controlling a medical apparatus, according to an exemplary embodiment.

Figure 21:
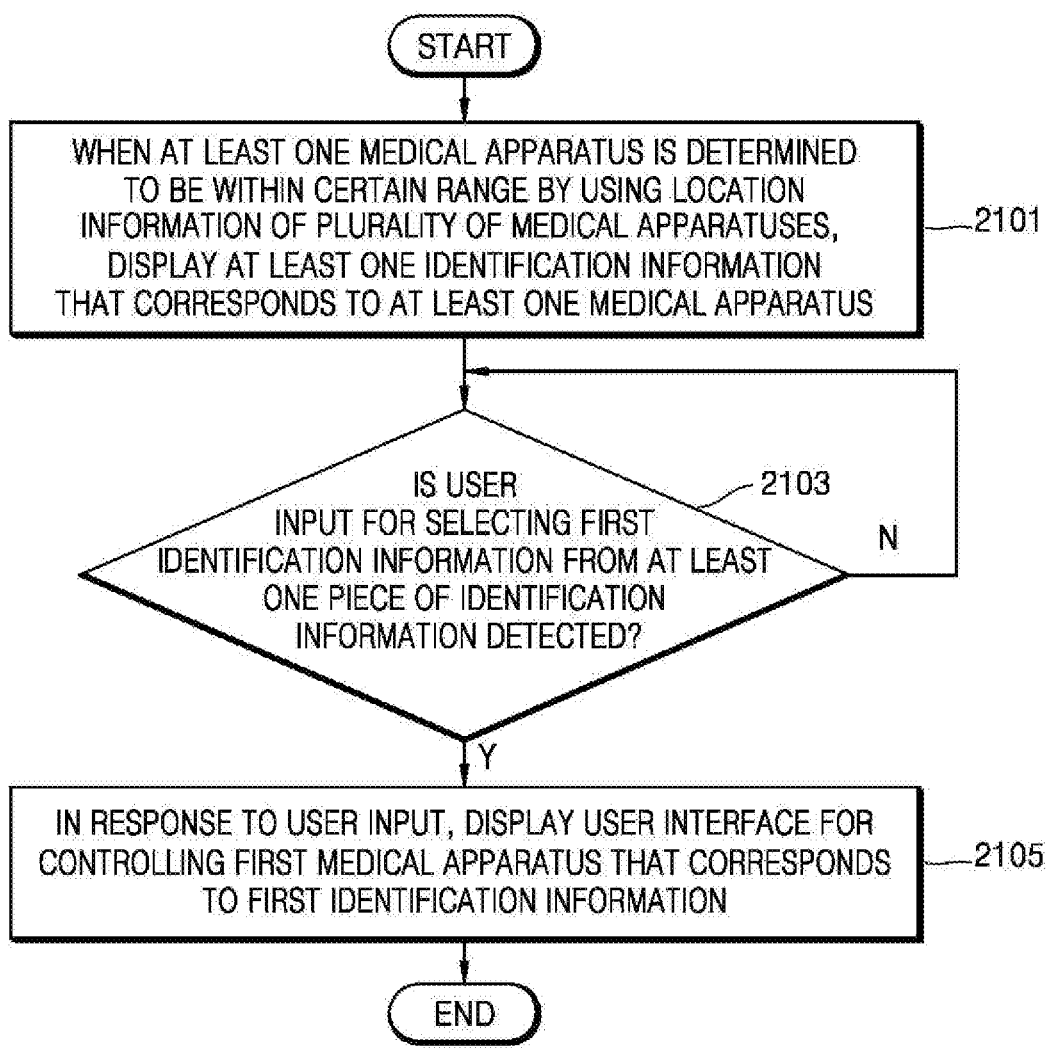
FIGS. 21 and 22 are flowcharts of a method of controlling a medical apparatus, according to an exemplary embodiment.

Referring to FIG. 21, when at least one medical apparatus that is within a certain range from the mobile terminal 11 is determined by using pieces of location information of the first to fourth medical apparatuses 21 to 24, the mobile terminal 11 may display at least one piece of identification information that corresponds to the determined at least one medical apparatus (operation 2101).

Next, the mobile terminal 11 may determine whether a user input for selecting first identification information from the at least one piece of identification information is detected (operation 2103). When the user input for selecting the first identification information from the at least one piece of identification information is detected, in response to the user input, the mobile terminal 11 may display a user interface for controlling a first medical apparatus that corresponds to the first identification information (operation 2105). In this case, a plurality of UI elements in the displayed user interface may be arranged in the same order or the same direction as a plurality of UI elements in a manipulator of the first medical apparatus.

Figure 22:
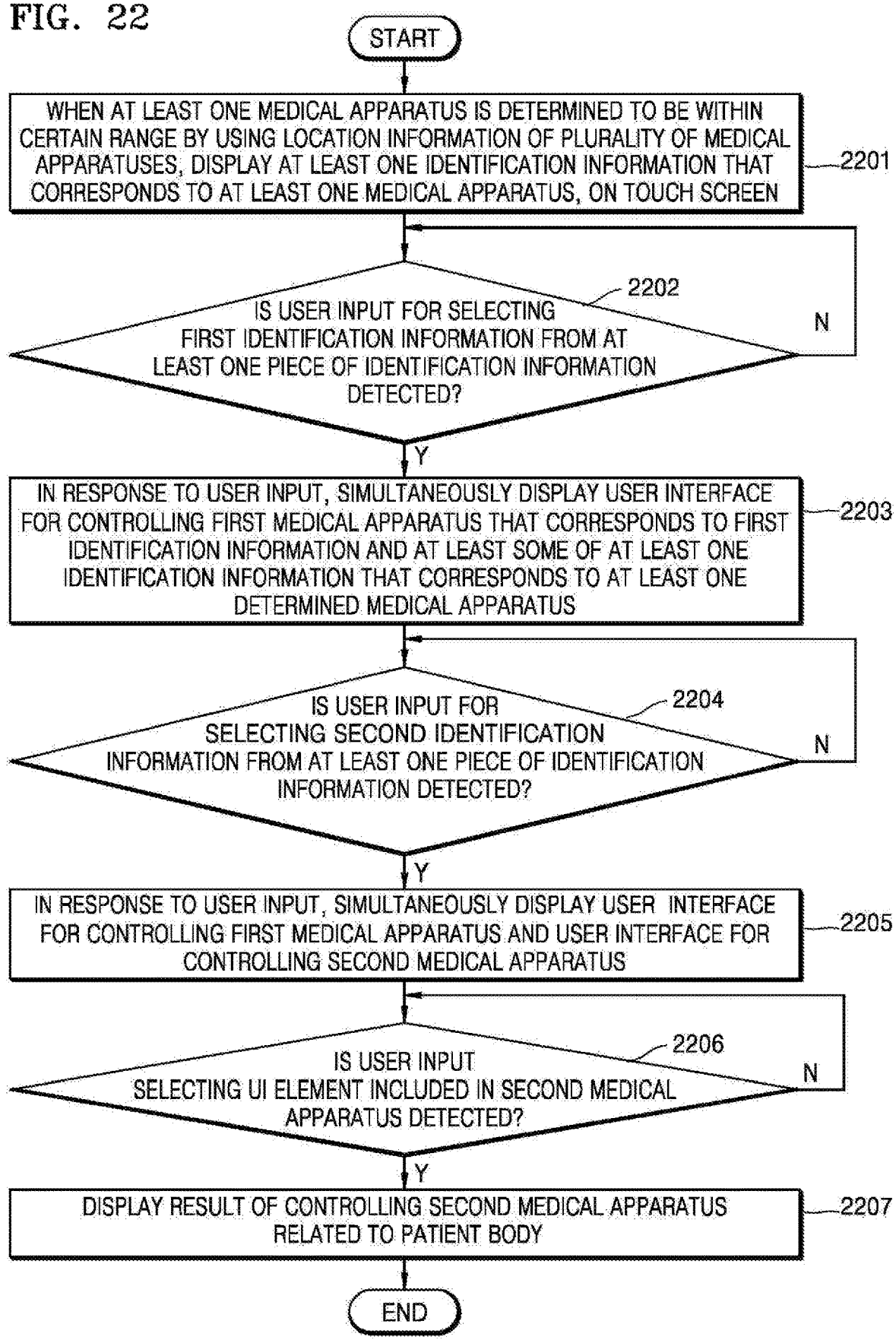

FIG. 22 is a flowchart of a method of controlling a medical apparatus, according to an exemplary embodiment.

Referring to FIG. 22, when at least one medical apparatus that is within a certain range from the mobile terminal 11 is determined by using pieces of location information of the first to fourth medical apparatuses 21 to 24, the mobile terminal 11 may display at least one piece of identification information that corresponds to the determined at least one medical apparatus (operation 2201).

Next, the mobile terminal 11 may determine whether a user input for selecting first identification information from the at least one piece of identification information is detected (operation 2202). When the user input for selecting the first identification information from the at least one piece of identification information is detected, in response to the user input, the mobile terminal 11 may display a user interface for controlling a first medical apparatus that corresponds to the first identification information (operation 2203). In this case, the mobile terminal 11 may simultaneously display the user interface for controlling the first medical apparatus and at least some of the at least one piece of identification information that corresponds to the at least one medical apparatus.

Then, the mobile terminal 11 may determine whether a user input for selecting second identification information from the at least one piece of identification information is detected (operation 2204). When the user input for selecting the second identification information from the at least one piece of identification information is detected, in response to the user input, the mobile terminal 11 may simultaneously display the user interface for controlling the first medical apparatus that corresponds to the first identification information and a user interface for controlling the second medical apparatus that corresponds to the second identification information on a touch screen (operation 2205).

Next, the mobile terminal 11 may determine whether a user input for selecting a UI element in the second medical apparatus is detected (operation 2206). When the user input for selecting the UI element in the second medical apparatus is detected, in response to the user input, the mobile terminal 11 may display a result of controlling the second medical apparatus related to the body of a patient (operation 2207).

Devices (e.g., modules or the mobile terminal 11) according to various exemplary embodiments may be operated by, for example, at least one computer (e.g., the processor 190) that executes instructions in at least one program maintained in computer-readable storage media.

When the instructions are executed by the at least one computer (e.g., the processor 190), the at least one computer may perform functions that correspond to the instructions. Here, a computer-readable storage medium may be, for example, the memory 150.

The at least one program may be included in computer-readable storage media, for example, hard disks, floppy disks, magnetic media (e.g., magnetic tapes), optical media (e.g., CD-ROMs), DVDs, magneto-optical media (e.g., floptical disks), hardware devices (e.g., ROM, RAM, or flash memory). Here, a storage medium is generally included as a portion of the mobile terminal 11. Alternatively, the storage medium may be mounted via a port of the mobile terminal 11 or included in an external device (e.g., cloud, server, or another electronic device) located outside the mobile terminal 11. Also, the at least one program may be separately stored in a plurality of storage media. At least some of the storage media may be in an external device of the mobile terminal 11.

Examples of instructions not only include machine codes that are made by compilers, but also computer-executable high level languages codes that may be executed by using an interpreter. The above-described hardware devices may be configured to be operated as at least one software module, and vice versa, to perform operations of various exemplary embodiments.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. While one or more exemplary embodiments have been described with reference to the figures, it will be understood by those of ordinary skill in the art that various changes in form and details may be made therein without departing from the spirit and scope as defined by the following claims.

What is claimed is:

1. A method of controlling a medical apparatus by using a mobile terminal that includes a touch screen, the method comprising:

displaying, in response to a determining that at least one medical apparatus is within a certain distance from the mobile terminal based on location information of the at least one medical apparatus, at least one piece of identification information that corresponds to a first medical apparatus;

detecting a first user input for selecting first identification information from the at least one piece of identification information;

displaying, in response to the first user input, a first user interface for controlling the first medical apparatus, on the touch screen;

displaying, in response to an occurrence of an emergency situation of a patient while controlling the first medical apparatus, notification information indicating the occurrence of the emergency situation on the touch screen, wherein the occurrence of the emergency situation includes at least one of occurrence of a side-effect, cardiac arrest, shock or death;

in accordance with detection of a user input for selecting the notification information or an elapse of a predetermined time after the notification information is displayed:

changing, in response to the occurrence of the emergency situation of the patient, at least one user interaction element (UI element) from an activated state to a deactivated state among a plurality of UI elements in the user interface, wherein the at least one UI element changed includes a UI element for starting an image scan; and highlighting, in response to the occurrence of the emergency situation of the patient, at least one UI element for taking actions in response to the occurrence of the emergency situation among the plurality of UI elements, wherein the at least one UI element for taking actions in response to the occurrence of the emergency situation includes at least one of a UI element for locking and unlocking a cradle, a UI element for manipulating a table, a UI element for pausing or ending a scan operation, a UI element for manipulating a tilt of a gantry, a UI element for stopping an operation of a gantry, or a UI element for stopping an operation of an injector;

detecting a second user input controlling the first medical apparatus; and displaying, in response to the second user input, an image of the patient or the diagnosis of the patient as a result of controlling the first medical apparatus via the first user interface, on the touch screen.

2. The method of claim 1, wherein the first medical apparatus is found by a medical apparatus management server and determined to be within the certain distance from the mobile terminal.

3. The method of claim 1, further comprising:
detecting a third user input for selecting second identification information from the at least one piece of identification information;

displaying, in response to the third user input, a second user interface for controlling a second medical apparatus that corresponds to the second identification information, on the touch screen; and displaying, in response to a fourth user input, a result of controlling the second medical apparatus in relation to a body of the patient.

4. The method of claim 1, wherein the displaying the first user interface for controlling the first medical apparatus comprises simultaneously displaying the first user interface for controlling the first medical apparatus and the at least one piece of identification information.

5. The method of claim 1, wherein the displaying the at least one piece of identification information comprises displaying the at least one piece of identification information on a layout based on a location where the first medical apparatus is installed.

6. The method of claim 1, wherein the plurality of UI elements in the first user interface are arranged in a same order, a same direction, or both the same order and the same direction as a plurality of UI elements in the manipulator of the first medical apparatus.

7. The method of claim 1, wherein the first identification information is at least one selected from the location information of the first medical apparatus, a model name of the first medical apparatus, a manufacturer of the first medical apparatus, an image of the first medical apparatus, and a shortcut icon of an application related to the first medical apparatus.

8. The method of claim 1, wherein the touch screen includes a motion detector and the first user input is based on a motion detector signal.

9. The method of claim 1, wherein the location information is at least one selected from coordinate information, distance information, and direction information of the at least one medical apparatus.

10. A mobile terminal for controlling a medical apparatus, the mobile terminal comprising:
a touch screen; and
a processor configured to:
display, in response to a determining that at least one medical apparatus is within a certain distance from the mobile terminal based on location information of the at least one medical apparatus, at least one piece of identification information that corresponds to a first medical apparatus;

detect a first user input for selecting first identification information from the at least one piece of identification information;

display, in response to the first user input, a first user interface for controlling the first medical apparatus, on the touch screen;

display, in response to an occurrence of an emergency situation of a patient while controlling the first medical apparatus, notification information indicating the occurrence of the emergency situation on the touch screen, wherein the occurrence of the emergency situation includes at least one of occurrence of a side-effect, cardiac arrest, shock or death;

in accordance with detection of a user input for selecting the notification information or an elapse of a predetermined time after the notification information is displayed:

change, in response to the occurrence of the emergency situation of the patient, at least one user interaction element (UI element) from an activated state to a deactivated state among a plurality of UI elements in the user interface, wherein the at least one UI element changed includes a UI element for starting an image scan; and highlight, in response to the occurrence of the emergency situation of the patient, at least one UI element for taking actions in response to the occurrence of the emergency situation among the plurality of UI elements, wherein the at least one UI element for taking actions in response to the occurrence of the emergency situation includes at least one of a UI element for locking and unlocking a cradle, a UI element for manipulating a table, a UI element for pausing or ending a scan operation, a UI element for manipulating a tilt of a gantry, a UI element for stopping an operation of a gantry, or a UI element for stopping an operation of an injector;

detect a second user input controlling the first medical apparatus; and display, in response to the second user input, an image of the patient or the diagnosis of the patient as a result of control the first medical apparatus via the first user interface, on the touch screen.

11. The mobile terminal of claim 10, wherein the first medical apparatus is found by a medical apparatus management server and determined to be within the certain distance from the mobile terminal.

12. The mobile terminal of claim 10, wherein the processor is further configured to:
detect a third user input for selecting second identification information from the at least one piece of identification information;

control the touch screen to, in response to the third user input for selecting the second identification information, display a second user interface for controlling a second medical apparatus that corresponds to the second identification information, and display, in response to a fourth user input, a result of controlling the second medical apparatus in relation to a body of the patient.

13. The mobile terminal of claim 10, wherein the touch screen simultaneously displays the first user interface for controlling the first medical apparatus and the at least one piece of identification information.

14. The mobile terminal of claim 10, wherein in response to the at least one piece of identification information being displayed on the touch screen, the touch screen displays the at least one piece of identification information on a layout based on a location where the first medical apparatus is installed.

15. The mobile terminal of claim 10, wherein the plurality of UI elements in the first user interface are arranged in a same order, a same direction, or both the same order and the same direction as a plurality of UI elements in the manipulator of the first medical apparatus.

16. The mobile terminal of claim 10, wherein the first identification information is at least one selected from the location information of the first medical apparatus, a model name of the first medical apparatus, a manufacturer of the first medical apparatus, an image of the first medical apparatus, and a shortcut icon of an application related to the first medical apparatus.

17. The mobile terminal of claim 10, wherein the touch screen includes a motion detector and the first user input is based on a motion detector signal.

18. The mobile terminal of claim 10, wherein the location information is at least one selected from coordinate information, distance information, and direction information of the at least one medical apparatus.

19. A non-transitory computer-readable recording medium having recorded thereon a program that performs:
   displaying, in response to a determining that at least one medical apparatus is within a certain distance from a mobile terminal based on location information of the at least one medical apparatus, at least one piece of identification information that corresponds to a first medical apparatus, on a touch screen;
   detecting a first user input for selecting first identification information from the at least one piece of identification information;
   displaying, in response to the first user input, a first user interface for controlling the first medical apparatus, on the touch screen;
   displaying, in response to an occurrence of an emergency situation of a patient while controlling the first medical apparatus, notification information indicating the occurrence of the emergency situation on the touch screen, wherein the occurrence of the emergency situation includes at least one of occurrence of a side-effect, cardiac arrest, shock or death;
   in accordance with detection of a user input for selecting the notification information or an elapse of a predetermined time after the notification information is displayed:
   changing, in response to the occurrence of the emergency situation of the patient, at least one user interaction element (UI element) from an activated state to a deactivated state among a plurality of UI elements in the user interface, wherein the at least one UI element changed includes a UI element for starting an image scan; and
   highlighting, in response to the occurrence of the emergency situation of the patient, at least one UI element for taking actions in response to the occurrence of the emergency situation among the plurality of UI elements, wherein the at least one UI element for taking actions in response to the occurrence of the emergency situation includes at least one of a UI element for locking and unlocking a cradle, a UI element for manipulating a table, a UI element for pausing or ending a scan operation, a UI element for manipulating a tilt of a gantry, a UI element for stopping an operation of a gantry, or a UI element for stopping an operation of an injector;
   detecting a second user input controlling the first medical apparatus; and
   displaying, in response to the second user input, an image of the patient or the diagnosis of the patient as a result of controlling the first medical apparatus via the first user interface, on the touch screen.

* * * * *